United States Patent
Sosa et al.

(10) Patent No.: US 11,254,948 B2
(45) Date of Patent: Feb. 22, 2022

(54) TRANSGENIC PLANTS HAVING INCREASED TOLERANCE TO ALUMINUM

(71) Applicant: CERES, INC., Thousand Oaks, CA (US)

(72) Inventors: Julissa Sosa, Northridge, CA (US); Wuyi Wang, Newbury Park, CA (US)

(73) Assignee: Ceres, Inc., Thousand Oaks, CA (US)

( * ) Notice: Subject to any disclaimer, the term of this patent is extended or adjusted under 35 U.S.C. 154(b) by 231 days.

(21) Appl. No.: 16/575,893

(22) Filed: Sep. 19, 2019

(65) Prior Publication Data

US 2020/0080103 A1 Mar. 12, 2020

Related U.S. Application Data

(62) Division of application No. 15/881,134, filed on Jan. 26, 2018, now Pat. No. 10,472,646, which is a division of application No. 14/355,530, filed as application No. PCT/US2012/062977 on Nov. 1, 2012, now Pat. No. 9,938,536.

(60) Provisional application No. 61/554,788, filed on Nov. 2, 2011.

(51) Int. Cl.
| | |
|---|---|
| *C12N 15/82* | (2006.01) |
| *A23L 5/00* | (2016.01) |
| *A23L 7/10* | (2016.01) |
| *A23L 25/00* | (2016.01) |
| *A23K 10/00* | (2016.01) |
| *C07K 14/415* | (2006.01) |

(52) U.S. Cl.
CPC .......... *C12N 15/8271* (2013.01); *A23K 10/00* (2016.05); *A23L 5/00* (2016.08); *A23L 7/10* (2016.08); *A23L 25/00* (2016.08); *C07K 14/415* (2013.01); *C12N 15/8216* (2013.01); *A23V 2002/00* (2013.01)

(58) Field of Classification Search
None
See application file for complete search history.

(56) References Cited

U.S. PATENT DOCUMENTS

| | | |
|---|---|---|
| 4,987,071 A | 1/1991 | Cech et al. |
| 5,034,323 A | 7/1991 | Jorgensen et al. |
| 5,204,253 A | 4/1993 | Sanford et al. |
| 5,231,020 A | 7/1993 | Jorgensen et al. |
| 5,254,678 A | 10/1993 | Haseloff et al. |
| 5,538,880 A | 7/1996 | Lundquist et al. |
| 5,766,847 A | 6/1998 | Jackie et al. |
| 5,878,215 A | 3/1999 | Kling et al. |
| 6,013,863 A | 1/2000 | Lundquist et al. |
| 6,326,527 B1 | 12/2001 | Kirihara et al. |
| 6,329,571 B1 | 12/2001 | Hiei |
| 6,423,885 B1 | 7/2002 | Waterhouse et al. |
| PP13,008 P2 | 9/2002 | Walsh |
| 6,452,067 B1 | 9/2002 | Brook et al. |
| 6,573,099 B2 | 6/2003 | Graham |
| PP14,743 P2 | 5/2004 | Speichert et al. |
| 6,753,139 B1 | 6/2004 | Baulcombe et al. |
| 6,777,588 B2 | 8/2004 | Waterhouse et al. |
| PP15,193 P2 | 9/2004 | Smith et al. |
| 6,906,244 B2 | 6/2005 | Fischer et al. |
| PP16,176 P3 | 1/2006 | Cosner et al. |
| 7,179,904 B2 | 2/2007 | Kwok |
| PP18,161 P2 | 10/2007 | Probst |
| 7,582,809 B2 | 9/2009 | Kochian et al. |
| 8,299,318 B2 | 10/2012 | Brover et al. |
| 2003/0175783 A1 | 9/2003 | Waterhouse et al. |
| 2003/0175965 A1 | 9/2003 | Lowe et al. |
| 2003/0180945 A1 | 9/2003 | Wang et al. |
| 2004/0214330 A1 | 10/2004 | Waterhouse et al. |
| 2005/0032221 A1 | 2/2005 | Chang et al. |
| 2006/0015970 A1 | 1/2006 | Pannell et al. |
| 2006/0123505 A1 | 6/2006 | Kikuchi et al. |
| 2006/0260004 A1 | 11/2006 | Fang et al. |
| 2006/0265788 A1 | 11/2006 | Rommens |
| 2007/0056058 A1 | 3/2007 | Olivier et al. |
| 2008/0087675 A1 | 4/2008 | Connor |
| 2008/0229442 A1* | 9/2008 | Zhou .................. C12N 15/8271 800/266 |
| 2008/0235823 A1 | 9/2008 | Medrano et al. |
| 2009/0038581 A1 | 2/2009 | Huettlin |
| 2009/0100539 A1* | 4/2009 | Zhou .............. C12Y 208/02015 800/278 |
| 2009/0144847 A1 | 6/2009 | Shaikh et al. |

(Continued)

FOREIGN PATENT DOCUMENTS

| | | |
|---|---|---|
| EP | 0 534 858 | 4/2000 |
| WO | WO 1996/034959 | 11/1996 |

(Continued)

OTHER PUBLICATIONS

Haberer et al., 2005, Structure and Architecture of the Maize Genome, Plant Physiology 139: 1612-1624.*
U.S. Appl. No. 60/637,140, filed Dec. 16, 2004, Feldmann.
U.S. Appl. No. 60/619,181, filed Oct. 14, 2004, Medrano.
U.S. Appl. No. 60/612,891, filed Sep. 23, 2004, Kwok.
U.S. Appl. No. 60/583,691, filed Mar. 30, 2004, Alexandrov et al.
U.S. Appl. No. 60/583,609, filed Jun. 30, 2004, Alexandrov.
U.S. Appl. No. 60/558,869, filed Apr. 1, 2004, Cook et al.
U.S. Appl. No. 60/544,771, filed Feb. 13, 2004, Cook et al.
U.S. Appl. No. 60/518,075, filed Nov. 6, 2003, Pennell et al.

(Continued)

*Primary Examiner* — Bratislav Stankovic
(74) *Attorney, Agent, or Firm* — Dentons US LLP

(57) ABSTRACT

Methods and materials for modulating aluminum tolerance in plants are disclosed. For example, nucleic acids encoding aluminum tolerance-modulating polypeptides are disclosed as well as methods for using such nucleic acids to transform plant cells. Also disclosed are plants having increased tolerance to aluminum and methods of increasing plant yield in soil containing elevated levels of aluminum.

13 Claims, 18 Drawing Sheets

Specification includes a Sequence Listing.

(56) References Cited

U.S. PATENT DOCUMENTS

| | | |
|---|---|---|
| 2009/0276918 A1 | 11/2009 | Choi et al. |
| 2010/0223695 A1 | 9/2010 | Sivasankar et al. |
| 2010/0269222 A1 | 10/2010 | Medrano et al. |
| 2010/0287662 A1 | 11/2010 | Niu et al. |
| 2011/0093981 A9 | 4/2011 | La Rosa et al. |
| 2011/0217776 A1 | 9/2011 | Hu et al. |
| 2012/0102599 A1 | 4/2012 | Kim et al. |
| 2012/0131696 A1 | 5/2012 | Aayal et al. |
| 2012/0216318 A1 | 8/2012 | La Rosa et al. |
| 2013/0117881 A1 | 5/2013 | Cook et al. |
| 2013/0236208 A1 | 9/2013 | Komatsu |
| 2018/0223304 A1 | 8/2018 | Sosa et al. |

FOREIGN PATENT DOCUMENTS

| | | |
|---|---|---|
| WO | WO 9701952 | 1/1997 |
| WO | WO 9836083 | 8/1998 |
| WO | WO 9853083 | 11/1998 |
| WO | WO 9932619 | 7/1999 |
| WO | WO 02/46449 | 6/2002 |
| WO | WO 2005/098007 | 10/2005 |
| WO | WO 2006/005023 | 1/2006 |
| WO | WO 2006034479 | 3/2006 |
| WO | WO 2006036864 | 4/2006 |
| WO | WO 2007055826 | 5/2007 |
| WO | WO 2007120989 | 10/2007 |
| WO | WO 2009038581 | 3/2009 |
| WO | WO 2009099899 | 8/2009 |
| WO | WO 2009127441 | 10/2009 |
| WO | WO 2009146015 | 12/2009 |
| WO | WO 2007044988 | 4/2017 |

OTHER PUBLICATIONS

U.S. Appl. No. 60/505,689, filed Sep. 23, 2003, Cook et al.
U.S. Appl. No. 60/757,544, filed Jan. 9, 2006, Dang.
U.S. Appl. No. 60/776,307, filed Feb. 24, 2006, Kwok et al.
Abler, et al, "Isolation and characterization of a genomic sequence encoding the maize Cat3 catalase gene," Plant Mol. Biol., Sep. 1993, 22:1031-1038.
Akashi et al., "Gene discovery by ribozyme and siRNA libraries," Nature Reviews Mol. Cell Biology, May 2005, 6:413-422.
Alonso-Blanco et al. "*Arabidopsis* Protocols," Methods in Molecular Biology, 1998, 82:137-146.
Baerson et al., "Developmental regulation of an acyl carrier protein gene promoter in vegetative and reproductive tissues," Plant Mol. Biol., 1993, 22(2):255-267.
Bateman et al., "Pfam 3.1: 1313 multiple alignments and profile HMMs match the majority of proteins," Nucl. Acids Res., 1999, 27:260-262.
Braga et al., "Expression of the Cry lAb Protein in Genetically Modified Sugarcane for the Control of *Diatraea saccharalis* (Lepidoptera: Crambidae)," Journal of New Seeds, 2003, 5:209-221.
Burr et al., "Gene Mapping with Recombinant Inbreds in Maize," Genetics, 1988, 118:519-526.
Burr et al., "Mapping Genes with Recombinant Inbreds," The Maize Handbook, 1994, pp. 249-254.
Bustos et al., "Regulation of B-Glucuronidase Expression in Transgenic Tobacco Plants by an A/TRich, cis-Acting Sequence Found Upstream of a French Bean B-Phaseolin Gene," The Plant Cell, 1989, 1(9):839-853.
Cerdan et al., "A 146 bp fragment of the tobacco Lhcbl*2 promoter confers very-low-fluence and high-irradiance responses of phytochrome to a minimal CaMV 35S promoter," Plant Mol. Biol., 1997, 33:245-255.
Chen et al., "Functional analysis of regulatory elements in a plant embryo-specific gene," Proc. Natl. Acad. Sci. USA, 1986, 83:8560-8564.
Chenna et al., "Multiple sequence alignment with the Clustal series of programs," Nucleic Acids Res., 2003, 31(13):3497-500.
Christian et al., "Targeting DNA double-strand breaks with TAL effector nucleases," Genetics, Oct. 2010, 186: 757-761.
Conceicao, "A cotyledon regulatory region is responsible for the different spatial expression patterns of *Arabidopsis* 2S albumin genes," The Plant Journal, 1994, 5:493-505.
Conkling et al., "Isolation of Transcriptionally Regulated Root-Specific Genes from Tobacco," Plant Physiol., 1990, 93:1203-1211.
Dai et al., "RF2b, a rice bZIP transcription activator, interacts with RF2a and is involved in symptom development of rice tungro disease," Proc. Natl. Acad. Sci. USA, 2004, 101(2):687-692.
De Feyter, "Expressing Ribozymes in Plants," Methods in Molecular Biology, 1997, 74(43):403-415.
DelHaize et al, 1995, Plant Physiology 107: 315-321.
Do et al., "ProbCons: Probabilistic consistency-based multiple sequence alignment," Genome Res., 2005, 15(2):330-40.
Durbin et al., Biological Sequence Analysis: Probabilistic Models of Proteins and Nucleic Acids, Cambridge University Press, Cambridge, UK (1998).
Fang et al., "Systematic sequence analysis and identification of tissue-specific or stress-responsive genes of NAC transcription factor family in rice," Mol. Genet. Genomics, Dec. 2008, 280:547-563.
Fejes et al., "A 268 bp upstream sequence mediates the circadian clock-regulated transcription of the wheat Cab-1 gene in transgenic plants," Plant Mol. Biol., 1990, 15:921-932.
Fromm et al., An Octopine Synthase Enhancer Element Directs Tissue-Specific Expression and Binds ASF-1, a Factor from Tobacco Nuclear Extracts, The Plant Cell, 1989, 1:977-984.
Guo et al., 2004, Proceedings of the National Academy of Sciences USA 101: 9205-9210.
Gardiner et al., "Development of a Core RFLP Map in Maize Using an Immortalized F2 Population," Genetics Society of America, 1993, 134: 917-930.
Keshin et al., 2004, Protein Science 13:1043-1055.
National Center for Biotechnology Information GenBank Accession No. AF096096, "Genes controlling fertilization-independent seed development in *Arabidopsis thaliana*," 1999, 2 pages.
National Center for Biotechnology Information GenBank Accession No. AF129516, "Mutations in FIE, a WD polycomb group gene, allow endosperm development without fertilization," 1999, 2 pages.
National Center for Biotechnology Information GenBank Accession No. L05934, "Isolation and characterization of a genomic sequence encoding the maize Cat3 catalase gene," 1993, 3 pages.
National Center for Biotechnology Information GenBank Accession No. U93215, "*Arabidopsis thaliana* chromosome 2 BAC T6B20 genomic sequence," 2002, 42 pages.
Green et al., "Binding site requirements for pea nuclear protein factor GT-1 correlate with sequences required for light-dependent transcriptional activation of the rbcS-3A gene," The EMBO J., 1988, 7:4035-4044.
Guerois, Raphael, "Predicting Changes in the Stability of Proteins and Protein Complexes: A Study of More Than 1000 Mutations," J Mol. Biol. (2002) 320, 369-387.
Hong et al., "Promoter sequences from two different *Brassica napus* tapetal oleosin-like genes direct tapetal expression of B-glucuronidase in transgenic *Brassica* plants," Plant Mol. Biol., 1997, 34(3):549-555.
Hyrup et al., "Peptide Nucleic Acids (PNA): Synthesis, Properties and Potential Applications," Bioorganic & Medicinal Chemistry, 1996, 4(1):5-23.
Hwang et al. "Aleurone- and embryo-specific expression of the 0-glucuronidase gene controlled by the barley Chi26 and Ltpl promoters in transgenic rice," Plant Cell Reports, 2001, 20:647-654.
International Preliminary Reporton Patentability in International Application No. PCT/US2012/062977, dated May 6, 2014, 10 pages.
International Search Report and Written Opinion in International Application No. PCT/US2012/062977, dated Feb. 25, 2013, 8 pages.
Jordano et al., "A Sunflower Helianthinin Gene Upstream Sequence Ensemble Contains an Enhancer and Sites of Nuclear Protein Interaction," The Plant Cell, 1989, 1:855-866.

(56) References Cited

OTHER PUBLICATIONS

Kasuga et al., "Improving plant drought, salt, and freezing tolerance by gene transfer of a single stress-inducible transcription factor," Nature Biotechnology, 1999, 17: 287-291.
Keller, "Vascular-Specific Expression of the Bean GRP 1.8 Gene is Negatively Regulated," The Plant Cell, 1991, 3(10):1051-1061.
Keskin et al., 2004, Protein Science 13: 1043-1055.
Kochian, "Cellular Mechanisms of Aluminum Toxicity and Resistance in Plants," Annu. Rev. Plant Biol., Jun. 1995, 46:237-260.
Kumar, Prateek, et al., "Predicting the effects of coding non-synonymous variants on protein function using the SIFT algorithm," Nature Publishing Group, 2009, pp. 1073-1082.
Kumari et al., 2008, Mol. Genet. Genomics 279: 339-357.
Lam et al., "Site-specific mutations alter in vitro factor binding and change promoter expression pattern in transgenic plants," Proc. Natl. Acad. Sci. USA, 1989, 86:7890-7894.
Li et al., "Small dsRNAs induce transcriptional activation in human cells," Proc Natl Acad Sci USA, Nov. 2006, 103(46):17337-42.
Lloyd et al., "Targeted mutagenesis using zinc-finger nucleases in *Arabidopsis*," Proc. Natl. Acad. Sci. USA, Feb. 2005, 102:2232-2237.
Luan et al., A Rice cab Gene Promoter Contains Separate cis-Acting Elements That Regulate Expression in Dicot and Monocot Plants, The Plant Cell, Aug. 1992, 4:971-981.
Lubberstedt et al., "Promoters from Genes for Plastid Proteins Possess Regions with Different Sensitivities toward Red and Blue Light," Plant Physiol., 1994, 104:997-1006.
Matsuoka et al., "Tissue-specific light-regulated expression directed by the promoter of a C4 gene, maize pyruvate, orthophosphate dikinase, in a C3 plant, rice," Proc. Natl. Acad. Sci. USA, Oct. 1993, 90:9586-9590.
Matzke, "RNAi-Mediated Pathways in the Nucleus," Nature Reviews Genetics, Jan. 2005, 6:24-35.
McCallum et al., "Targeted screening for induced mutations," Nature Biotechnology, Apr. 2000, 18: 455-457.
Medberry et al., "The Commelina Yellow Mottle Virus Promoter Is a Strong Promoter in Vascular and Reproductive Tissues," The Plant Cell, Feb. 1992, 4(2):185-192.
Meier et al., "Elicitor-Inducible and Constitutive in Vivo DNA Footprints Indicate Novel cis-Acting Elements in the Promoter of a Parsley Gene Encoding Pathogenesis-Related Protein 1," The Plant Cell, Mar. 1991, 3:309-316.
Mittal, "Improving the Efficiency of RNA Interference in Mammals," Nature Reviews Genetics, May 2004, 5:355-365.
Moore et al., "Cell cycle and genetic requirements of two pathways of nonhomologous endjoining repair of double-strand breaks in *Saccharomyces cerevisiae*," Mol Cell Biol., May 1996, 16(5):2164-2173.
Nature.Com, "Nature Reviews RNA interference collection," Oct. 2005, [retrieved on Apr. 12, 2012]. Retrieved from Internet: URL http://www.nature.com/focus/rnai/index.html. 2 pages.
Ng, et al., "Predicting the Effects off Amino Acid Substitutions on Protein Function," Annu. Rev. Genomics Hum Genet 2006, 7:61-80.
Olsen et al., 2005, Trends in Plant Science 10: 79-87.
Ooka et al., "Comprehensive analysis of NAC family genes in *Oryza sativa* and *Arabidopsis thaliana*," DNA Res., Dec. 2003, 20: 239-247.
Perriman et al., "Effective ribozyme delivery in plant cells," Proc. Natl. Acad. Sci. USA, Jun. 1995, 92(13):6175-6179.
Refseth et al., "Hybridization capture of microsatellites directly from genomic DNA," Electrophoresis, 1997, 18:1519-1523.
Reva, Boris, et al., "Predicting the functional impact of protein mutations: application to cancer genomics," Nucleic Acids Research, 2011, vol. 39, No. 17, pp. 1-14.
Rhoads, "Sequence motifs for calmodulin recognition," FASEB J., 1997, 11(5):331-340.
Richards et al., "Construction of a GFP-BAR plasmid and its use for switchgrass transformation," Plant Cell. Rep., 2001, 20:48-54.

Riggs et al., "Cotyledon Nuclear Proteins Bind to DNA Fragments Harboring Regulatory Elements of Phytohemagglutinin Genes," The Plant Cell, Jun. 1989, 1(6):609-621.
Rivera et al., "Genomic evidence for two functionally distinct gene classes," Proc. Natl. Acad. Sci. USA, May 1998, 95:6239-6244.
Ryan et al., "The identification of aluminum-resistance genes provides opportunities for enhancing crop production on acid soils," Journal of Experimental Botany, Jan. 2011, 62:9-20.
Sanchez et al. "Replenishing Soil Fertility in Africa," Agroforestry Systems, Sep. 1998, 42(3):291-294.
Sandhya, Sankaran, "CUSP: an algorithm to distinguish structurally conserved and unconserved regions in protein lomain alignments and its application in the study of large length variations," BioMed Central, May 2008, pp. 1-14.
Shaff et al., "GEOCHEM-EZ: a chemical speciation program with greater power and flexibility," Plant Soil, 2010, 330: 207-214.
Sheridan et al., "The marl Gene: Controlling the Commitment to the Meiotic Pathway in Maize," Genetics, 1996, 142:1009-1020.
Shibuya et al., "RNA-directed DNA methylation induces transcriptional activation in plants," Proc Natl Acad Sci USA, Feb. 2009,106(5):1660-1665.
Slocombe et al., "Temporal and Tissue-Specific Regulation of a *Brassica napus* Stearoyl-Acyl Carrier Protein Desaturase Gene," Plant Physiol., 1994, 104(4):167-176.
Somleva et al., "Agrobacterium-Mediated Genetic Transformation of Switchgrass," Crop Sci., 2002, 42:2080-2087.
Sonnhammer et al., "Pfam: A Comprehensive Database of Protein Domain Families Based on Seed Alignments," Proteins, 1997, 28:405-420.
Sonnhammer et al., "Pfam: multiple sequence alignments and HIVIM-profiles of protein domains," Nucl. Acids Res., 1998, 26:320-322.
Souer et al., "The no apical meristem gene of Petunia is required for pattern formation in embryos and flowers and is expressed at meristem and primordia boundaries," Cell, Apr. 1996, 85:159-170.
Stemple, "TILLING—a high-throughput harvest for functional genomics," Nat Rev Genet, Feb. 2004, 5(2):145-50.
Summerton et al., "Morpholino Antisense Oligomers: Design, Preparation, and Properties," Antisense Nucleic Acid Drug Dev., 1997, 7:187-195.
Thornton et al., 2000, Nature Structural Biology, structural genomic supplement, Nov. 2000: 991-994.
Tovkach et al., "A toolbox and procedural notes for characterizing novel zinc finger nucleases for genome editing in plant cells," The Plant Journal, 2009, 57:747-757.
Townsend et al., "High-frequency modification of plant genes using engineered zinc-finger nucleases," Nature, May 2009, 459:442-445.
Truernit et al., 'The promoter of the *Arabidopsis thaliana* SUC2 sucrose-H+ symporter gene directs expression of B-glucuronidase to the phloem: Evidence for phloem loading and unloading by SUC2, Planta 1995;196(3):564-570.
Urao et al, "Molecular cloning and characterization of a gene that encodes a MYC-related protein in *Arabidopsis*," Plant Mol. Biol., 1996, 32:571-57.
Vij et al,, "Genome-wide analysis of the stress associated protein (SAP) gene family containing A20/AN1 zinc-finger(s) in rice and their phylogenetic relationship with *Arabidopsis*," Mol Genet Genomics, Dec. 2006;276(6):565-575.
Weigel et al., "Activation Tagging in *Arabidopsis*," Plant Physiology, Apr. 2000, 122:1003-1013.
Wood, et al. (2000) in Pilot Analysis of Global Ecosystems: Agroecosystems (Int. Food Policy Res, Inst. And World Resources Inst. Washington, DC), pp. 45-54.
Yamamoto et al., 'The Promoter of a Pine Photosynthetic Gene Allows Expression of a BGlucuronidase Reporter Gene in Tmnsgenic Rice Plants in a Light-Independent but Tissue-Specific Manner, Plant Cell Physiol, 1994;35(5):773-778.
Yan et al., "New Construct Approaches for Efficient Gene Silencing in Plants," Plant Physiol., Aug. 2006, 141:1508-1518.
Zhang et al., "DNA Sequences That Activate Isocitrate Lyase Gene Expression during Late Embryogenesis and during Postgerminative Growth," Plant Physiology, 1996, 110:1069-1079.

(56) References Cited

OTHER PUBLICATIONS

Zheng et al., "SPK1 Is an Essential S-Phase-Specific Gene of *Saccharomyces cerevisiae* That Encodes a Nuclear Serine/Threonine/Tyrosine Kinase," Mol. Cell Biol., Sep. 1993, 13:5829-5842.
*Zea mays* clone 219367 NAC domain-containing protein 67 mRNA, GenBank Accession No. EU959686.1, published Dec. 10, 2008.
Hu et al., 2006 PNAS 103(35): 12987-12992.
Nakashima et al., 2012 BBA 1819(2): 97-103.
Predicted *Zea mays* IQ-domain 3 protein, GenBank accession No. XM_008674184, published Dec. 18, 2017.
Fischer et al., "An IQ Domain Mediates the Interaction with Calmodulin in a Plant Cyclic Nucleotide-Gated Channel". Plant & Cell Physiology 54:573-584. 2013.
USPTO: Final Office Action regarding U.S. Appl. No. 15/881,091, dated May 10, 2019.
Response to Final Office Action regarding U.S. Appl. No. 15/881,091, dated Jun. 25, 2019.
USPTO: Advisory Action regarding U.S. Appl. No. 15/881,091, dated Jul. 11, 2019.

\* cited by examiner

| | | | | | | |
|---|---|---|---|---|---|---|
| SEQ_ID_NO_353 | EKL----- | EVPE | R-APLAHSMV | KKRLSFPVVE | KPSVVPTEKP | 474 |
| SEQ_ID_NO_355 | G------- | TITQE | NEGFTDKAISA | KKRLSYPITSP | AL-------- | 436 |
| SEQ_ID_NO_357 | NGA----- | ETPE | K-GG-STGPA | KKRLSFQGGT | AA-------- | 187 |
| SEQ_ID_NO_358 | DRF----- | EVPE | R-VPLVHSSI | KKRLSFPVAD | KPNGEHADKL | 476 |
| SEQ_ID_NO_360 | EGAAQA | ETLE | K-GWSSVGSA | KKRLSFPAGT | PPPPV----P | 348 |
| SEQ_ID_NO_362 | DNN----- | GTPD | A--SVGYM | KKRLSFSASP | A--------- | 292 |
| SEQ_ID_NO_364 | S------- | GTPD | R--VAGSA | KKRLLFPASP | A--------- | 443 |

| | | | | | | |
|---|---|---|---|---|---|---|
| SEQ_ID_NO_353 | RERVRRHSDP | PKVDPATLK- | ---------- | ---------- | D-APAA | 498 |
| SEQ_ID_NO_355 | -PKPRRESAP | PKVESGGVT- | ---------- | ---VT----- | N-GAGS | 461 |
| SEQ_ID_NO_357 | ASPMRRHSGP | PKVEIAPPQP | ---------- | ---MV----- | N-GGSK | 217 |
| SEQ_ID_NO_358 | MERGRRHSGP | PKVDPASLK- | ---------- | ---------- | D-VPVS | 500 |
| SEQ_ID_NO_360 | AAARRHSGP | PKVRQAGVEG | EAL------- | ------ER-- | DL-SSLA | 378 |
| SEQ_ID_NO_362 | --GARRHSGP | PRVDASAVKD | GTE------- | IQMHREEKMS | NG-ASSK | 326 |
| SEQ_ID_NO_364 | --SSRRHSEP | PKVDISEARK | NQH------- | ---APS---- | NGRQVAW | 474 |

FIGURE 1D

| | | | | | |
|---|---|---|---|---|---|
| SEQ_ID_NO_237 | MAQRTEK- -E | -TEFK- -VLE | -TL- -T- | TNNCGVTANP | 36 |
| SEQ_ID_NO_239 | MAQRTEK- -E | -TEFK- -VPE | -TL- | VNNCGVTGNP | 31 |
| SEQ_ID_NO_241 | MAQRDKKVE-E | P- -TELR-APE | -L- | ANSCGFPGNP | 32 |
| SEQ_ID_NO_243 | MAQRDKK- -E | EPTELR-APE | -TL- | ANNCGFPGNP | 31 |
| SEQ_ID_NO_245 | MAQKTEK- -E | -TEFK- -APE | -TL-P- | SNNCGVTANP | 35 |
| SEQ_ID_NO_246 | MAQKTEK- -E | -TEFK- -VLE | -TL- | VNNCGFTGNP | 31 |
| SEQ_ID_NO_248 | MAQRTEK- -E | -TDFK- -VPE | -AL- | VNNCGVTGNP | 31 |
| SEQ_ID_NO_250 | MAQRTEK- -E | -TECK- -VPE | -TL- | INNCGVTGNP | 31 |
| SEQ_ID_NO_251 | MAQRTEK- -E | -TEFK-AVPE | -TL-TT- | INNCGFTGNP | 32 |
| SEQ_ID_NO_253 | MAQRD- -K- -E | -TEMK- -VSE | -NL- | INNCGV-VGAP | 32 |
| SEQ_ID_NO_255 | MAQRE-EK- -E | -AKLH- -APE | -TL- | VNNCGFSGNP | 30 |
| SEQ_ID_NO_257 | MAQRDKK- -E | EPTELR-APE | -SL- | VNNCGFPGNP | 30 |
| SEQ_ID_NO_258 | MAQRDKK- -E | EPTELR-APE | -TL- | ANGCGFPGNP | 31 |

| | | | | | |
|---|---|---|---|---|---|
| SEQ_ID_NO_237 | ATNNMCQKCF | NASLVSAAAG | VVESGSILL | - - - - - - - - - | 64 |
| SEQ_ID_NO_239 | ATNNMCQKCF | SATTAATSS- | SSSSSSTN- | -N- -TATSA- | 64 |
| SEQ_ID_NO_241 | ATNNLCQACF | QAATASSAS- | ASMSPPSP- | SS-LSPSPLA | 68 |
| SEQ_ID_NO_243 | ATONLCQSCF | SAATASMSS- | SPTSSSSS- | S-TAPAP- | 64 |
| SEQ_ID_NO_245 | ATNNMCQKCF | NASVAAAGV- | DSTSIL- | - - - - - - - - - | 60 |
| SEQ_ID_NO_246 | ATNNMCQKCF | SASASAAAA- | AAAGALKS- | SH-KVSG- | 64 |
| SEQ_ID_NO_248 | ATNNMCQKCF | TAETTSLAT- | TSGAGGAG- | I-A- | 60 |
| SEQ_ID_NO_250 | ATNNMCQNCF | NATTTNGVS- | TNEIL-KE- | - - - - - - - - - | 57 |
| SEQ_ID_NO_251 | ATNNMCQKCF | NATTAATST- | SSSSPTGT- | SV-T-PHNFA | 68 |
| SEQ_ID_NO_253 | ATNNMCQNCF | LATTSHRT- | - - - - - - - - | - - - - - - - - - | 51 |
| SEQ_ID_NO_255 | ATKNMCQSCY | KISTGMTQ- | PALTFSG- | - - - - - - - - - | 56 |
| SEQ_ID_NO_257 | ATNNMCQSCF | QASLAASP- | APHSC- | - - - - - - - - - | 54 |
| SEQ_ID_NO_258 | ATQNLCQNCE | SAASASTSS- | PPSPSSS- | - - - - - - - - - | 57 |

| | | | | | |
|---|---|---|---|---|---|
| SEQ_ID_NO_237 | KKRDQQLVNR | CSGCRKKVGL | TGFRCRCGEL | FCSEHRYSDR | 130 |
| SEQ_ID_NO_239 | DTAEKKSVNR | CSGCRKRVGL | TGFRCRCGEL | FCSDHRYSDR | 150 |
| SEQ_ID_NO_241 | STSSSSSVNR | CQSCRKRVGL | TGFRCRCGEL | FCGAHRYSDR | 146 |
| SEQ_ID_NO_243 | KAPARTSANR | CSSCRKRVGL | TGFRCRCGDL | FCAEHRYSDR | 133 |
| SEQ_ID_NO_245 | -KRDQQTINR | CSGCRRKVGL | TGFRCRCGDL | FCAEHRYTDR | 125 |
| SEQ_ID_NO_246 | DSLVKREVNR | CSGCRRKVGL | TGFRCRCGEL | FCMEHRYSDR | 120 |
| SEQ_ID_NO_248 | PSEAKRVVNR | CSGCRRRVGL | TGFRCRCGDL | FCGEHRYSDR | 134 |
| SEQ_ID_NO_250 | SSVAKKEVNR | CSGCRKRVGL | TGFRCRCGEL | FCGEHRYSDR | 130 |
| SEQ_ID_NO_251 | LPPAKREVNR | CSGCRKRVGL | TGFRCRCGEL | YCSEHRYSDR | 158 |
| SEQ_ID_NO_253 | VVVKKEVSR | CSGCRKRVGL | TGFRCRCGDL | FCSEHRYSDR | 126 |
| SEQ_ID_NO_255 | IVEKKQEVNR | CFSCRKRVGL | TGFRCRCGDM | FCGEHRYSDR | 140 |
| SEQ_ID_NO_257 | APAPARQVSR | CSSCRKRVGL | TGFRCRCGEL | FCGEHRYSDR | 125 |
| SEQ_ID_NO_258 | VKAGKTSVNR | | TGFRCRCGEL | FCGEHRYSDR | 135 |

| | | | | |
|---|---|---|---|---|
| SEQ_ID_NO_237 | HDCSYDYKTA | GREAIARENP | VVKAAKMVKV | 160 |
| SEQ_ID_NO_239 | DCSYDYKAA | GREAIARENP | VVKAAKI-RV | 180 |
| SEQ_ID_NO_241 | HDCQFDYKAV | GRDAIARENP | VVRAAKIVRF | 176 |
| SEQ_ID_NO_243 | HGCSYDYKGA | ARDAIARENP | VVRAAKIVRF | 163 |
| SEQ_ID_NO_245 | HDCSYDYKTA | GREAIARENP | VVKAAKIVKV | 155 |
| SEQ_ID_NO_246 | HECSYDYKAA | GREAIARENP | VVKAAKIVRV | 150 |
| SEQ_ID_NO_248 | HDCSYDYKAA | GREAIARENP | VIRAAKIVKV | 164 |
| SEQ_ID_NO_250 | HDCSYDYKTV | GREAIARENP | VVKAAKIVRV | 160 |
| SEQ_ID_NO_251 | HDCSYDYKTA | GREAIARENP | VVKAAKI-KV | 188 |
| SEQ_ID_NO_253 | HDCSYDYKAV | GREMIARDNP | VVKAAKIVRI | 156 |
| SEQ_ID_NO_255 | HDCSFDYKAA | GRESIARQNP | VVKAAKI-RL | 170 |
| SEQ_ID_NO_257 | HDCSYDYKAA | ARVAIARANP | VVRAAKIVRV | 155 |
| SEQ_ID_NO_258 | HGCSYDYKAA | TRDAIARDNP | VVRAAKIVRF | 165 |

| | | | | |
|---|---|---|---|---|
| SEQ_ID_NO_451 | TTFCGSHRYP | EMHGCTFDFK | SAGREEIAKA | NPLVIAAKLQ | 159 |
| SEQ_ID_NO_453 | VTFCGSHRYP | ENHGCTFDFK | KVGREEIARA | NPLVKAGKLE | 159 |
| SEQ_ID_NO_454 | ITFCGVHRYP | EQHGCTFDFK | TLGKEAISKA | NPVVKAEKLH | 159 |
| SEQ_ID_NO_456 | TTFCGSHRYP | EKHACGFDFK | AVGREEIARA | NPVIKGEKLR | 162 |
| SEQ_ID_NO_457 | SMFCGAHRYP | EKHINCTFDFK | KIGREEIARE | NPLVAQKLH | 164 |
| SEQ_ID_NO_458 | VTFCGSFDFK | EKHACSFDFK | TVGREAIARA | NPVVKAEKLR | 163 |
| SEQ_ID_NO_459 | TTFCGTHRYP | EIHGCSFDFK | SIGKEAIAKA | NPVVKAKKLL | 155 |
| SEQ_ID_NO_460 | MVFCGTHRYP | EQHDCEFDFK | SLGKEQIAKA | NPVVRAEKLR | 157 |
| SEQ_ID_NO_461 | MTFCGTHRYP | EQHACGFDFR | GMGKEQIAKA | NPVVKGEKLQ | 160 |
| SEQ_ID_NO_462 | TTFCGTHRYP | EIHGCSFDFK | SIGREAIAKA | NPVVKADKLQ | 149 |
| SEQ_ID_NO_463 | NTFCGLHRYA | EKHSCSFDFK | AAGREAIARA | NPE | 179 |
| SEQ_ID_NO_465 | AIYCGVHRYA | EQHDCTFDFK | AAGRATIARA | NPVVKADKLH | 145 |
| SEQ_ID_NO_467 | DTFCSTHRYT | DSHQCTFDYK | KVAREQIAKQ | NPVVMAEKIN | 161 |
| SEQ_ID_NO_468 | NLYCAMHRYS | DKHDCQFDYR | TAARDAIAKA | NPVVKAEKLD | 169 |
| SEQ_ID_NO_469 | GTFCSLHRYT | DSHECTFDYK | KVAREQIAKQ | NPVVIAEKIN | 157 |

| | | |
|---|---|---|
| SEQ_ID_NO_451 | KI | 161 |
| SEQ_ID_NO_453 | KI | 161 |
| SEQ_ID_NO_454 | KI | 161 |
| SEQ_ID_NO_456 | RI | 164 |
| SEQ_ID_NO_457 | KI | 166 |
| SEQ_ID_NO_458 | RI | 165 |
| SEQ_ID_NO_459 | -G | 156 |
| SEQ_ID_NO_460 | | 159 |
| SEQ_ID_NO_461 | RI | 162 |
| SEQ_ID_NO_462 | KL | 149 |
| SEQ_ID_NO_463 | -- | 181 |
| SEQ_ID_NO_465 | KL | 147 |
| SEQ_ID_NO_467 | KI | 163 |
| SEQ_ID_NO_468 | KI | 171 |
| SEQ_ID_NO_469 | KI | 159 |

FIGURE 3C

| SEQ_ID_NO_2 | - - - - - - - - M V - - - - - | - - - - - A M Q Q Q Q Q A Q | R R D A E A E L N L | P P G F R F H P T D | 24 |
|---|---|---|---|---|---|
| SEQ_ID_NO_3 | - - - - - - - M V A M A - - - | - - - - - - - - - - - - - A | R R D A E A E L N L | P P G F R F H P T D | 34 |
| SEQ_ID_NO_4 | - - - - - - - M V M T T - - - | - - - - - - A Q Q Q | R R D A E A E L N L | P P G F R F H P T D | 30 |
| SEQ_ID_NO_5 | - - - - - - - M V M A - - - - | - - - - - - - - - - - - - A A E | R R D A E A E L N L | P P G F R F H P T D | 27 |
| SEQ_ID_NO_7 | - - - - - - - M G M G - - - - | - - - - - - - - - - - - M R R | E R D A E A E L N L | P P G F R F H P T D | 27 |
| SEQ_ID_NO_8 | - - - - - - - M G I - - - - - | - - - - - - - - - - - - - S R | R R D A E A E L N L | P P G F R F H P T D | 24 |
| SEQ_ID_NO_9 | - - - M M T A M V K A E A | M T A E A E G S S G | E R D A E A E L N L | P P G F R F H P T D | 40 |
| SEQ_ID_NO_10 | - - - - - - - - M K - - - - - | - - - - - - - - - - - - - - R | R T A D A E A N L | P P G F R F H P T D | 23 |
| SEQ_ID_NO_11 | - - - - - - - - M G - - - - - | - - - - - - - - - - - R R | T A D A E A Q L N L | P P G F R F E P T D | 24 |
| SEQ_ID_NO_12 | - - - - - - - - M - - - - - - | - - - - - - - - - - - - - G | R P N A E A Q L N L | P P G F R F H P T D | 22 |
| SEQ_ID_NO_13 | - - - - - - - - M - - - - - - | - - - - - - - - - - - - - - - | S S S D L Q L | P P G F R F H P T D | 18 |
| SEQ_ID_NO_14 | - - - - - - - - M - - - - - - | - - - - - - - - - - - - - - - | T T A E L Q L | P P G F R F H P T D | 18 |
| SEQ_ID_NO_15 | - - - - - - - - M - - - - - - | - - - - - - - - - - - - - - - | K G G D Q Q L N L | P A G F R F H P T D | 20 |

| SEQ_ID_NO_2 | E E L V A H Y L C A | R A A G R G P P V P | I A E V D L Y R F | D P W D L P E R A L | 64 |
|---|---|---|---|---|---|
| SEQ_ID_NO_3 | E E L V A H Y L C A | R A A G R R P P V S | I A E V D L Y R F | D P W D L P E R A L | 74 |
| SEQ_ID_NO_4 | E E L V A H Y L C A | R A A G R R P P V S | I A E V D L Y R F | D P W D L P E R A L | 70 |
| SEQ_ID_NO_5 | E E L V A D Y L C A | R A A G R A P P V P | I A E L D L Y R F | D P W E L P E R A L | 67 |
| SEQ_ID_NO_7 | D E L V E H Y L C R | K A A G Q R L P V P | I A E V D L Y K F | D P W D L P E K A L | 67 |
| SEQ_ID_NO_8 | E E L V V H Y L C K | K V A C Q R L P V P | I A E V D L Y K Y | D P W D L P E K A L | 64 |
| SEQ_ID_NO_9 | D E L V V H Y L C R | K V A G Q P P V P | I M E I D L Y K Y | N P W Q L P E K A L | 80 |
| SEQ_ID_NO_10 | E E L V V H Y L C R | K A S Y Q I T L P V P | A E V D L Y K Y | Y P W Q L P E K A L | 63 |
| SEQ_ID_NO_11 | D E L V V H Y L C R | K L L S Q R L P A A | I A E V D L Y K Y | D P W D L P E K A L | 64 |
| SEQ_ID_NO_12 | E E L V V H Y L C R | K C A S Q A I A V P | I A E I D L Y K F | D P W Q L P E K A L | 62 |
| SEQ_ID_NO_13 | E E L V M H Y L C R | K C S S Q P I S V P | I A E I D L Y K Y | D P W D L P G L A L | 58 |
| SEQ_ID_NO_14 | E E L V V H Y L C R | K C A S Q P I A V P | I A E I D L Y K Y | N P W D L P D L A L | 58 |
| SEQ_ID_NO_15 | E E L V V H Y L C R | K C A G Q Q I G V P | V I A E I D L Y K F | D P W E L P D L A L | 60 |

FIGURE 4A

| | | | | | | |
|---|---|---|---|---|---|---|
| SEQ_ID_NO_2 | FGRREWYFFT | PRDRKYPNGS | RPNRAAGTGY | MKATGADKPV | | 104 |
| SEQ_ID_NO_3 | FGRREWYFFT | PRDRKYPNGS | RPNRAAGSGY | MKATGADKPV | | 114 |
| SEQ_ID_NO_4 | FGRREWYFFT | PRDRKYPNGS | RPNRAAGSGY | MKATGADKPV | | 110 |
| SEQ_ID_NO_5 | FGAREWYFFT | PRDRKYPNGS | RPNRAAGGY | MKATGADRPV | | 107 |
| SEQ_ID_NO_7 | FGLKEWYFFT | PRDRKYPNGS | RPNRAAGNGY | MKATGADKPV | | 107 |
| SEQ_ID_NO_8 | FGSREWYFFT | PRDRKYPNGS | RPNRSAGTGY | MKATGADKPV | | 104 |
| SEQ_ID_NO_9 | FGIKEWYFFT | PRDRKYPNGS | RPNRAAGNGY | MKATGADKPV | | 120 |
| SEQ_ID_NO_10 | FGHKEWYFLT | PRDRKYPNGS | RPNRAAGRGY | MKATGADKPI | | 103 |
| SEQ_ID_NO_11 | FGEKEWYFFT | PRDRKYPNGS | RPNRAAGRGY | MKATGADKPI | | 104 |
| SEQ_ID_NO_12 | FGEKEWYFFT | PRDRKYPNGS | RPNRAAGSGY | MKATGADKPI | | 102 |
| SEQ_ID_NO_13 | YGEKEWYFFS | PRDRKYPNGS | RPNRAAGTGY | MKATGADKPI | | 98 |
| SEQ_ID_NO_14 | YGEKEWYFFS | PRDRKYPNGS | RPNRAAGTGY | MKATGADKPI | | 98 |
| SEQ_ID_NO_15 | YGEKEWYFFS | PRDRKYPNGS | RPNRAAGTGY | MKATGADKPV | | 100 |

| | | | | | | |
|---|---|---|---|---|---|---|
| SEQ_ID_NO_2 | HHA--- | GRTL- | GI KKALVFYH | GKPPRGVKTE | MI MHEYRLAD | 141 |
| SEQ_ID_NO_3 | EHE--- | GRTA- | GI KKALVFYH | GKPPRGVKTE | MI MHEYRLAE | 151 |
| SEQ_ID_NO_4 | EHR--- | GRTV- | GI KKALVFYH | GKPPRGVKTE | MI MHEYRLAG | 147 |
| SEQ_ID_NO_5 | ARA--- | GRTV- | GI KKALVFYD | GRPSAGVKTD | MI MHEYRLAD | 144 |
| SEQ_ID_NO_7 | APR--- | GRTL- | GI KKALVFYS | GKAPRGVKTD | MI MHEYRLAD | 144 |
| SEQ_ID_NO_8 | TPKG- | SSRPL | GI KKALVFYS | GRAPRGVKTD | MI MHEYRI AQ | 143 |
| SEQ_ID_NO_9 | APRES | GGRTV | GI KKALVFYS | GKAPKGTKTD | MI MHEYRLAD | 160 |
| SEQ_ID_NO_10 | RPTG- | STKAV | GI KKALVFYV | GKAPRGTKTN | MI MHEYRLAQ | 142 |
| SEQ_ID_NO_11 | APKGGS | SKPL | GI KKALVFYA | GKAPKGNKTN | MI MHEYRLAD | 144 |
| SEQ_ID_NO_12 | TAKG- | SNKRV | GI KKALVFYA | GKAPRGEKTN | MI MHEYRLAD | 141 |
| SEQ_ID_NO_13 | GS--- | PKPV | GI KKALVFYA | GKAPKGEKTN | MI MHEYRLAD | 134 |
| SEQ_ID_NO_14 | GH--- | PKAV | GI KKALVFYA | GKAPKGEKTN | MI MHEYRLAD | 134 |
| SEQ_ID_NO_15 | GK--- | PKTL | GI KKALVFYA | GKAPRGVKTN | MI MHEYRLAN | 136 |

| | | | | | |
|---|---|---|---|---|---|
| SEQ_ID_NO_2  | -PESEI | DDD- | T- | FPML GLLP | EFDDMG- PA- | 222 |
| SEQ_ID_NO_3  | -PESEI | DDD- | P- | FPEL GSLP | AEDDMG- AA- | 236 |
| SEQ_ID_NO_4  | -PESEI | DDD- | P- | FPEL ASLP | ALDDMV- GL- | 228 |
| SEQ_ID_NO_5  | -PESDV | DND- | P- | FPEL DSLP | EFQTA- | 224 |
| SEQ_ID_NO_7  | -PESEI | DND- | P- | FPEL DSFP | AFQ- | 228 |
| SEQ_ID_NO_8  | -PESDI | VDND- | B- | VMEPDFDD- | MA- QV- | 220 |
| SEQ_ID_NO_9  | HDSSEI | DNA- | S- | GLQQ- QHH | GEMDMA- QR- | 247 |
| SEQ_ID_NO_10 | -PESDI | DLE- | T- | LSYNHDL | HGA QG- | 224 |
| SEQ_ID_NO_11 | -P-DL | EHE- | P- | YPEFEED- | LA- KP- | 220 |
| SEQ_ID_NO_12 | PGI L- | | | | MNS | 219 |
| SEQ_ID_NO_13 | PENLA- | | | | NTI SI EHSERTSQ | 196 |
| SEQ_ID_NO_14 | PEI LP- | | | | | 195 |
| SEQ_ID_NO_15 | PEVDA- | F | B- | TG- | DMV- | 198 |

| | | | | | |
|---|---|---|---|---|---|
| SEQ_ID_NO_2  | | | EG- | MP- | 226 |
| SEQ_ID_NO_3  | | | | | 236 |
| SEQ_ID_NO_4  | | | | | 228 |
| SEQ_ID_NO_5  | | | | | 224 |
| SEQ_ID_NO_7  | PIALA- | | | | 228 |
| SEQ_ID_NO_8  | | | | | 224 |
| SEQ_ID_NO_9  | | | | | 247 |
| SEQ_ID_NO_10 | | | | | 228 |
| SEQ_ID_NO_11 | GAHP- | | | | 224 |
| SEQ_ID_NO_12 | QGYS- TVYP- DSTI SAPSPN | CRTASNHDSR | ASAI TSLSYN | SNPI FEQNLN | 259 |
| SEQ_ID_NO_13 | CP- | | | | 198 |
| SEQ_ID_NO_14 | PLP- | | | | 198 |
| SEQ_ID_NO_15 | GPAP- | | | | 202 |

TRANSGENIC PLANTS HAVING INCREASED TOLERANCE TO ALUMINUM

CROSS-REFERENCE TO RELATED APPLICATION

This application claims priority to U.S. Application Ser. No. 61/554,788, filed on Nov. 2, 2011, entitled TRANSGENIC PLANTS HAVING INCREASED TOLERANCE TO ALUMINUM, the disclosure of which is incorporated herein by reference.

TECHNICAL FIELD

This document relates to methods and materials involved in modulating tolerance to abiotic stress in plants. For example, this document provides plants having increased aluminum tolerance, materials and methods for making plants having increased aluminum tolerance, as well as methods of increasing plant yield in soil containing elevated levels of aluminum.

INCORPORATION-BY-REFERENCE OF SEQUENCE LISTING

The material in the accompanying sequence listing is hereby incorporated by reference into this application. The accompanying file, named Sequence_Listing_2012-10-30.txt was created on Oct. 30, 2012, and is 1.69 MB. The file can be accessed using Microsoft Word on a computer that uses Windows OS.

BACKGROUND

Aluminum (Al) is ubiquitous in soils and at pH values below 5.0, is solubilized into the soil solution as the highly phytotoxic $Al^{3+}$ species, which inhibits root growth and damages root systems (Kochian, 1995, *Annu. Rev. Plant Biol.* 46: 237-260). As such, aluminum toxicity is aggravated by acid precipitation (e.g., acid rain). For example, contaminated soils in Brazil contain aluminum in amounts that range from 11 to 124 g/Kg of soil. Another constraint on acid soils is phosphorous (P) deficiency, which is caused by P fixation with Al and Fe oxides on the surface of clay minerals in acid soils. See Sanchez et al. 1997. In: Replenishing Soil Fertility in Africa, ed. R Buresh, P Sanchez, F Calhoun, pp. 1-46). Root damage reduces water and nutrient uptake and thus crop productivity. Low soil pH has been documented to reduce the yield on nearly 25% of the world's land presently under production. See, Wood, et al. (2000) in Pilot Analysis of Global Ecosystems: Agroecosystems (Int. Food Policy Res, Inst. And World Resources Inst., Washington, D.C.), pp 45-54). Thus, there is a need to provide methods and materials for increasing aluminum tolerance in plants.

SUMMARY

This document provides methods and materials related to plants having increased tolerance to aluminum ($Al^{3+}$). For example, this document provides transgenic plants and plant cells having increased tolerance to aluminum, nucleic acids used to generate transgenic plants and plant cells having increased tolerance to aluminum, methods for making plants having increased tolerance to aluminum, and methods for making plant cells that can be used to generate plants having increased tolerance to aluminum. Such plants and plant cells can be grown in acidic soils containing elevated levels of $Al^{3+}$, resulting in increased yield in such soils.

In one aspect, this document features a method of increasing plant yield in soil containing elevated levels of $Al^{3+}$. The method includes growing a plant comprising an exogenous nucleic acid on soil having an elevated level of $Al^{3+}$, wherein yield of the plant is increased as compared to the corresponding yield of a control plant that does not comprise said nucleic acid.

In some embodiments, the exogenous nucleic acid includes a regulatory region operably linked to a nucleotide sequence encoding a polypeptide, wherein the HMM bit score of the amino acid sequence of the polypeptide is greater than about 65, the HMM based on the amino acid sequences depicted in any one of FIGS. 1-4.

In some embodiments, the exogenous nucleic acid includes a regulatory region operably linked to a nucleotide sequence encoding a polypeptide having 90 percent or greater sequence identity to an amino acid sequence set forth in SEQ ID NOs: 2, 3, 4, 5, 7, 8, 9, 10, 11, 12, 13, 14, 15, 17, 19, 20, 22, 24, 26, 28, 29, 31, 32, 33, 35, 36, 38, 40, 41, 42, 43, 44, 45, 47, 48, 49, 50, 52, 54, 55, 56, 57, 58, 59, 61, 63, 64, 65, 66, 67, 69, 70, 72, 73, 75, 77, 78, 79, 81, 82, 83, 84, 85, 86, 87, 88, 89, 90, 91, 93, 94, 96, 97, 98, 99, 100, 102, 103, 104, 105, 106, 107, 108, 109, 110, 111, 113, 115, 117, 119, 120, 121, 122, 124, 125, 126, 127, 129, 131, 132, 134, 136, 137, 138, 140, 142, 144, 146, 147, 148, 149, 150, 151, 152, 153, 154, 155, 156, 158, 159, 160, 162, 163, 164, 166, 167, 169, 171, 172, 173, 174, 175, 176, 177, 178, 179, 180, 181, 182, 183, 184, 185, 186, 187, 188, 190, 191, 192, 193, 194, 195, 197, 198, 199, 200, 201, 202, 203, 205, 207, 209, 211, 212, 213, 214, 215, 216, 217, 218, 219, 220, 221, 223, 224, 225, 227, 228, 229, 230, 231, 232, 233, 234, 235, 237, 239, 241, 243, 245, 246, 248, 250, 251, 253, 255, 257, 258, 259, 261, 263, 265, 267, 269, 271, 273, 274, 276, 278, 280, 281, 283, 284, 285, 287, 288, 290, 292, 293, 294, 296, 298, 300, 302, 304, 306, 308, 310, 312, 314, 316, 318, 320, 322, 324, 326, 328, 329, 331, 333, 335, 337, 338, 339, 341, 342, 343, 344, 345, 346, 347, 348, 349, 350, 351, 353, 355, 357, 358, 360, 362, 364, 366, 368, 369, 371, 373, 375, 376, 377, 378, 379, 380, 382, 384, 386, 388, 390, 392, 393, 395, 396, 397, 398, 399, 400, 401, 402, 404, 405, 407, 409, 411, 413, 414, 416, 418, 420, 421, 423, 424, 425, 426, 428, 429, 431, 432, 433, 434, 435, 436, 437, 438, 439, 440, 441, 442, 443, 444, 445, 446, 447, 449, 451, 453, 454, 456, 457, 458, 459, 460, 461, 462, 463, 465, 467, 468, 469, 470, 471, 472, 473, 474, 475, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 535, 537, 539, 540, 542, 544, 545, 547, 549, 551, 553, 555, 557, 558, 560, 562, 564, 568, 570, 572, 574, 576, 578, 579, 580, 581, 583, 585, 587, 589, 591, 593, 595, 597, 599, 601, 603, 605, 607, 608, 610, 612, 614, 616, 618, 620, 622, 624, 625, 627, 629, 631, 633, 635, 637, 639, 641, 643, 645, 647, 649, 650, 651, 652, 653, 654, 655, 656, 657, 658, 660, 662, 664, 666, 668, 669, 670, 671, 672, 673, 674, 675, 676, 677, 679, 681, 683, 685, 686, 687, 689, 691, 693, 695, 696, 698, 699, 701, 702, 703, 704, 705, 706, 707, 709, 710, 711, 712, 713, 714, 715, 716, 717, 718, 719, 721, 722, 723, 724, 725, 726, 727, 728, 729, 730, 731, 732, 733, 734, 735, 736, 737, 738, 739, 740, 742, 744, 745, 746, 747, 749, 750, 752, 753, 754, 755, 757, 759, 760, 761, 762, 764, 765, 766, 767, 768, 769, 770, 771, and 772.

In some embodiments, the exogenous nucleic acid includes a regulatory region operably linked to a nucleotide sequence having 90 percent or greater sequence identity to the nucleotide sequence set forth in SEQ ID NOs: 1, 6, 16, 18, 21, 23, 25, 27, 30, 34, 37, 39, 46, 51, 53, 60, 62, 68, 71, 74, 76, 80, 92, 95, 101, 112, 114, 116, 118, 123, 128, 130, 133, 135, 139, 141, 143, 145, 157, 161, 165, 168, 170, 189, 196, 204, 206, 208, 210, 222, 226, 236, 238, 240, 242, 244, 247, 249, 252, 254, 256, 260, 262, 264, 266, 268, 270, 272, 275, 277, 279, 282, 286, 289, 291, 295, 297, 299, 301, 303, 305, 307, 309, 311, 313, 315, 317, 319, 321, 323, 325, 327, 330, 332, 334, 336, 340, 352, 354, 356, 359, 361, 363, 365, 367, 370, 372, 374, 381, 383, 385, 387, 389, 391, 394, 403, 406, 408, 410, 412, 415, 417, 419, 422, 427, 430, 448, 450, 452, 455, 464, 466, 477, 479, 481, 483, 485, 487, 489, 491, 493, 495, 497, 499, 501, 503, 505, 507, 509, 511, 513, 515, 517, 519, 521, 523, 525, 527, 529, 531, 533, 536, 538, 541, 543, 546, 548, 550, 552, 554, 556, 559, 561, 563, 567, 569, 571, 573, 575, 577, 582, 584, 586, 588, 590, 592, 594, 596, 598, 600, 602, 604, 606, 609, 611, 613, 615, 617, 619, 621, 623, 626, 628, 630, 632, 634, 636, 638, 640, 642, 644, 646, 648, 659, 661, 663, 665, 667, 678, 680, 682, 684, 688, 690, 692, 694, 697, 700, 708, 720, 741, 743, 748, 751, 756, 758, and 763.

In any of the methods described herein, the nucleotide sequence can encode a polypeptide having 95 percent or greater sequence identity to the amino acid sequence set forth in SEQ ID NOs: 2, 3, 4, 5, 7, 8, 9, 10, 11, 12, 13, 14, 15, 17, 19, 20, 22, 24, 26, 28, 29, 31, 32, 33, 35, 36, 38, 40, 41, 42, 43, 44, 45, 47, 48, 49, 50, 52, 54, 55, 56, 57, 58, 59, 61, 63, 64, 65, 66, 67, 69, 70, 72, 73, 75, 77, 78, 79, 81, 82, 83, 84, 85, 86, 87, 88, 89, 90, 91, 93, 94, 96, 97, 98, 99, 100, 102, 103, 104, 105, 106, 107, 108, 109, 110, 111, 113, 115, 117, 119, 120, 121, 122, 124, 125, 126, 127, 129, 131, 132, 134, 136, 137, 138, 140, 142, 144, 146, 147, 148, 149, 150, 151, 152, 153, 154, 155, 156, 158, 159, 160, 162, 163, 164, 166, 167, 169, 171, 172, 173, 174, 175, 176, 177, 178, 179, 180, 181, 182, 183, 184, 185, 186, 187, 188, 190, 191, 192, 193, 194, 195, 197, 198, 199, 200, 201, 202, 203, 205, 207, 209, 211, 212, 213, 214, 215, 216, 217, 218, 219, 220, 221, 223, 224, 225, 227, 228, 229, 230, 231, 232, 233, 234, 235, 237, 239, 241, 243, 245, 246, 248, 250, 251, 253, 255, 257, 258, 259, 261, 263, 265, 267, 269, 271, 273, 274, 276, 278, 280, 281, 283, 284, 285, 287, 288, 290, 292, 293, 294, 296, 298, 300, 302, 304, 306, 308, 310, 312, 314, 316, 318, 320, 322, 324, 326, 328, 329, 331, 333, 335, 337, 338, 339, 341, 342, 343, 344, 345, 346, 347, 348, 349, 350, 351, 353, 355, 357, 358, 360, 362, 364, 366, 368, 369, 371, 373, 375, 376, 377, 378, 379, 380, 382, 384, 386, 388, 390, 392, 393, 395, 396, 397, 398, 399, 400, 401, 402, 404, 405, 407, 409, 411, 413, 414, 416, 418, 420, 421, 423, 424, 425, 426, 428, 429, 431, 432, 433, 434, 435, 436, 437, 438, 439, 440, 441, 442, 443, 444, 445, 446, 447, 449, 451, 453, 454, 456, 457, 458, 459, 460, 461, 462, 463, 465, 467, 468, 469, 470, 471, 472, 473, 474, 475, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 535, 537, 539, 540, 542, 544, 545, 547, 549, 551, 553, 555, 557, 558, 560, 562, 564, 568, 570, 572, 574, 576, 578, 579, 580, 581, 583, 585, 587, 589, 591, 593, 595, 597, 599, 601, 603, 605, 607, 608, 610, 612, 614, 616, 618, 620, 622, 624, 625, 627, 629, 631, 633, 635, 637, 639, 641, 643, 645, 647, 649, 650, 651, 652, 653, 654, 655, 656, 657, 658, 660, 662, 664, 666, 668, 669, 670, 671, 672, 673, 674, 675, 676, 677, 679, 681, 683, 685, 686, 687, 689, 691, 693, 695, 696, 698, 699, 701, 702, 703, 704, 705, 706, 707, 709, 710, 711, 712, 713, 714, 715, 716, 717, 718, 719, 721, 722, 723, 724, 725, 726, 727, 728, 729, 730, 731, 732, 733, 734, 735, 736, 737, 738, 739, 740, 742, 744, 745, 746, 747, 749, 750, 752, 753, 754, 755, 757, 759, 760, 761, 762, 764, 765, 766, 767, 768, 769, 770, 771, and 772.

In any of the methods described herein, the nucleotide sequence can encode a polypeptide having 98 percent or greater sequence identity to the amino acid sequence set forth in SEQ ID NOs: 2, 3, 4, 5, 7, 8, 9, 10, 11, 12, 13, 14, 15, 17, 19, 20, 22, 24, 26, 28, 29, 31, 32, 33, 35, 36, 38, 40, 41, 42, 43, 44, 45, 47, 48, 49, 50, 52, 54, 55, 56, 57, 58, 59, 61, 63, 64, 65, 66, 67, 69, 70, 72, 73, 75, 77, 78, 79, 81, 82, 83, 84, 85, 86, 87, 88, 89, 90, 91, 93, 94, 96, 97, 98, 99, 100, 102, 103, 104, 105, 106, 107, 108, 109, 110, 111, 113, 115, 117, 119, 120, 121, 122, 124, 125, 126, 127, 129, 131, 132, 134, 136, 137, 138, 140, 142, 144, 146, 147, 148, 149, 150, 151, 152, 153, 154, 155, 156, 158, 159, 160, 162, 163, 164, 166, 167, 169, 171, 172, 173, 174, 175, 176, 177, 178, 179, 180, 181, 182, 183, 184, 185, 186, 187, 188, 190, 191, 192, 193, 194, 195, 197, 198, 199, 200, 201, 202, 203, 205, 207, 209, 211, 212, 213, 214, 215, 216, 217, 218, 219, 220, 221, 223, 224, 225, 227, 228, 229, 230, 231, 232, 233, 234, 235, 237, 239, 241, 243, 245, 246, 248, 250, 251, 253, 255, 257, 258, 259, 261, 263, 265, 267, 269, 271, 273, 274, 276, 278, 280, 281, 283, 284, 285, 287, 288, 290, 292, 293, 294, 296, 298, 300, 302, 304, 306, 308, 310, 312, 314, 316, 318, 320, 322, 324, 326, 328, 329, 331, 333, 335, 337, 338, 339, 341, 342, 343, 344, 345, 346, 347, 348, 349, 350, 351, 353, 355, 357, 358, 360, 362, 364, 366, 368, 369, 371, 373, 375, 376, 377, 378, 379, 380, 382, 384, 386, 388, 390, 392, 393, 395, 396, 397, 398, 399, 400, 401, 402, 404, 405, 407, 409, 411, 413, 414, 416, 418, 420, 421, 423, 424, 425, 426, 428, 429, 431, 432, 433, 434, 435, 436, 437, 438, 439, 440, 441, 442, 443, 444, 445, 446, 447, 449, 451, 453, 454, 456, 457, 458, 459, 460, 461, 462, 463, 465, 467, 468, 469, 470, 471, 472, 473, 474, 475, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 535, 537, 539, 540, 542, 544, 545, 547, 549, 551, 553, 555, 557, 558, 560, 562, 564, 568, 570, 572, 574, 576, 578, 579, 580, 581, 583, 585, 587, 589, 591, 593, 595, 597, 599, 601, 603, 605, 607, 608, 610, 612, 614, 616, 618, 620, 622, 624, 625, 627, 629, 631, 633, 635, 637, 639, 641, 643, 645, 647, 649, 650, 651, 652, 653, 654, 655, 656, 657, 658, 660, 662, 664, 666, 668, 669, 670, 671, 672, 673, 674, 675, 676, 677, 679, 681, 683, 685, 686, 687, 689, 691, 693, 695, 696, 698, 699, 701, 702, 703, 704, 705, 706, 707, 709, 710, 711, 712, 713, 714, 715, 716, 717, 718, 719, 721, 722, 723, 724, 725, 726, 727, 728, 729, 730, 731, 732, 733, 734, 735, 736, 737, 738, 739, 740, 742, 744, 745, 746, 747, 749, 750, 752, 753, 754, 755, 757, 759, 760, 761, 762, 764, 765, 766, 767, 768, 769, 770, 771, and 772.

In any of the methods described herein, the nucleotide sequence can have 95 percent or greater (e.g., 98 percent or 99 percent or greater) sequence identity to the nucleotide sequence set forth in SEQ ID NOs: 1, 6, 16, 18, 21, 23, 25, 27, 30, 34, 37, 39, 46, 51, 53, 60, 62, 68, 71, 74, 76, 80, 92, 95, 101, 112, 114, 116, 118, 123, 128, 130, 133, 135, 139, 141, 143, 145, 157, 161, 165, 168, 170, 189, 196, 204, 206, 208, 210, 222, 226, 236, 238, 240, 242, 244, 247, 249, 252, 254, 256, 260, 262, 264, 266, 268, 270, 272, 275, 277, 279, 282, 286, 289, 291, 295, 297, 299, 301, 303, 305, 307, 309, 311, 313, 315, 317, 319, 321, 323, 325, 327, 330, 332, 334, 336, 340, 352, 354, 356, 359, 361, 363, 365, 367, 370, 372, 374, 381, 383, 385, 387, 389, 391, 394, 403, 406, 408, 410, 412, 415, 417, 419, 422, 427, 430, 448, 450, 452, 455, 464, 466, 477, 479, 481, 483, 485, 487, 489, 491, 493, 495, 497, 499, 501, 503, 505, 507, 509, 511, 513, 515, 517, 519, 521, 523, 525, 527, 529, 531, 533, 536, 538, 541, 543, 546, 548, 550, 552, 554, 556, 559, 561, 563, 567, 569, 571, 573, 575, 577, 582, 584, 586, 588, 590, 592, 594, 596, 598, 600, 602, 604, 606, 609, 611, 613, 615, 617, 619, 621, 623, 626, 628, 630, 632, 634, 636, 638, 640, 642, 644, 646, 648, 659, 661, 663, 665, 667, 678, 680, 682, 684, 688, 690, 692, 694, 697, 700, 708, 720, 741, 743, 748, 751, 756, 758, and 763.

In any of the methods described herein, the nucleotide sequence can encode the polypeptide set forth in SEQ ID NOs: 2, 3, 4, 5, 7, 8, 9, 10, 11, 12, 13, 14, 15, 17, 19, 20, 22, 24, 26, 28, 29, 31, 32, 33, 35, 36, 38, 40, 41, 42, 43, 44, 45, 47, 48, 49, 50, 52, 54, 55, 56, 57, 58, 59, 61, 63, 64, 65, 66, 67, 69, 70, 72, 73, 75, 77, 78, 79, 81, 82, 83, 84, 85, 86, 87, 88, 89, 90, 91, 93, 94, 96, 97, 98, 99, 100, 102, 103, 104, 105, 106, 107, 108, 109, 110, 111, 113, 115, 117, 119, 120, 121, 122, 124, 125, 126, 127, 129, 131, 132, 134, 136, 137, 138, 140, 142, 144, 146, 147, 148, 149, 150, 151, 152, 153, 154, 155, 156, 158, 159, 160, 162, 163, 164, 166, 167, 169, 171, 172, 173, 174, 175, 176, 177, 178, 179, 180, 181, 182, 183, 184, 185, 186, 187, 188, 190, 191, 192, 193, 194, 195, 197, 198, 199, 200, 201, 202, 203, 205, 207, 209, 211, 212, 213, 214, 215, 216, 217, 218, 219, 220, 221, 223, 224, 225, 227, 228, 229, 230, 231, 232, 233, 234, 235, 237, 239, 241, 243, 245, 246, 248, 250, 251, 253, 255, 257, 258, 259, 261, 263, 265, 267, 269, 271, 273, 274, 276, 278, 280, 281, 283, 284, 285, 287, 288, 290, 292, 293, 294, 296, 298, 300, 302, 304, 306, 308, 310, 312, 314, 316, 318, 320, 322, 324, 326, 328, 329, 331, 333, 335, 337, 338, 339, 341, 342, 343, 344, 345, 346, 347, 348, 349, 350, 351, 353, 355, 357, 358, 360, 362, 364, 366, 368, 369, 371, 373, 375, 376, 377, 378, 379, 380, 382, 384, 386, 388, 390, 392, 393, 395, 396, 397, 398, 399, 400, 401, 402, 404, 405, 407, 409, 411, 413, 414, 416, 418, 420, 421, 423, 424, 425, 426, 428, 429, 431, 432, 433, 434, 435, 436, 437, 438, 439, 440, 441, 442, 443, 444, 445, 446, 447, 449, 451, 453, 454, 456, 457, 458, 459, 460, 461, 462, 463, 465, 467, 468, 469, 470, 471, 472, 473, 474, 475, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 535, 537, 539, 540, 542, 544, 545, 547, 549, 551, 553, 555, 557, 558, 560, 562, 564, 568, 570, 572, 574, 576, 578, 579, 580, 581, 583, 585, 587, 589, 591, 593, 595, 597, 599, 601, 603, 605, 607, 608, 610, 612, 614, 616, 618, 620, 622, 624, 625, 627, 629, 631, 633, 635, 637, 639, 641, 643, 645, 647, 649, 650, 651, 652, 653, 654, 655, 656, 657, 658, 660, 662, 664, 666, 668, 669, 670, 671, 672, 673, 674, 675, 676, 677, 679, 681, 683, 685, 686, 687, 689, 691, 693, 695, 696, 698, 699, 701, 702, 703, 704, 705, 706, 707, 709, 710, 711, 712, 713, 714, 715, 716, 717, 718, 719, 721, 722, 723, 724, 725, 726, 727, 728, 729, 730, 731, 732, 733, 734, 735, 736, 737, 738, 739, 740, 742, 744, 745, 746, 747, 749, 750, 752, 753, 754, 755, 757, 759, 760, 761, 762, 764, 765, 766, 767, 768, 769, 770, 771, and 772.

In any of the methods described herein, the method further can include harvesting biomass from the plant.

In any of the methods described herein, the regulatory region can be a promoter. For example, the promoter can be selected from the group consisting of YP0092, PT0676, PT0708, PT0613, PT0672, PT0678, PT0688, PT0837, the napin promoter, the Arcelin-5 promoter, the phaseolin gene promoter, the soybean trypsin inhibitor promoter, the ACP promoter, the stearoyl-ACP desaturase gene promoter, the soybean α' subunit of β-conglycinin promoter, the oleosin promoter, the 15 kD zein promoter, the 16 kD zein promoter, the 19 kD zein promoter, the 22 kD zein promoter, the 27 kD zein promoter, the Osgt-1 promoter, the beta-amylase gene promoter, the barley hordein gene promoter, p326, YP0144, YP0190, p13879, YP0050, p32449, 21876, YP0158, YP0214, YP0380, PT0848, PT0633, the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, rice actin promoter, maize ubiquitin-1 promoter, ribulose-1,5-bisphosphate carboxylase (RbcS) promoter, the pine cab6 promoter, the Cab-1 gene promoter from wheat, the CAB-1 promoter from spinach, the cab1R promoter from rice, the pyruvate orthophosphate dikinase (PPDK) promoter from corn, the tobacco Lhcb1*2 promoter, the *Arabidopsis thaliana* SUC2 sucrose-H+ symporter promoter, and a thylakoid membrane protein promoter from spinach, and PT0585.

In any of the methods described herein, the plant containing the exogenous nucleic acid can have an improved growth rate relative to a corresponding plant that does not contain the nucleic acid.

In any of the methods described herein, the plant containing the exogenous nucleic acid can have improved vegetative growth relative to a corresponding plant that does not contain nucleic acid.

This document also features a method of increasing tolerance of a plant to elevated levels of aluminum. The method includes introducing into a plurality of plant cells an isolated nucleic acid comprising a nucleic acid sequence encoding a polypeptide having 90 percent or greater sequence identity to an amino acid sequence set forth in SEQ ID NOs: 2, 3, 4, 5, 7, 8, 9, 10, 11, 12, 13, 14, 15, 17, 19, 20, 22, 24, 26, 28, 29, 31, 32, 33, 35, 36, 38, 40, 41, 42, 43, 44, 45, 47, 48, 49, 50, 52, 54, 55, 56, 57, 58, 59, 61, 63, 64, 65, 66, 67, 69, 70, 72, 73, 75, 77, 78, 79, 81, 82, 83, 84, 85, 86, 87, 88, 89, 90, 91, 93, 94, 96, 97, 98, 99, 100, 102, 103, 104, 105, 106, 107, 108, 109, 110, 111, 113, 115, 117, 119, 120, 121, 122, 124, 125, 126, 127, 129, 131, 132, 134, 136, 137, 138, 140, 142, 144, 146, 147, 148, 149, 150, 151, 152, 153, 154, 155, 156, 158, 159, 160, 162, 163, 164, 166, 167, 169, 171, 172, 173, 174, 175, 176, 177, 178, 179, 180, 181, 182, 183, 184, 185, 186, 187, 188, 190, 191, 192, 193, 194, 195, 197, 198, 199, 200, 201, 202, 203, 205, 207, 209, 211, 212, 213, 214, 215, 216, 217, 218, 219, 220, 221, 223, 224, 225, 227, 228, 229, 230, 231, 232, 233, 234, 235, 237, 239, 241, 243, 245, 246, 248, 250, 251, 253, 255, 257, 258, 259, 261, 263, 265, 267, 269, 271, 273, 274, 276, 278, 280, 281, 283, 284, 285, 287, 288, 290, 292, 293, 294, 296, 298, 300, 302, 304, 306, 308, 310, 312, 314, 316, 318, 320, 322, 324, 326, 328, 329, 331, 333, 335, 337, 338, 339, 341, 342, 343, 344, 345, 346, 347, 348, 349, 350, 351, 353, 355, 357, 358, 360, 362, 364, 366, 368, 369, 371, 373, 375, 376, 377, 378, 379, 380, 382, 384, 386, 388, 390, 392, 393, 395, 396, 397, 398, 399, 400, 401, 402, 404, 405, 407, 409, 411, 413, 414, 416, 418, 420, 421, 423, 424, 425, 426, 428, 429, 431, 432, 433, 434, 435, 436, 437, 438, 439, 440, 441, 442, 443, 444, 445, 446, 447, 449, 451, 453, 454, 456, 457, 458, 459, 460, 461, 462, 463, 465, 467, 468, 469, 470, 471, 472, 473, 474, 475, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 535, 537, 539, 540, 542, 544, 545, 547, 549, 551, 553, 555, 557, 558, 560, 562, 564, 568, 570, 572, 574, 576, 578, 579, 580, 581, 583, 585, 587, 589, 591, 593, 595, 597, 599, 601, 603, 605, 607, 608, 610, 612, 614, 616, 618, 620, 622, 624, 625, 627, 629, 631, 633, 635, 637, 639, 641, 643, 645, 647, 649, 650, 651, 652, 653, 654, 655, 656, 657, 658, 660, 662, 664, 666, 668, 669, 670, 671, 672, 673, 674, 675, 676, 677, 679, 681, 683, 685, 686, 687, 689, 691, 693, 695, 696, 698, 699, 701, 702, 703, 704, 705, 706, 707, 709, 710, 711, 712, 713, 714, 715, 716, 717, 718, 719, 721, 722, 723, 724, 725, 726, 727, 728, 729, 730, 731, 732, 733, 734, 735, 736, 737, 738, 739, 740, 742, 744, 745, 746, 747, 749, 750, 752, 753, 754, 755, 757, 759, 760, 761, 762, 764, 765, 766, 767, 768, 769, 770, 771, and 772; producing a plant from the plant cell; and growing the plant on soil having an elevated level of Al³⁺, wherein the plant has increased yield as compared to that of a control plant that does not comprise the nucleic acid. The nucleic acid sequence encoding the polypeptide can be operably linked to a regulatory region.

This document also features a method of increasing tolerance of a plant to elevated levels of aluminum. The method includes introducing into a plurality of plant cells an isolated nucleic acid comprising a nucleic acid sequence encoding a polypeptide having 90 percent or greater sequence identity to an amino acid sequence set forth in SEQ ID NOs: 2, 3, 4, 5, 7, 8, 9, 10, 11, 12, 13, 14, 15, 17, 19, 20, 22, 24, 26, 28, 29, 31, 32, 33, 35, 36, 38, 40, 41, 42, 43, 44, 45, 47, 48, 49, 50, 52, 54, 55, 56, 57, 58, 59, 61, 63, 64, 65, 66, 67, 69, 70, 72, 73, 75, 77, 78, 79, 81, 82, 83, 84, 85, 86, 87, 88, 89, 90, 91, 93, 94, 96, 97, 98, 99, 100, 102, 103, 104, 105, 106, 107, 108, 109, 110, 111, 113, 115, 117, 119, 120, 121, 122, 124, 125, 126, 127, 129, 131, 132, 134, 136, 137, 138, 140, 142, 144, 146, 147, 148, 149, 150, 151, 152, 153, 154, 155, 156, 158, 159, 160, 162, 163, 164, 166, 167, 169, 171, 172, 173, 174, 175, 176, 177, 178, 179, 180, 181, 182, 183, 184, 185, 186, 187, 188, 190, 191, 192, 193, 194, 195, 197, 198, 199, 200, 201, 202, 203, 205, 207, 209, 211, 212, 213, 214, 215, 216, 217, 218, 219, 220, 221, 223, 224, 225, 227, 228, 229, 230, 231, 232, 233, 234, 235, 237, 239, 241, 243, 245, 246, 248, 250, 251, 253, 255, 257, 258, 259, 261, 263, 265, 267, 269, 271, 273, 274, 276, 278, 280, 281, 283, 284, 285, 287, 288, 290, 292, 293, 294, 296, 298, 300, 302, 304, 306, 308, 310, 312, 314, 316, 318, 320, 322, 324, 326, 328, 329, 331, 333, 335, 337, 338, 339, 341, 342, 343, 344, 345, 346, 347, 348, 349, 350, 351, 353, 355, 357, 358, 360, 362, 364, 366, 368, 369, 371, 373, 375, 376, 377, 378, 379, 380, 382, 384, 386, 388, 390, 392, 393, 395, 396, 397, 398, 399, 400, 401, 402, 404, 405, 407, 409, 411, 413, 414, 416, 418, 420, 421, 423, 424, 425, 426, 428, 429, 431, 432, 433, 434, 435, 436, 437, 438, 439, 440, 441, 442, 443, 444, 445, 446, 447, 449, 451, 453, 454, 456, 457, 458, 459, 460, 461, 462, 463, 465, 467, 468, 469, 470, 471, 472, 473, 474, 475, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 535, 537, 539, 540, 542, 544, 545, 547, 549, 551, 553, 555, 557, 558, 560, 562, 564, 568, 570, 572, 574, 576, 578, 579, 580, 581, 583, 585, 587, 589, 591, 593, 595, 597, 599, 601, 603, 605, 607, 608, 610, 612, 614, 616, 618, 620, 622, 624, 625, 627, 629, 631, 633, 635, 637, 639, 641, 643, 645, 647, 649, 650, 651, 652, 653, 654, 655, 656, 657, 658, 660, 662, 664, 666, 668, 669, 670, 671, 672, 673, 674, 675, 676, 677, 679, 681, 683, 685, 686, 687, 689, 691, 693, 695, 696, 698, 699, 701, 702, 703, 704, 705, 706, 707, 709, 710, 711, 712, 713, 714, 715, 716, 717, 718, 719, 721, 722, 723, 724, 725, 726, 727, 728, 729, 730, 731, 732, 733, 734, 735, 736, 737, 738, 739, 740, 742, 744, 745, 746, 747, 749, 750, 752, 753, 754, 755, 757, 759, 760, 761, 762, 764, 765, 766, 767, 768, 769, 770, 771, and 772; and selecting a plant produced from the plurality of plant cells that has an increased tolerance to elevated Al³⁺ as compared to the tolerance in a corresponding control plant that does not comprise the isolated nucleic acid. The nucleic acid sequence encoding the polypeptide can be operably linked to a regulatory region.

This document also features a plant cell that contains an exogenous nucleic acid, the exogenous nucleic acid comprising a regulatory region operably linked to a nucleotide sequence encoding a polypeptide, wherein the HMM bit score of the amino acid sequence of the polypeptide is greater than about 65, the HMM based on the amino acid sequence depicted in any one of FIGS. 1-4, and wherein a plant produced from the plant cell is tolerant of elevated soil levels of Al³⁺ as compared to that of a control plant that does not comprise the nucleic acid, and wherein the plant is not tolerant of elevated saline levels.

This document also features a plant cell that contains an exogenous nucleic acid, the exogenous nucleic acid comprising a regulatory region operably linked to a nucleotide sequence encoding a polypeptide having 90 percent or greater sequence identity to an amino acid sequence set forth in SEQ ID NOs: 2, 3, 4, 5, 7, 8, 9, 10, 11, 12, 13, 14, 15, 17, 19, 20, 22, 24, 26, 28, 29, 31, 32, 33, 35, 36, 38, 40, 41, 42, 43, 44, 45, 47, 48, 49, 50, 52, 54, 55, 56, 57, 58, 59, 61, 63, 64, 65, 66, 67, 69, 70, 72, 73, 75, 77, 78, 79, 81, 82, 83, 84, 85, 86, 87, 88, 89, 90, 91, 93, 94, 96, 97, 98, 99, 100, 102, 103, 104, 105, 106, 107, 108, 109, 110, 111, 113, 115, 117, 119, 120, 121, 122, 124, 125, 126, 127, 129, 131, 132, 134, 136, 137, 138, 140, 142, 144, 146, 147, 148, 149, 150, 151, 152, 153, 154, 155, 156, 158, 159, 160, 162, 163, 164, 166, 167, 169, 171, 172, 173, 174, 175, 176, 177, 178, 179, 180, 181, 182, 183, 184, 185, 186, 187, 188, 190, 191, 192, 193, 194, 195, 197, 198, 199, 200, 201, 202, 203, 205, 207, 209, 211, 212, 213, 214, 215, 216, 217, 218, 219, 220, 221, 223, 224, 225, 227, 228, 229, 230, 231, 232, 233, 234, 235, 237, 239, 241, 243, 245, 246, 248, 250, 251, 253, 255, 257, 258, 259, 261, 263, 265, 267, 269, 271, 273, 274, 276, 278, 280, 281, 283, 284, 285, 287, 288, 290, 292, 293, 294, 296, 298, 300, 302, 304, 306, 308, 310, 312, 314, 316, 318, 320, 322, 324, 326, 328, 329, 331, 333, 335, 337, 338, 339, 341, 342, 343, 344, 345, 346, 347, 348, 349, 350, 351, 353, 355, 357, 358, 360, 362, 364, 366, 368, 369, 371, 373, 375, 376, 377, 378, 379, 380, 382, 384, 386, 388, 390, 392, 393, 395, 396, 397, 398, 399, 400, 401, 402, 404, 405, 407, 409, 411, 413, 414, 416, 418, 420, 421, 423, 424, 425, 426, 428, 429, 431, 432, 433, 434, 435, 436, 437, 438, 439, 440, 441, 442, 443, 444, 445, 446, 447, 449, 451, 453, 454, 456, 457, 458, 459, 460, 461, 462, 463, 465, 467, 468, 469, 470, 471, 472, 473, 474, 475, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 535, 537, 539, 540, 542, 544, 545, 547, 549, 551, 553, 555, 557, 558, 560, 562, 564, 568, 570, 572, 574, 576, 578, 579, 580, 581, 583, 585, 587, 589, 591, 593, 595, 597, 599, 601, 603, 605, 607, 608, 610, 612, 614, 616, 618, 620, 622, 624, 625, 627, 629, 631, 633, 635, 637, 639, 641, 643, 645, 647, 649, 650, 651, 652, 653, 654, 655, 656, 657, 658, 660, 662, 664, 666, 668, 669, 670, 671, 672, 673, 674, 675, 676, 677, 679, 681, 683, 685, 686, 687, 689, 691, 693, 695, 696, 698, 699, 701, 702, 703, 704, 705, 706, 707, 709, 710, 711, 712, 713, 714, 715, 716, 717, 718, 719, 721, 722, 723, 724, 725, 726, 727, 728, 729, 730, 731, 732, 733, 734, 735, 736, 737, 738, 739, 740, 742, 744, 745, 746, 747, 749, 750, 752, 753, 754, 755, 757, 759, 760, 761, 762, 764, 765, 766, 767, 768, 769, 770, 771, and 772, and wherein a plant produced from the plant cell is tolerant of elevated soil levels of Al³⁺ as compared to that of a control plant that does not comprise the nucleic acid, and wherein the plant is not tolerant of elevated saline levels.

This document also features a transgenic plant comprising a plant cell described herein, progeny of the plants that have increased tolerance to elevated Al³⁺ conditions as compared to that of a control plant that does not comprise the nucleic acid, and wherein the progeny is not tolerant of elevated saline levels, seeds of the transgenic plants, and vegetative tissue of the transgenic plants, as well as food and feed products that include the vegetative tissue. The plant can be selected from the group consisting of *Panicum virgatum, Sorghum bicolor, Miscanthus giganteus, Saccharum* sp., *Populus balsamifera, Zea mays, Glycine max, Brassica*

*napus, Triticum aestivum, Gossypium hirsutum, Oryza sativa, Helianthus annuus, Medicago sativa, Beta vulgaris,* or *Pennisetum glaucum.*

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF DRAWINGS

FIGS. 1A-1D contain an alignment of the amino acid sequence of CeresClone: 375578 (SEQ ID NO: 353) with homologous and/or orthologous amino acid sequences. In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE version 3.52.

FIGS. 2A-2C contain an alignment of the amino acid sequence of CeresClone:11684 (SEQ ID NO: 237) with homologous and/or orthologous amino acid sequences.

FIGS. 3A-3C contain an alignment of the amino acid sequence of CeresClone: 24255 (SEQ ID NO: 451) with homologous and/or orthologous amino acid sequences.

Figure 4C:
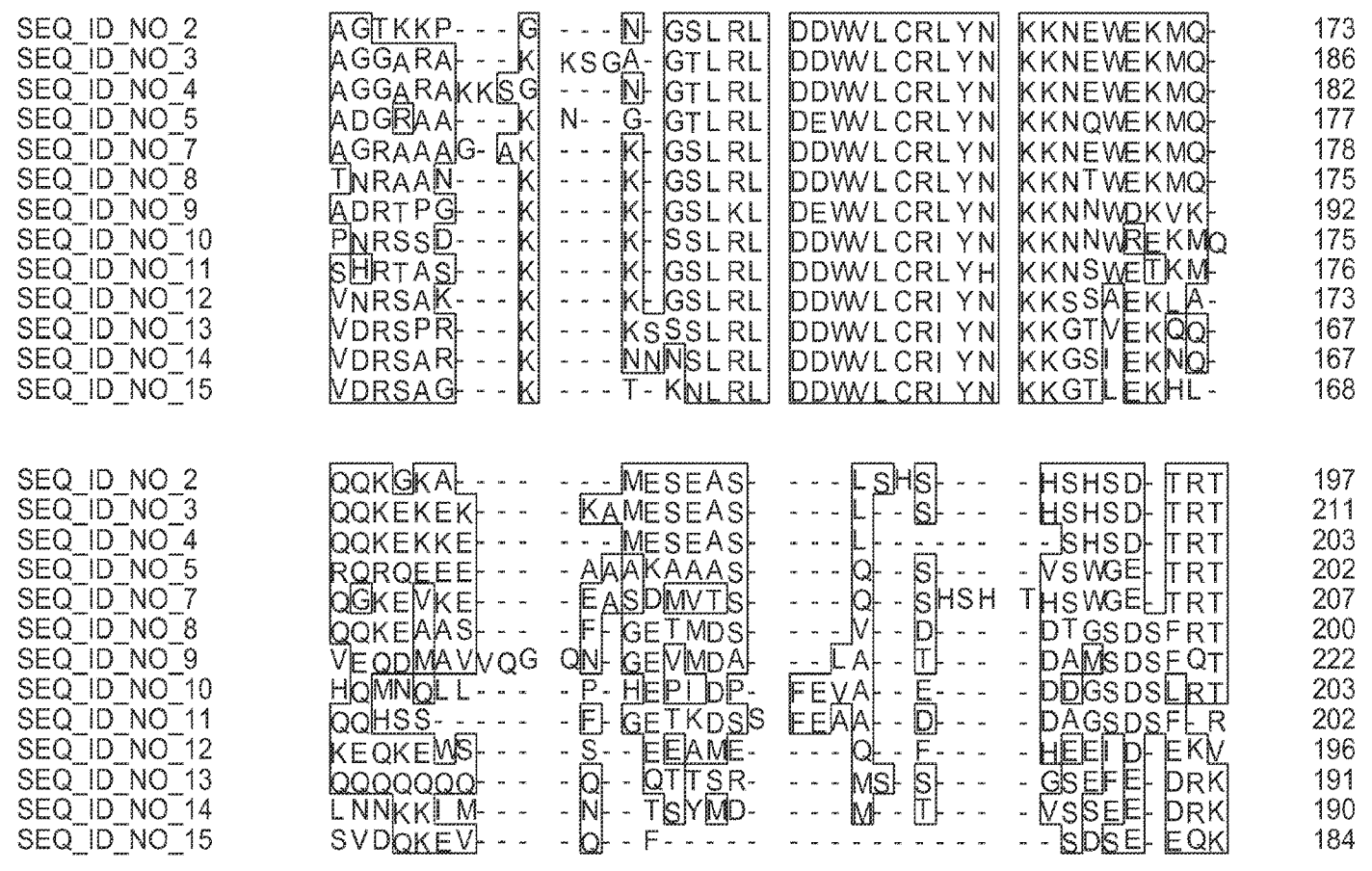
Figure 4E:
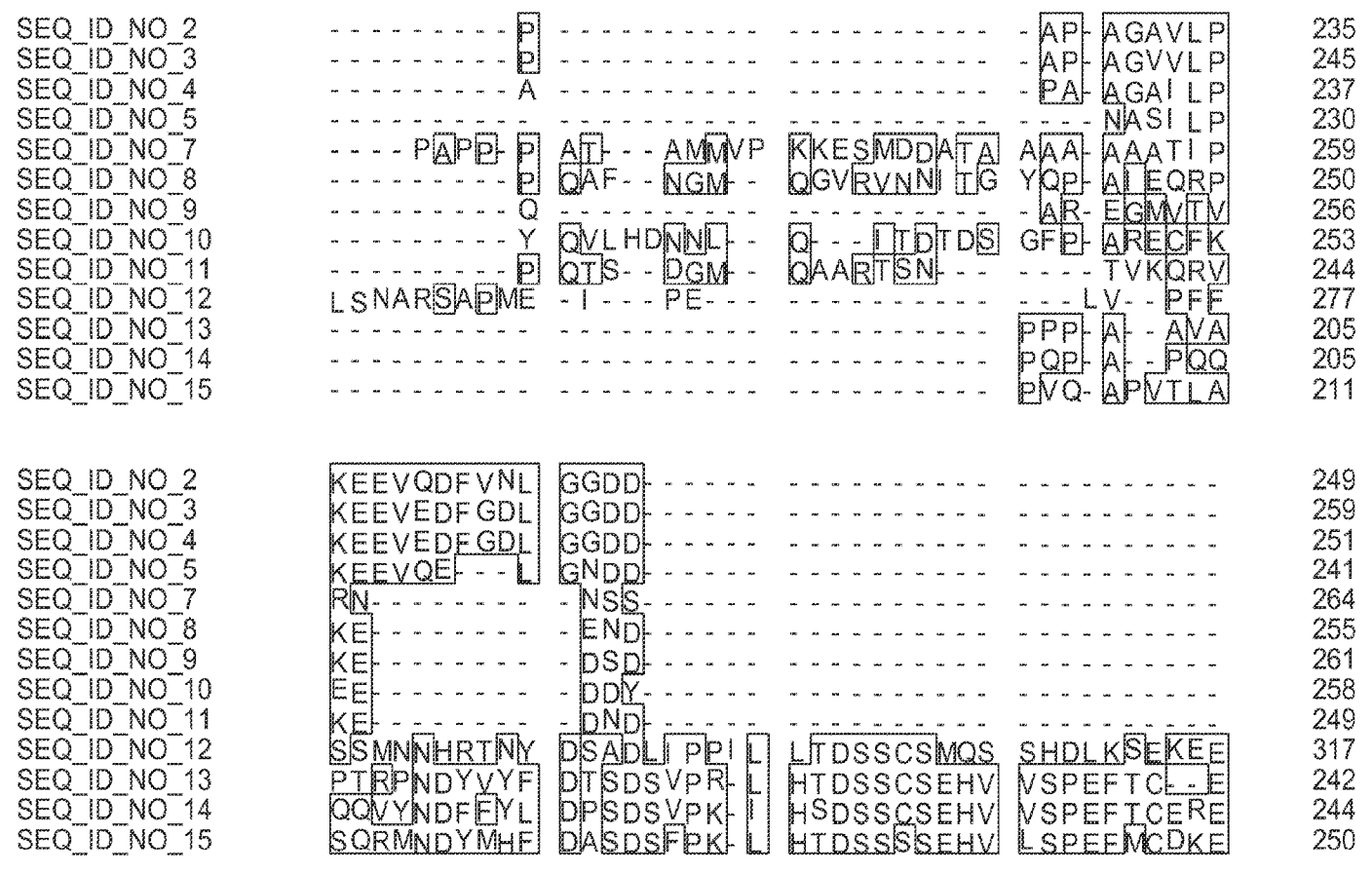
Figure 4F:
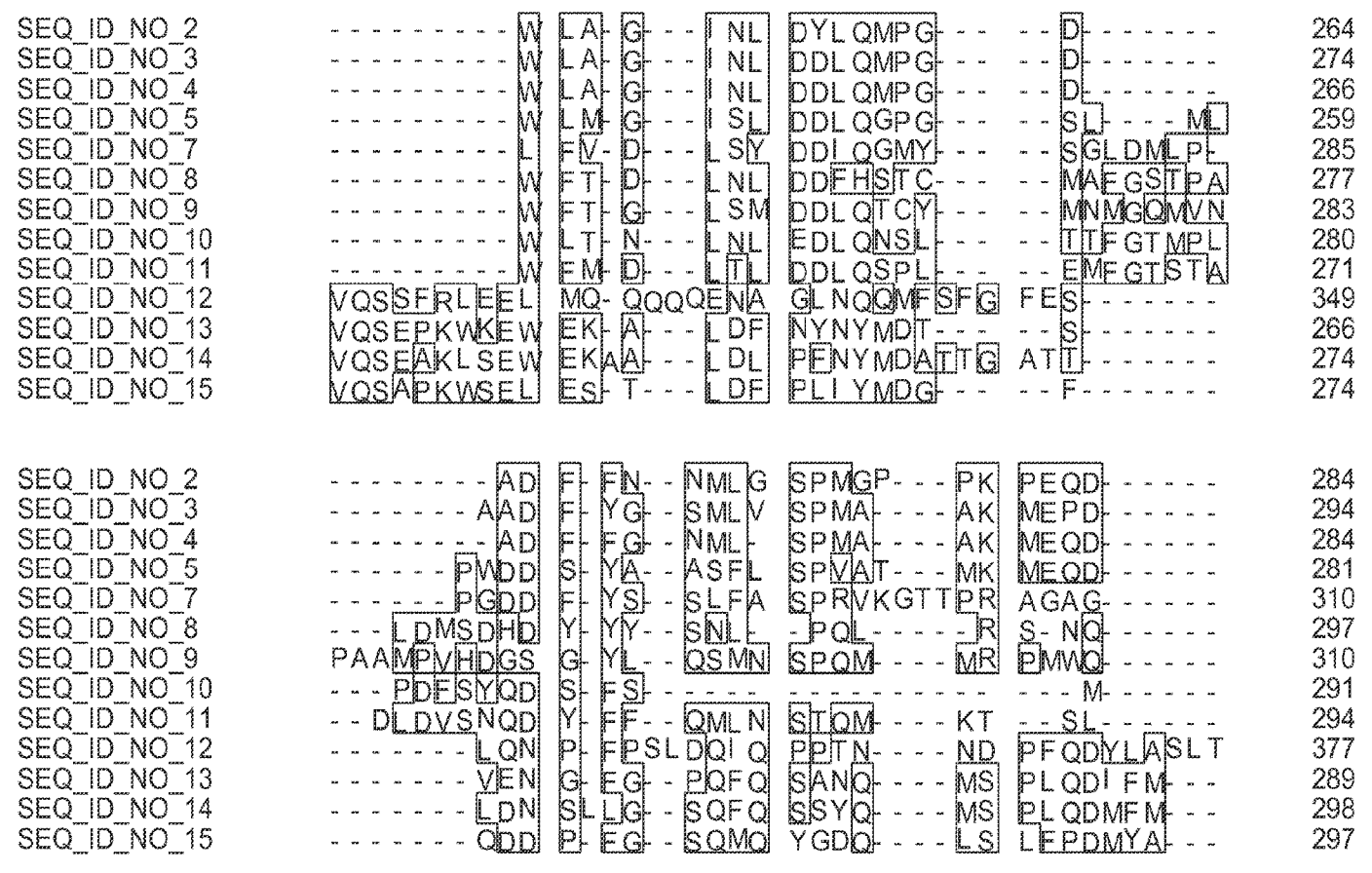

FIGS. 4A-4G contain an alignment of the amino acid sequence of CeresClone: 1752915 (SEQ ID NO: 2) with homologous and/or orthologous amino acid sequences.

DETAILED DESCRIPTION

Figure 4G:
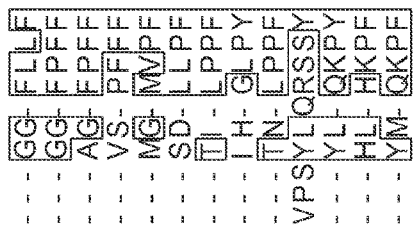

The invention features methods and materials related to modulating aluminum tolerance in plants. In some embodiments, the plants may also have, for example, modulated levels of lignin, modified root architecture, modified herbicide resistance, modified carotenoid biosynthesis, or modulated cell wall content. The methods described herein can include transforming a plant cell with a nucleic acid encoding an aluminum tolerance-modulating polypeptide, wherein expression of the polypeptide results in a modulated level of aluminum tolerance. Plant cells produced using such methods can be grown to produce plants having an increased tolerance to elevated levels of aluminum. Such plants can have increased plant yield in soil containing elevated levels of $Al^{3+}$.

I. Definitions

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Modulation" of the level of aluminum tolerance refers to the change in the level of the aluminum tolerance that is observed as a result of expression of, or transcription from, an exogenous nucleic acid in a plant cell and/or plant. The change in level is measured relative to the corresponding level in control plants. Aluminum tolerance can be assessed by measuring root growth and/or plant height of plants grown in acidified soils containing elevated levels of $Al^{3+}$. The concentration of $Al^{3+}$ considered to be elevated can be adjusted depending on the species being tested as plant species vary in their capacity to tolerate aluminum. For example, rice is more tolerant of aluminum than sorghum. As such, to determine increased tolerance to aluminum in rice, concentrations greater than 160 µM $Al^{3+}$ can be used. In sorghum, concentrations of around 27 µM $Al^{3+}$ can be used. For switchgrass, concentrations of around 600 µM can be used.

"Nucleic acid" and "polynucleotide" are used interchangeably herein, and refer to both RNA and DNA, including cDNA, genomic DNA, synthetic DNA, and DNA or RNA containing nucleic acid analogs. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

II. Polypeptides

Polypeptides described herein include aluminum tolerance-modulating polypeptides. Aluminum tolerance-modulating polypeptides can be effective to modulate (e.g., increase) aluminum tolerance when expressed in a plant or plant cell. Such polypeptides typically contain at least one domain indicative of aluminum tolerance-modulating polypeptides, as described in more detail herein. Aluminum tolerance-modulating polypeptides typically have an HMM bit score that is greater than 65 as described in more detail herein. In some embodiments, aluminum tolerance-modulating polypeptides have greater than 80% identity to SEQ ID NOs: 2, 3, 4, 5, 7, 8, 9, 10, 11, 12, 13, 14, 15, 17, 19, 20, 22, 24, 26, 28, 29, 31, 32, 33, 35, 36, 38, 40, 41, 42, 43, 44, 45, 47, 48, 49, 50, 52, 54, 55, 56, 57, 58, 59, 61, 63, 64, 65, 66, 67, 69, 70, 72, 73, 75, 77, 78, 79, 81, 82, 83, 84, 85, 86, 87, 88, 89, 90, 91, 93, 94, 96, 97, 98, 99, 100, 102, 103, 104, 105, 106, 107, 108, 109, 110, 111, 113, 115, 117, 119, 120, 121, 122, 124, 125, 126, 127, 129, 131, 132, 134, 136, 137, 138, 140, 142, 144, 146, 147, 148, 149, 150, 151, 152, 153, 154, 155, 156, 158, 159, 160, 162, 163, 164, 166, 167, 169, 171, 172, 173, 174, 175, 176, 177, 178, 179, 180, 181, 182, 183, 184, 185, 186, 187, 188, 190, 191, 192, 193, 194, 195, 197, 198, 199, 200, 201, 202, 203, 205, 207, 209, 211, 212, 213, 214, 215, 216, 217, 218, 219, 220, 221, 223, 224, 225, 227, 228, 229, 230, 231, 232, 233, 234, 235, 237, 239, 241, 243, 245, 246, 248, 250, 251, 253, 255, 257, 258, 259, 261, 263, 265, 267, 269, 271, 273, 274, 276, 278, 280, 281, 283, 284, 285, 287, 288, 290, 292, 293, 294, 296, 298, 300, 302, 304, 306, 308, 310, 312, 314, 316, 318, 320, 322, 324, 326, 328, 329, 331, 333, 335, 337, 338, 339, 341, 342, 343, 344, 345, 346, 347, 348, 349, 350, 351, 353, 355, 357, 358, 360, 362, 364, 366, 368, 369, 371, 373, 375, 376, 377, 378, 379, 380, 382, 384, 386, 388, 390, 392, 393, 395, 396, 397, 398, 399, 400, 401, 402, 404, 405, 407, 409, 411, 413, 414, 416, 418, 420, 421, 423, 424, 425, 426, 428, 429, 431, 432, 433, 434, 435, 436, 437, 438, 439, 440, 441, 442, 443, 444, 445, 446, 447, 449, 451, 453, 454, 456, 457, 458, 459, 460, 461, 462, 463, 465, 467, 468, 469, 470, 471, 472, 473, 474, 475, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 535, 537, 539, 540, 542, 544, 545, 547, 549, 551, 553, 555, 557, 558, 560, 562, 564, 568, 570, 572, 574, 576, 578, 579, 580, 581, 583, 585, 587, 589, 591, 593, 595, 597, 599, 601, 603, 605, 607, 608, 610, 612, 614, 616, 618, 620, 622, 624, 625, 627, 629, 631, 633, 635, 637, 639, 641, 643, 645, 647, 649, 650, 651, 652, 653, 654, 655, 656, 657, 658, 660, 662, 664, 666, 668, 669, 670, 671, 672, 673, 674, 675, 676, 677, 679, 681, 683, 685, 686, 687, 689, 691, 693, 695, 696, 698, 699, 701, 702, 703, 704, 705, 706, 707, 709, 710, 711, 712, 713, 714, 715, 716, 717, 718, 719, 721, 722, 723, 724, 725, 726, 727, 728, 729, 730, 731, 732, 733, 734, 735, 736, 737, 738, 739, 740, 742, 744, 745, 746, 747, 749, 750, 752, 753, 754, 755, 757, 759, 760, 761, 762, 764, 765, 766, 767, 768, 769, 770, 771, or 772 as described in more detail herein.

A. Domains Indicative of Aluminum Tolerance-Modulating Polypeptides

An aluminum tolerance-modulating polypeptide can contain a NAC domain, which is predicted to be characteristic of an aluminum tolerance modulating polypeptide. SEQ ID NO: 2 sets forth the amino acid sequence of a *Panicum virgatum* clone, identified herein as CeresClone: 1752915 (SEQ ID NO:1), that is predicted to contain a NAC protein domain. For example, an aluminum tolerance-modulating polypeptide can comprise a NAC protein domain having 60 percent or greater (e.g., 65, 70, 75, 80, 85, 90, 95, 97, 98, 99, or 100%) sequence identity to residues 14 to 139 of SEQ ID NO: 2. In some embodiments, an aluminum tolerance-modulating polypeptide can comprise a NAC protein domain having 60 percent or greater (e.g., 65, 70, 75, 80, 85, 90, 95, 97, 98, 99, or 100%) sequence identity to the NAC protein domain of one or more of the polypeptides set forth in SEQ ID NOs: 3, 4, 5, 7, 8, 9, 10, 11, 12, 13, 14, 15, 17, 19, 20, 22, 24, 26, 28, 29, 31, 32, 33, 35, 36, 38, 40, 41, 42, 43, 44, 45, 47, 48, 49, 50, 52, 54, 55, 56, 57, 58, 59, 61, 63, 64, 65, 66, 67, 69, 70, 72, 73, 75, 77, 78, 79, 81, 82, 83, 84, 85, 86, 87, 88, 89, 90, 91, 93, 94, 96, 97, 98, 99, 100, 102, 103, 104, 105, 106, 107, 108, 109, 110, 111, 113, 115, 117, 119, 120, 121, 122, 124, 125, 126, 127, 129, 131, 132, 134, 136, 137, 138, 140, 142, 144, 146, 147, 148, 149, 150, 151, 152, 153, 154, 155, 156, 158, 159, 160, 162, 163, 164, 166, 167, 169, 171, 172, 173, 174, 175, 176, 177, 178, 179, 180, 181, 182, 183, 184, 185, 186, 187, 188, 190, 191, 192, 193, 194, 195, 197, 198, 199, 200, 201, 202, 203, 205, 207, 209, 211, 212, 213, 214, 215, 216, 217, 218, 219, 220, 221, 223, 224, 225, 227, 228, 229, 230, 231, 232, 233, 234, and 235. The NAC protein domains of such sequences are set forth in the Sequence Listing. The NAC domain (about 160 amino acids) was identified from the No apical meristem (NAM) protein domain, ATFL-2, and CUC2 (Cup-Shaped Cotyledon). See Ooka et al. 2003, *DNA Res.* 20: 239-247; Fang et al. 2008, *Mol. Genet. Genomics* 280: 547-563). The NAM protein domain is characteristic of plant development proteins. NAM proteins have a role in determining positions of meristems and primordial. Mutations in NAM result in the failure to develop a shoot apical meristem in *petunia* embryos. See, e.g., Souer, et al., *Cell* 85:159-170 (1996).

An aluminum tolerance-modulating polypeptide can contain an AN1-like Zinc finger domain and an A20-like zinc finger domain, which are predicted to be characteristic of an aluminum tolerance-modulating polypeptide. For example, SEQ ID NO: 237 sets forth the amino acid sequence of an *Arabidopsis thaliana* clone, identified herein as CeresClone: 11684 (SEQ ID NO: 236), that is predicted to contain AN1-like and A20-like zinc finger domains. For example, an aluminum tolerance-modulating polypeptide can comprise an AN1-like Zinc finger domain having 60 percent or greater (e.g., 65, 70, 75, 80, 85, 90, 95, 97, 98, 99, or 100%) sequence identity to residues 101 to 140 of SEQ ID NO: 237 and can comprise an A20-like Zinc finger domain having 60 percent or greater (e.g., 65, 70, 75, 80, 85, 90, 95, 97, 98, 99, or 100%) sequence identity to residues 25 to 47 of SEQ ID NO: 237. In some embodiments, an aluminum tolerance-modulating polypeptide can comprise an AN1-like Zinc finger domain and an A20-like zinc finger domain having 60 percent or greater (e.g., 65, 70, 75, 80, 85, 90, 95, 97, 98, 99, or 100%) sequence identity to the AN1-like and A20-like zinc finger domains of one or more of the polypeptides set forth in SEQ ID NOs: 239, 241, 243, 245, 246, 248, 250, 251, 253, 255, 257, 258, 259, 261, 263, 265, 267, 269, 271, 273, 274, 276, 278, 280, 281, 283, 284, 285, 287, 288, 290, 292, 293, 294, 296, 298, 300, 302, 304, 306, 308, 310, 312, 314, 316, 318, 320, 322, 324, 326, 328, 329, 331, 333, 335, 337, 338, 339, 341, 342, 343, 344, 345, 346, 347, 348, 349, 350, and 351. The AN1-like and A20-like zinc finger domains of such sequences are set forth in the Sequence Listing. The AN1-like zinc finger domain is a dimetal (zinc)-bound alpha/beta fold, with six conserved cysteines and two histidines that can coordinate 2 zinc atoms. The A20-like zinc finger domain can be a ubiquitin binding domain that mediates self-association. Stress-associated proteins (SAPs) can have an AN1-like zinc finger domain and an A20-like zinc finger domain. See, e.g., Vij and Tyag, *Mol Genet Genomics,* 276(6):565-75 (2006).

SEQ ID NO: 451 sets forth the amino acid sequence of an *Arabidopsis thaliana* clone, identified herein as CeresClone: 24255 (SEQ ID NO: 450), that also is predicted to contain AN1-like and A20-like zinc finger domains. For example, an aluminum tolerance-modulating polypeptide can comprise an AN1-like Zinc finger domain having 60 percent or greater (e.g., 65, 70, 75, 80, 85, 90, 95, 97, 98, 99, or 100%) sequence identity to residues 102 to 141 of SEQ ID NO: 451 and can comprise an A20-like Zinc finger domain having 60 percent or greater (e.g., 65, 70, 75, 80, 85, 90, 95, 97, 98, 99, or 100%) sequence identity to residues 14 to 36 of SEQ ID NO: 451. In some embodiments, an aluminum tolerance-modulating polypeptide can comprise an AN1-like Zinc finger domain and an A20-like zinc finger domain having 60 percent or greater (e.g., 65, 70, 75, 80, 85, 90, 95, 97, 98, 99, or 100%) sequence identity to the AN1-like and A20-like zinc finger domains of one or more of the polypeptides set forth in SEQ ID NOs: 453, 454, 456, 457, 458, 459, 460, 461, 462, 463, 465, 467, 468, 469, 470, 471, 472, 473, 474, 475, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 535, 537, 539, 540, 542, 544, 545, 547, 549, 551, 553, 555, 557, 558, 560, 562, 564, 568, 570, 572, 574, 576, 578, 579, 580, 581, 583, 585, 587, 589, 591, 593, 595, 597, 599, 601, 603, 605, 607, 608, 610, 612, 614, 616, 618, 620, 622, 624, 625, 627, 629, 631, 633, 635, 637, 639, 641, 643, 645, 647, 649, 650, 651, 652, 653, 654, 655, 656, 657, 658, 660, 662, 664, 666, 668, 669, 670, 671, 672, 673, 674, 675, 676, 677, 679, 681, 683, 685, 686, 687, 689, 691, 693, 695, 696, 698, 699, 701, 702, 703, 704, 705, 706, 707, 709, 710, 711, 712, 713, 714, 715, 716, 717, 718, 719, 721, 722, 723, 724, 725, 726, 727, 728, 729, 730, 731, 732, 733, 734, 735, 736, 737, 738, 739, 740, 742, 744, 745, 746, 747, 749, 750, 752, 753, 754, 755, 757, 759, 760, 761, 762, 764, 765, 766, 767, 768, 769, 770, 771, and 772.

An aluminum tolerance-modulating polypeptide can contain an IQ domain, which is predicted to be characteristic of an aluminum tolerance-modulating polypeptide. SEQ ID NO: 353 sets forth the amino acid sequence of a Zea mays clone, identified herein as CeresClone: 375578 (SEQ ID NO: 352), that is predicted to contain an IQ domain. For example, an aluminum tolerance-modulating polypeptide can comprise an IQ domain having 60 percent or greater (e.g., 65, 70, 75, 80, 85, 90, 95, 97, 98, 99, or 100%) sequence identity to residues 139 to 157 of SEQ ID NO: 353. In some embodiments, an aluminum tolerance-modulating polypeptide can comprise an IQ domain having 60 percent or greater (e.g., 65, 70, 75, 80, 85, 90, 95, 97, 98, 99, or 100%) sequence identity to the IQ domain of one or more of the polypeptides set forth in SEQ ID NOs: 355, 357, 358, 360, 362, 364, 366, 368, 369, 371, 373, 375, 376, 377, 378, 379, 380, 382, 384, 386, 388, 390, 392, 393, 395, 396, 397, 398, 399, 400, 401, 402, 404, 405, 407, 409, 411, 413, 414, 416, 418, 420, 421, 423, 424, 425, 426, 428, 429, 431, 432, 433, 434, 435, 436, 437, 438, 439, 440, 441, 442, 443, 444, 445, 446, 447, and 449. The IQ domain is a consensus for calcium-independent binding of calmodulin, which is a calcium sensor and helps regulate events through its interaction with a diverse group of cellular proteins. See Rhoads and Friedberg, *FASEB J.*, 11(5):331-40 (1997).

In some embodiments, an aluminum tolerance-modulating polypeptide is truncated at the amino- or carboxy-terminal end of a naturally occurring polypeptide. A truncated polypeptide may retain certain domains of the naturally occurring polypeptide while lacking others. Thus, length variants that are up to 5 amino acids shorter or longer typically exhibit the aluminum tolerance-modulating activity of a truncated polypeptide. In some embodiments, a truncated polypeptide is a dominant negative polypeptide. Expression in a plant of such a truncated polypeptide confers a difference in the level of aluminum tolerance of a plant as compared to the corresponding level of a control plant that does not comprise the truncation.

B. Functional Homologs Identified by Reciprocal BLAST® (Sequence Similarity Search)

Functional homologs can also be created via site-directed mutagenesis of the coding sequence for an aluminum tolerance-modulating polypeptide, or by combining domains from the coding sequences for different naturally-occurring aluminum tolerance-modulating polypeptides ("domain swapping"). The term "functional homolog" is sometimes applied to the nucleic acid that encodes a functionally homologous polypeptide. Functional homologs can be identified by analysis of nucleotide and polypeptide sequence alignments. For example, performing a query on a database of nucleotide or polypeptide sequences can identify homologs of aluminum tolerance-modulating polypeptides. Sequence analysis can involve BLAST®, Reciprocal BLAST®, or PSI-BLAST® analysis of nonredundant databases using an aluminum tolerance-modulating polypeptide amino acid sequence as the reference sequence Amino acid sequence is, in some instances, deduced from the nucleotide sequence. Those polypeptides in the database that have greater than 40% sequence identity are candidates for further evaluation for suitability as an aluminum tolerance-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in aluminum tolerance-modulating polypeptides, e.g., conserved functional domains.

Conserved regions can be identified by locating a region within the primary amino acid sequence of an aluminum tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Figure 1A:
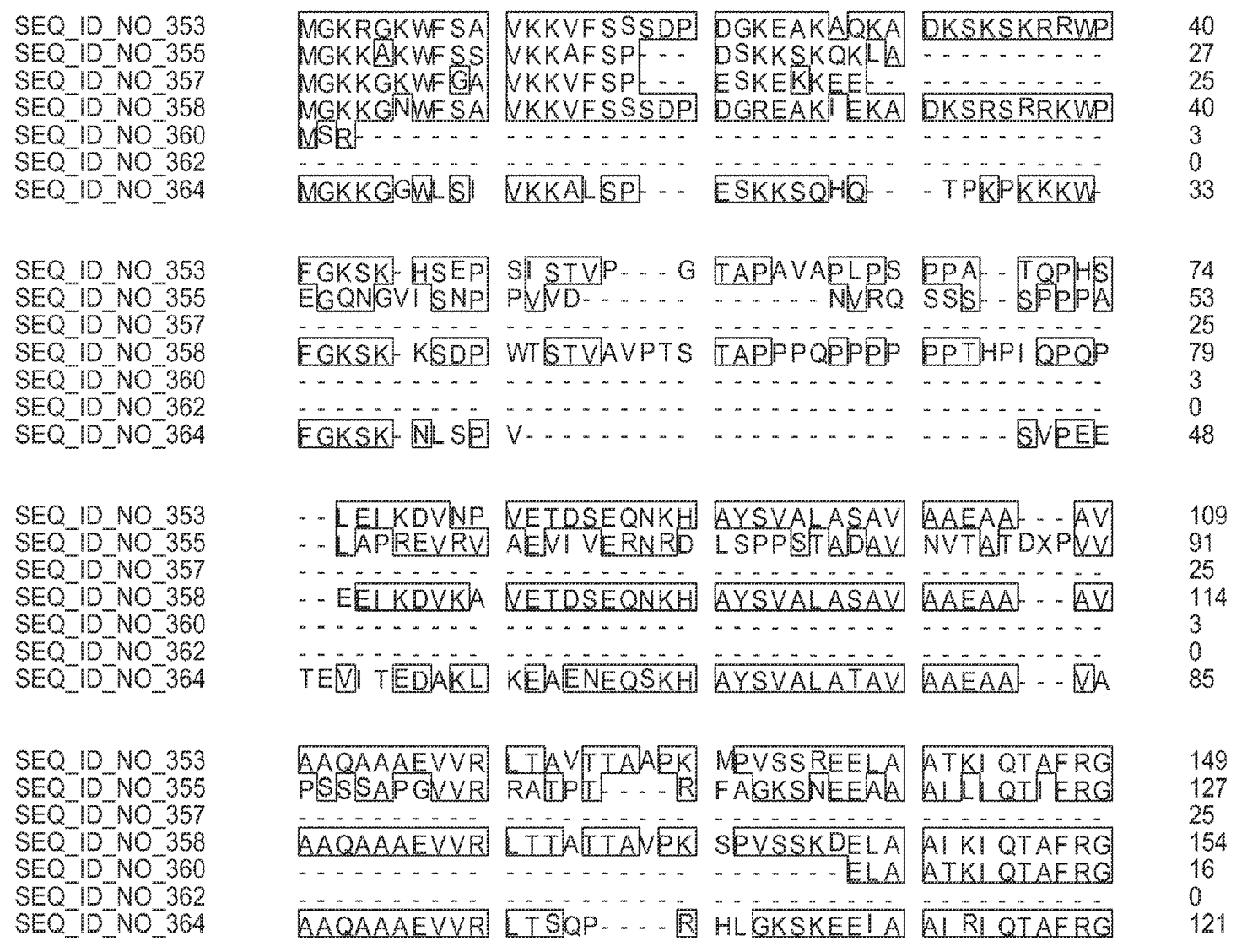
Figure 1B:
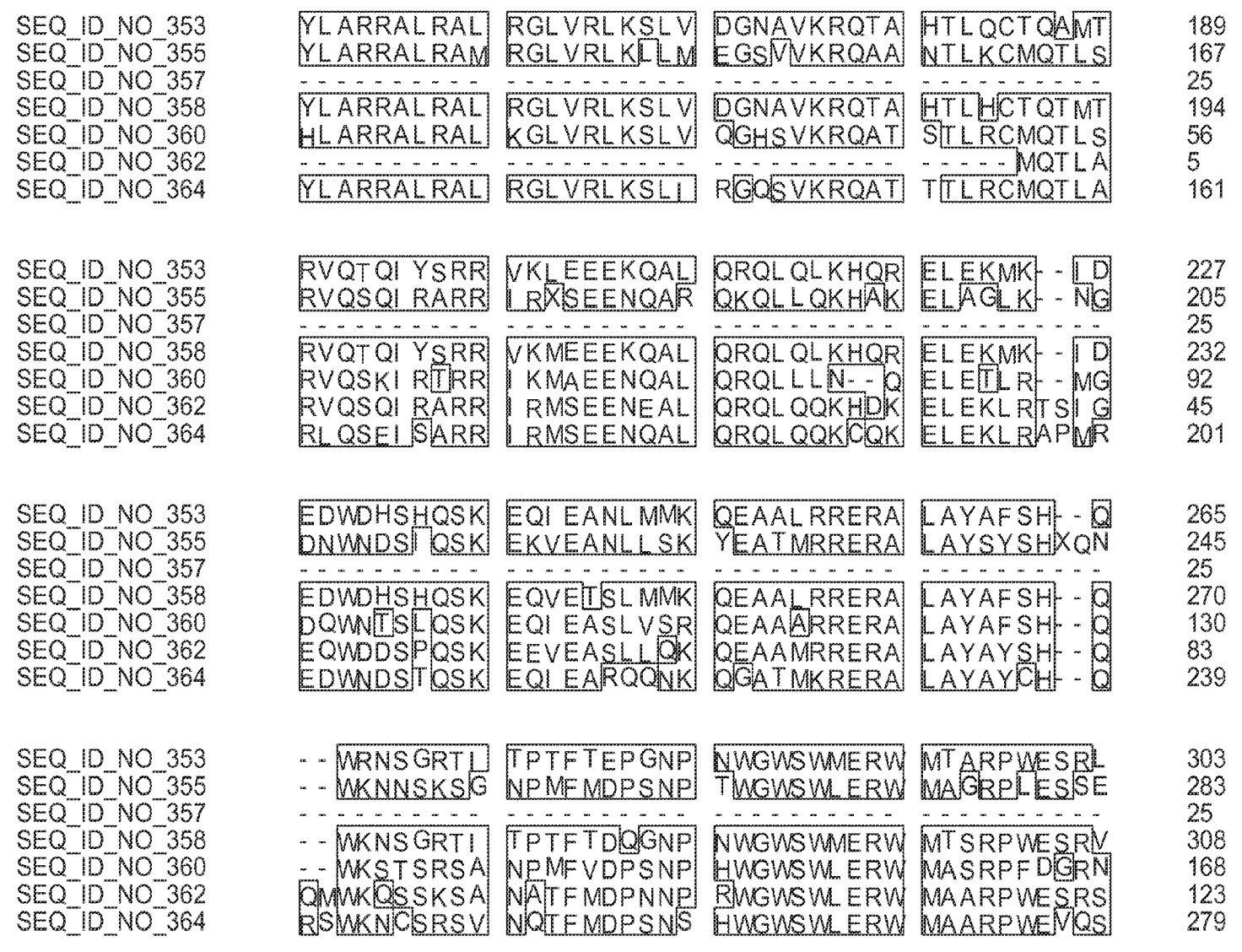
Figure 1C:
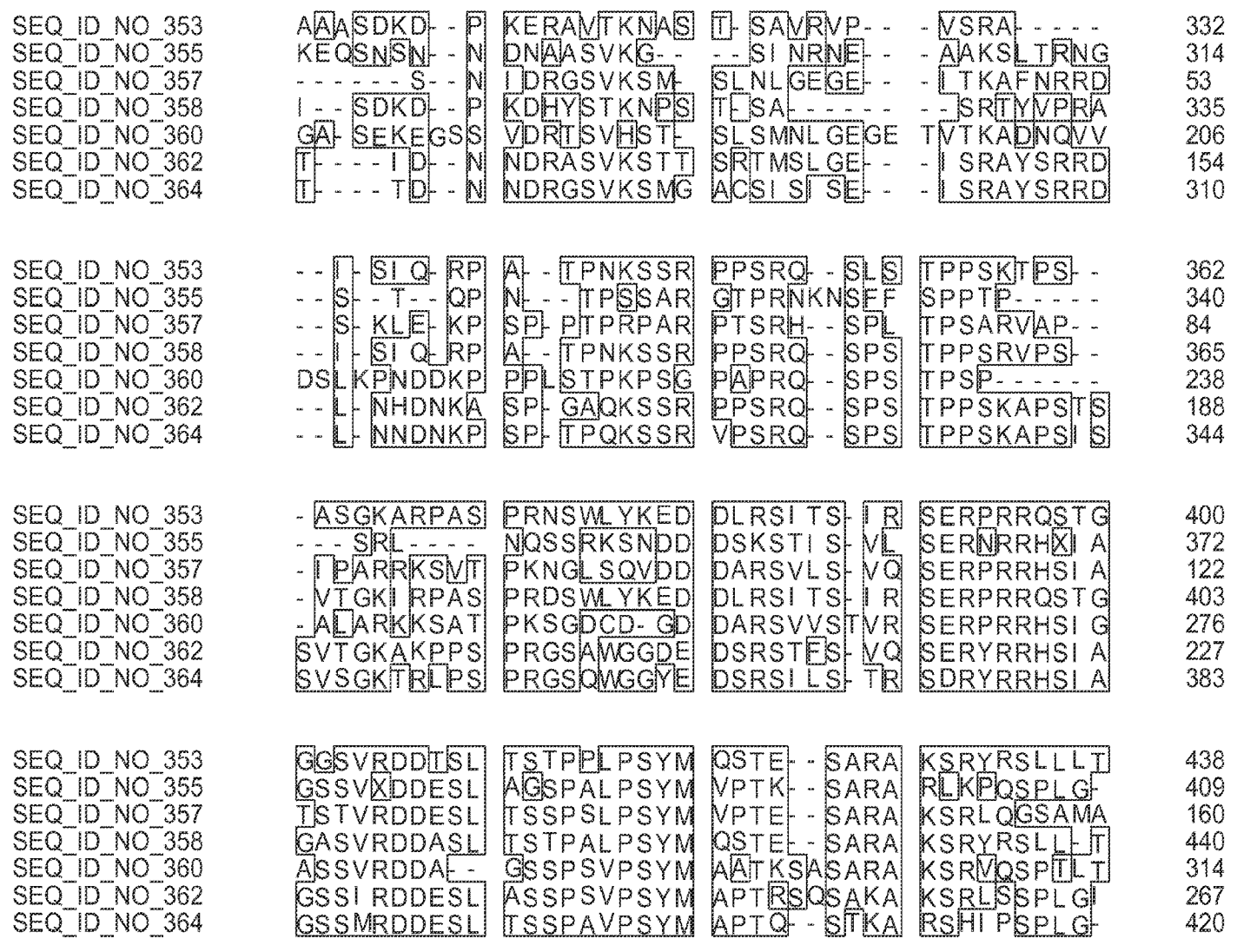

Examples of amino acid sequences of functional homologs of the polypeptide set forth in SEQ ID NO: 353 are provided in FIG. 1 and in the Sequence Listing. Such functional homologs include, for example, Ceres-Clone_106263 (SEQ ID NO: 355), CeresClone_335348 (SEQ ID NO: 357), GI_115440873 (SEQ ID NO: 358), CeresClone_826796 (SEQ ID NO: 360), CeresAnnot_1465047 (SEQ ID NO: 362), CeresClone_1919901 (SEQ ID NO: 364), SEEDLINE:ME02064 Ceres-Clone_375578 mutated (SEQ ID NO: 366), Ceres-Clone_520008 (SEQ ID NO: 368), GI_7413581 (SEQ ID NO: 369), CeresClone_228069 (SEQ ID NO: 371), Ceres-Clone_467508 (SEQ ID NO: 373), CeresClone_1829581 (SEQ ID NO: 375), GI_125550655 (SEQ ID NO: 376), GI_15231175 (SEQ ID NO: 377), GI_145357576 (SEQ ID NO: 378), GI_125528277 (SEQ ID NO: 379), GI_224032591 (SEQ ID NO: 380), CeresAnnot_8669409 (SEQ ID NO: 382), CeresClone_1901601 (SEQ ID NO: 384), CeresClone_2034697 (SEQ ID NO: 386), Ceres-Clone_1747444 (SEQ ID NO: 388), CeresClone_1998974 (SEQ ID NO: 390), CeresClone_1883040 (SEQ ID NO: 392), GI_326520123 (SEQ ID NO: 393), Ceres-Clone_101697218 (SEQ ID NO: 395), GI_215701453 (SEQ ID NO: 396), GI_225449126 (SEQ ID NO: 397), GI_147809623 (SEQ ID NO: 398), GI_224109704 (SEQ ID NO: 399), GI_225439898 (SEQ ID NO: 400), GI_218196002 (SEQ ID NO: 401), GI_54306075 (SEQ ID NO: 402), CeresAnnot_1484880 (SEQ ID NO: 404), GI_224028605 (SEQ ID NO: 405), CeresAnnot_1528800 (SEQ ID NO: 407), CeresClone_1792902 (SEQ ID NO:

409), CeresClone_1806867 (SEQ ID NO: 411), CeresClone_1727738 (SEQ ID NO: 413), GI_238007500 (SEQ ID NO: 414), CeresAnnot_8724651 (SEQ ID NO: 416), CeresClone_1897134 (SEQ ID NO: 418), CeresClone_1859266 (SEQ ID NO: 420), GI_194696788 (SEQ ID NO: 421), CeresAnnot_1475350 (SEQ ID NO: 423), GI_326490361 (SEQ ID NO: 424), GI_224140165 (SEQ ID NO: 425), GI_255577665 (SEQ ID NO: 426), CeresClone_1886384 (SEQ ID NO: 428), GI_255568402 (SEQ ID NO: 429), CeresClone_1942871 (SEQ ID NO: 431), GI_326527367 (SEQ ID NO: 432), GI_297816500 (SEQ ID NO: 433), GI_297810377 (SEQ ID NO: 434), GI_302762472 (SEQ ID NO: 435), GI_302815615 (SEQ ID NO: 436), GI_326525172 (SEQ ID NO: 437), GI_116787496 (SEQ ID NO: 438), GI_224029961 (SEQ ID NO: 439), GI_312282973 (SEQ ID NO: 440), GI_15232741 (SEQ ID NO: 441), GI_302806862 (SEQ ID NO: 442), GI_302772817 (SEQ ID NO: 443), GI_240254538 (SEQ ID NO: 444), GI_297833734 (SEQ ID NO: 445), GI_2739366 (SEQ ID NO: 446), GI_297825811 (SEQ ID NO: 447), and CeresClone_229668 (SEQ ID NO: 449). In some cases, a functional homolog of SEQ ID NO: 353 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 353. In some cases, a functional homolog of SEQ ID NO: 353 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 353 described above or set forth in the Sequence Listing The polypeptide set forth in SEQ ID NO: 353, or the functional homologs set forth above or in the Sequence Listing, can be truncated at the N- or C-terminus. In one embodiment, a functional homolog of SEQ ID NO:353 contains an N-terminal truncation. For example, a functional homolog of SEQ ID NO: 353 such as SEQ ID NO:366 can include amino acids aligning with residues 188 to 498 of SEQ ID NO: 353.

Figure 2B:
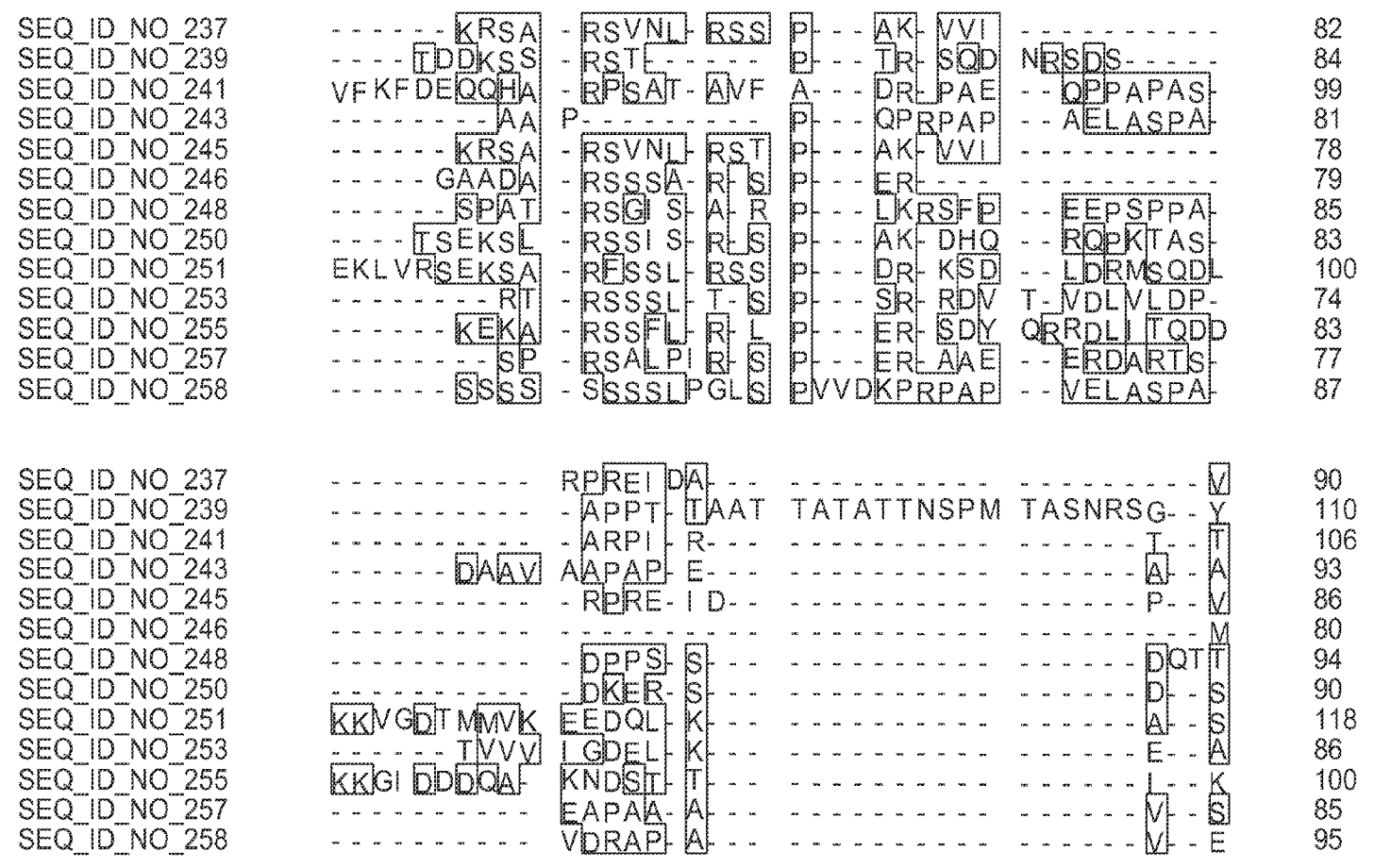

Examples of amino acid sequences of functional homologs of the polypeptide set forth in SEQ ID NO: 237 are provided in FIG. 2 and in the Sequence Listing. Such functional homologs include, for example, CeresClone_1847516 (SEQ ID NO: 239), CeresAnnot_8714481 (SEQ ID NO: 241), CeresClone_1961986 (SEQ ID NO: 243), CeresClone_1464596 (SEQ ID NO: 245), GI_225450173 (SEQ ID NO: 246), CeresClone_532446 (SEQ ID NO: 248), CeresAnnot_1493109 (SEQ ID NO: 250), GI_88866527 (SEQ ID NO: 251), CeresClone_1609861 (SEQ ID NO: 253), CeresClone_1620215 (SEQ ID NO: 255), CeresClone_1732772 (SEQ ID NO: 257), GI_295148935 (SEQ ID NO: 258), GI_125606142 (SEQ ID NO: 259), CeresClone_1040399 (SEQ ID NO: 261), CeresClone_1093691 (SEQ ID NO: 263), CeresClone_974539 (SEQ ID NO: 265), CeresClone_1832340 (SEQ ID NO: 267), CeresClone_1933211 (SEQ ID NO: 269), CeresClone_997558 (SEQ ID NO: 271), CeresAnnot_6041596 (SEQ ID NO: 273), GI_125564176 (SEQ ID NO: 274), CeresClone_1836064 (SEQ ID NO: 276), CeresClone_1909693 (SEQ ID NO: 278), CeresClone_1765346 (SEQ ID NO: 280), GI_125546008 (SEQ ID NO: 281), CeresClone_1950900 (SEQ ID NO: 283), GI_41350259 (SEQ ID NO: 284), GI_125588210 (SEQ ID NO: 285), CeresClone_1954395 (SEQ ID NO: 287), GI_18403408 (SEQ ID NO: 288), CeresClone_2010121 (SEQ ID NO: 290), CeresAnnot_6011486 (SEQ ID NO: 292), GI_25082726 (SEQ ID NO: 293), GI_113196593 (SEQ ID NO: 294), CeresClone_1843021 (SEQ ID NO: 296), CeresClone_1931194 (SEQ ID NO: 298), CeresClone_1850070 (SEQ ID NO: 300), CeresAnnot_6034955 (SEQ ID NO: 302), CeresAnnot_6119444 (SEQ ID NO: 304), CeresAnnot_6063956 (SEQ ID NO: 306), CeresAnnot_6015461 (SEQ ID NO: 308), CeresClone_696244 (SEQ ID NO: 310), CeresAnnot_1468973 (SEQ ID NO: 312), CeresClone_2019529 (SEQ ID NO: 314), CeresClone_1492169 (SEQ ID NO: 316), CeresClone_1652996 (SEQ ID NO: 318), CeresClone_100861292 (SEQ ID NO: 320), CeresClone_1875452 (SEQ ID NO: 322), CeresClone_296366 (SEQ ID NO: 324), CeresClone_1468822 (SEQ ID NO: 326), CeresClone_1793946 (SEQ ID NO: 328), GI_297829802 (SEQ ID NO: 329), CeresClone_1094610 (SEQ ID NO: 331), CeresClone_1084216 (SEQ ID NO: 333), CeresClone_100041169 (SEQ ID NO: 335), CeresClone_1619774 (SEQ ID NO: 337), GI_218685692 (SEQ ID NO: 338), GI_295148937 (SEQ ID NO: 339), CeresClone_1783953 (SEQ ID NO: 341), GI_242045152 (SEQ ID NO: 342), GI_223972713 (SEQ ID NO: 343), GI_326494504 (SEQ ID NO: 344), GI_326515226 (SEQ ID NO: 345), GI_163838754 (SEQ ID NO: 346), GI_163838756 (SEQ ID NO: 347), GI_163838762 (SEQ ID NO: 348), GI_326523409 (SEQ ID NO: 349), GI_255544230 (SEQ ID NO: 350), and GI_222822669 (SEQ ID NO: 351). In some cases, a functional homolog of SEQ ID NO: 237 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 237. In some cases, a functional homolog of SEQ ID NO: 237 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 237 described above or set forth in the Sequence Listing.

Figure 3A:
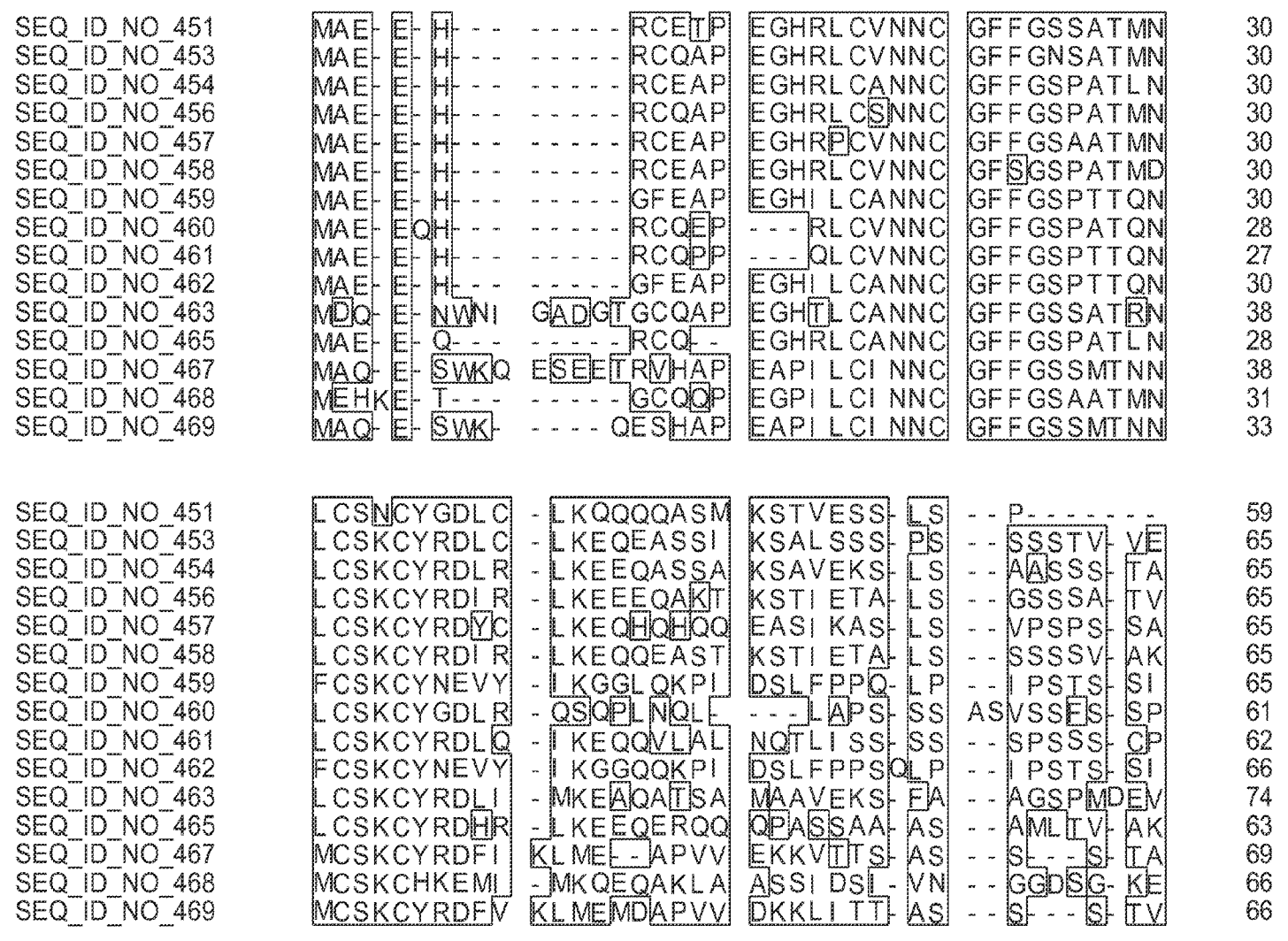
Figure 3B:
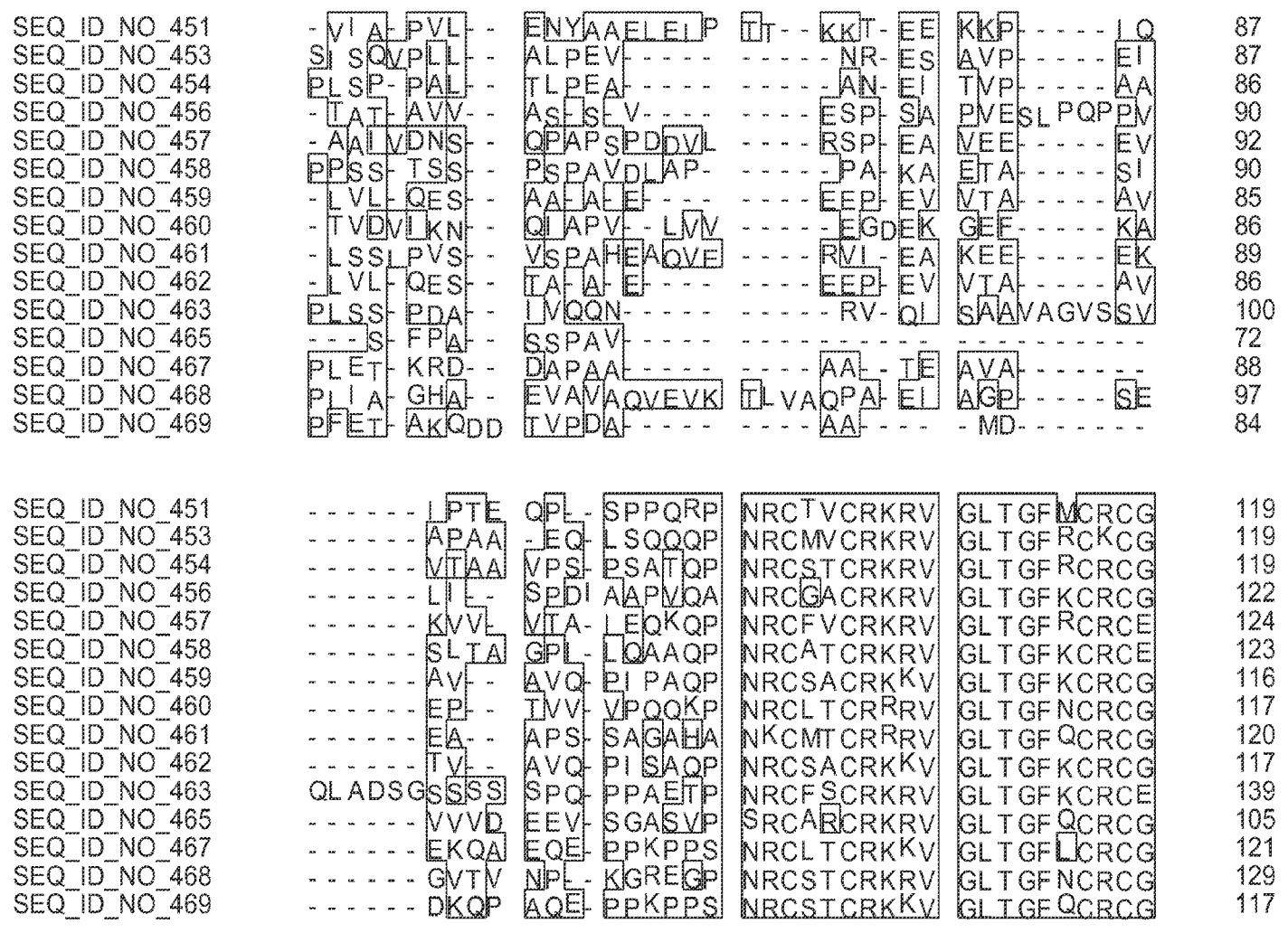

Examples of amino acid sequences of functional homologs of the polypeptide set forth in SEQ ID NO: 451 are provided in FIG. 3 and in the Sequence Listing. Such functional homologs include, for example, CeresClone_1931889 (SEQ ID NO: 453), GI_225440926 (SEQ ID NO: 454), CeresClone_708446 (SEQ ID NO: 456), GI_255575635 (SEQ ID NO: 457), GI_193237563 (SEQ ID NO: 458), GI_222822693 (SEQ ID NO: 459), GI_224103059 (SEQ ID NO: 460), GI_302398693 (SEQ ID NO: 461), GI_222822667 (SEQ ID NO: 462), GI_116778998 (SEQ ID NO: 463), CeresClone_1748922 (SEQ ID NO: 465), CeresClone_1775820 (SEQ ID NO: 467), GI_115468934 (SEQ ID NO: 468), GI_118424243 (SEQ ID NO: 469), GI_147783026 (SEQ ID NO: 470), GI_119367488 (SEQ ID NO: 471), GI_147860340 (SEQ ID NO: 472), GI_147792975 (SEQ ID NO: 473), GI_21359918 (SEQ ID NO: 474), GI_73951300 (SEQ ID NO: 475), GI_115477170 (SEQ ID NO: 476), CeresClone_1798756 (SEQ ID NO: 478), CeresClone_1918424 (SEQ ID NO: 480), CeresClone_1929645 (SEQ ID NO: 482), CeresClone_1845154 (SEQ ID NO: 484), CeresClone_1840507 (SEQ ID NO: 486), CeresClone_1853430 (SEQ ID NO: 488), CeresClone_1853189 (SEQ ID NO: 490), CeresClone_1808578 (SEQ ID NO: 492), CeresClone_1857508 (SEQ ID NO: 494), CeresClone_1946245 (SEQ ID NO: 496), CeresClone_1974721 (SEQ ID NO: 498), CeresClone_1940441 (SEQ ID NO: 500), CeresClone_1834813 (SEQ ID NO: 502), CeresClone_1848383 (SEQ ID NO: 504), CeresClone_1895219 (SEQ ID NO: 506), CeresClone_1866608 (SEQ ID NO: 508), CeresAnnot_1481252

(SEQ ID NO: 510), CeresAnnot_1474904 (SEQ ID NO: 512), CeresAnnot_1450673 (SEQ ID NO: 514), CeresAnnot_1437933 (SEQ ID NO: 516), CeresAnnot_1448174 (SEQ ID NO: 518), CeresAnnot_1447323 (SEQ ID NO: 520), CeresAnnot_1456578 (SEQ ID NO: 522), CeresAnnot_1491680 (SEQ ID NO: 524), CeresAnnot_1438851 (SEQ ID NO: 526), CeresAnnot_1440235 (SEQ ID NO: 528), CeresAnnot_1461453 (SEQ ID NO: 530), CeresAnnot_1468974 (SEQ ID NO: 532), CeresAnnot_1474244 (SEQ ID NO: 534), GI_15231686 (SEQ ID NO: 535), CeresClone_5522 (SEQ ID NO: 537), CeresClone_30543 (SEQ ID NO: 539), GI_14596167 (SEQ ID NO: 540), CeresClone_14203 (SEQ ID NO: 542), CeresClone_13832 (SEQ ID NO: 544), GI_15221329 (SEQ ID NO: 545), CeresClone_975913 (SEQ ID NO: 547), CeresClone_967417 (SEQ ID NO: 549), CeresClone_974951 (SEQ ID NO: 551), CeresClone_958471 (SEQ ID NO: 553), CeresClone_979956 (SEQ ID NO: 555), CeresClone_962327 (SEQ ID NO: 557), GI_119720772 (SEQ ID NO: 558), CeresClone_1614593 (SEQ ID NO: 560), CeresClone_567184 (SEQ ID NO: 562), CeresClone_580467 (SEQ ID NO: 564), CeresClone_1021029 (SEQ ID NO: 568), CeresClone_1072112 (SEQ ID NO: 570), CeresClone_481246 (SEQ ID NO: 572), CeresClone_1242573 (SEQ ID NO: 574), CeresClone_537439 (SEQ ID NO: 576), CeresClone_547126 (SEQ ID NO: 578), GI_92896423 (SEQ ID NO: 579), GI_124360119 (SEQ ID NO: 580), GI_122069751 (SEQ ID NO: 581), CeresClone_1030374 (SEQ ID NO: 583), CeresClone_1030540 (SEQ ID NO: 585), CeresClone_634261 (SEQ ID NO: 587), CeresClone_696374 (SEQ ID NO: 589), CeresClone_698573 (SEQ ID NO: 591), CeresClone_701370 (SEQ ID NO: 593), CeresClone_893059 (SEQ ID NO: 595), CeresClone_757664 (SEQ ID NO: 597), CeresClone_1387149 (SEQ ID NO: 599), CeresClone_1411371 (SEQ ID NO: 601), CeresClone_1380920 (SEQ ID NO: 603), CeresClone_1360570 (SEQ ID NO: 605), CeresClone_1458498 (SEQ ID NO: 607), GI_60202503 (SEQ ID NO: 608), CeresClone_1554153 (SEQ ID NO: 610), CeresClone_1362320 (SEQ ID NO: 612), CeresClone_1545291 (SEQ ID NO: 614), CeresClone_1589047 (SEQ ID NO: 616), CeresP Clone_101142707 (SEQ ID NO: 618), CeresClone_1433926 (SEQ ID NO: 620), CeresClone_1734621 (SEQ ID NO: 622), CeresClone_1731531 (SEQ ID NO: 624), GI_5031281 (SEQ ID NO: 625), CeresClone_1911017 (SEQ ID NO: 627), CeresClone_1955228 (SEQ ID NO: 629), CeresClone_1867313 (SEQ ID NO: 631), CeresClone_1955668 (SEQ ID NO: 633), CeresClone_1765871 (SEQ ID NO: 635), CeresClone_1870976 (SEQ ID NO: 637), CeresClone_1990071 (SEQ ID NO: 639), CeresClone_1965620 (SEQ ID NO: 641), CeresClone_1995041 (SEQ ID NO: 643), CeresClone_2015820 (SEQ ID NO: 645), CeresClone_1724157 (SEQ ID NO: 647), CeresClone_1724165 (SEQ ID NO: 649), GI_35187687 (SEQ ID NO: 650), GI_125556051 (SEQ ID NO: 651), GI_125561658 (SEQ ID NO: 652), GI_115470773 (SEQ ID NO: 653), GI_115444813 (SEQ ID NO: 654), GI_115446479 (SEQ ID NO: 655), GI_115455855 (SEQ ID NO: 656), GI_115479855 (SEQ ID NO: 657), GI_57899571 (SEQ ID NO: 658), CeresAnnot_6035031 (SEQ ID NO: 660), CeresAnnot_6111586 (SEQ ID NO: 662), CeresAnnot_6011488 (SEQ ID NO: 664), CeresAnnot_6063958 (SEQ ID NO: 666), CeresAnnot_6063957 (SEQ ID NO: 668), GI_38016527_*Gossypium_barbadense* (SEQ ID NO: 669), GI_75133829_*Oryza_sativa* (SEQ ID NO: 670), GI_125546011_*Oryza_sativa_indica* (SEQ ID NO: 671), GI_116778802_*Picea* (SEQ ID NO: 672), GI_116778893_*Picea* (SEQ ID NO: 673), GI_157849766_*Brassica rapa* (SEQ ID NO: 674), GI_159474166_*Chlamydomonas reinhardtii* (SEQ ID NO: 675), GI_168036656*Physcomitrella_patens* (SEQ ID NO: 676), GI_168053490_*Physcomitrella_patens* (SEQ ID NO: 677), CeresClone_100879386_*Zea_mays* (SEQ ID NO: 679), CeresClone_1738028_*Musa_acuminata* (SEQ ID NO: 681), CeresClone_2055733_*Miscanthus* (SEQ ID NO: 683), CeresClone_2056478_*Miscanthus* (SEQ ID NO: 685), GI_297823437 (SEQ ID NO: 686), GI_297816570 (SEQ ID NO: 687), CeresClone_1428270 (SEQ ID NO: 689), CeresClone_1447811 (SEQ ID NO: 691), CeresClone_1093477 (SEQ ID NO: 693), CeresClone_1260056 (SEQ ID NO: 695), GI_255565591 (SEQ ID NO: 696), CeresClone_1626661 (SEQ ID NO: 698), GI_222822665 (SEQ ID NO: 699), CeresClone_1842119 (SEQ ID NO: 701), GI_222822659 (SEQ ID NO: 702), GI_222822691 (SEQ ID NO: 703), GI_255544810 (SEQ ID NO: 704), GI_297847482 (SEQ ID NO: 705), GI_116791002 (SEQ ID NO: 706), GI_297809513 (SEQ ID NO: 707), CeresClone_100049493 (SEQ ID NO: 709), GI_222822685 (SEQ ID NO: 710), GI_301133546 (SEQ ID NO: 711), GI_225426659 (SEQ ID NO: 712), GI_297799728 (SEQ ID NO: 713), GI_15234402 (SEQ ID NO: 714), GI_254030287 (SEQ ID NO: 715), GI_222423788 (SEQ ID NO: 716), GI_222822679 (SEQ ID NO: 717), GI_222822653 (SEQ ID NO: 718), GI_302787300 (SEQ ID NO: 719), CeresClone_1955772 (SEQ ID NO: 721), GI_222822655 (SEQ ID NO: 722), GI_225435496 (SEQ ID NO: 723), GI_15235819 (SEQ ID NO: 724), GI_212275744 (SEQ ID NO: 725), GI_116787141 (SEQ ID NO: 726), GI_238575930 (SEQ ID NO: 727), GI_326515250 (SEQ ID NO: 728), GI_217075260 (SEQ ID NO: 729), GI_222622367 (SEQ ID NO: 730), GI_222822681 (SEQ ID NO: 731), GI_194692334 (SEQ ID NO: 732), GI_116791662 (SEQ ID NO: 733), GI_168007673 (SEQ ID NO: 734), GI_222822687 (SEQ ID NO: 735), GI_326499404 (SEQ ID NO: 736), GI_255628951 (SEQ ID NO: 737), GI_326496248 (SEQ ID NO: 738), GI_297849616 (SEQ ID NO: 739), GI_326489039 (SEQ ID NO: 740), CeresAnnot_8672029 (SEQ ID NO: 742), CeresClone_24253 (SEQ ID NO: 744), GI_297739707 (SEQ ID NO: 745), GI_217075452 (SEQ ID NO: 746), GI_168037934 (SEQ ID NO: 747), CeresClone_682858 (SEQ ID NO: 749), GI_222822689 (SEQ ID NO: 750), CeresAnnot_8644539 (SEQ ID NO: 752), GI_222822663 (SEQ ID NO: 753), GI_168018442 (SEQ ID NO: 754), GI_242081565 (SEQ ID NO: 755), CeresClone_1463779 (SEQ ID NO: 757), CeresAnnot_8713173 (SEQ ID NO: 759), GI_225455582 (SEQ ID NO: 760), GI_218189113 (SEQ ID NO: 761), GI_302755624 (SEQ ID NO: 762), CeresClone_1778054 (SEQ ID NO: 764), GI_302822895 (SEQ ID NO: 765), GI_255638082 (SEQ ID NO: 766), GI_297746352 (SEQ ID NO: 767), GI_255640538 (SEQ ID NO: 768), GI_13276697 (SEQ ID NO: 769), GI_255628269 (SEQ ID NO: 770), GI_297804888 (SEQ ID NO: 771), and GI_297736227 (SEQ ID NO: 772). In some cases, a functional homolog of SEQ ID NO: 451 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 451. In some cases, a functional homolog of SEQ ID NO: 451 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 451 described above or set forth in the Sequence Listing.

Examples of amino acid sequences of functional homologs of the polypeptide set forth in SEQ ID NO: 2 are provided in FIG. 4 and in the Sequence Listing. Such functional homologs include, for example, GI_239053200 (SEQ ID NO: 3), GI_242043390 (SEQ ID NO: 4), GI_4218535 (SEQ ID NO: 5), CeresAnnot_1706255 (SEQ ID NO: 7), GI_82400207 (SEQ ID NO: 8), GI_326514348 (SEQ ID NO: 9), GI_225435840 (SEQ ID NO: 10), GI_155965519 (SEQ ID NO: 11), GI_116791569 (SEQ ID NO: 12), GI_82568708 (SEQ ID NO: 13), GI_21105748 (SEQ ID NO: 14), GI_154362215 (SEQ ID NO: 15), CeresClone_1804251 (SEQ ID NO: 17), CeresClone_219367 (SEQ ID NO: 19), GI_226528637 (SEQ ID NO: 20), CeresClone_100906935 (SEQ ID NO: 22), CeresClone_1902485 (SEQ ID NO: 24), CeresClone_754901 (SEQ ID NO: 26), CeresClone_1804740 (SEQ ID NO: 28), GI_88770831 (SEQ ID NO: 29), CeresClone_100885834 (SEQ ID NO: 31), GI_125557725 (SEQ ID NO: 32), GI_115471229 (SEQ ID NO: 33), CeresAnnot_8631975 (SEQ ID NO: 35), GI_261349144 (SEQ ID NO: 36), CeresClone_261978 (SEQ ID NO: 38), CeresClone_1797688 (SEQ ID NO: 40), GI_300510868 (SEQ ID NO: 41), GI_51702426 (SEQ ID NO: 42), GI_219884691 (SEQ ID NO: 43), GI_292659262 (SEQ ID NO: 44), GI_82400213 (SEQ ID NO: 45), CeresClone_1566599 (SEQ ID NO: 47), GI_6730938 (SEQ ID NO: 48), GI_125528153 (SEQ ID NO: 49), GI_185179439 (SEQ ID NO: 50), CeresClone_1810747 (SEQ ID NO: 52), CeresClone_736293 (SEQ ID NO: 54), GI_292659260 (SEQ ID NO: 55), GI_242059063 (SEQ ID NO: 56), GI_82400209 (SEQ ID NO: 57), GI_223975401 (SEQ ID NO: 58), GI_138753440 (SEQ ID NO: 59), CeresClone_101131915 (SEQ ID NO: 61), CeresClone_100821085 (SEQ ID NO: 63), GI_302399001 (SEQ ID NO: 64), GI_225459603 (SEQ ID NO: 65), GI_302141792 (SEQ ID NO: 66), GI_125572421 (SEQ ID NO: 67), CeresClone_542522 (SEQ ID NO: 69), GI_195549547 (SEQ ID NO: 70), CeresClone_100961037 (SEQ ID NO: 72), GI_255640977 (SEQ ID NO: 73), CeresClone_1850651 (SEQ ID NO: 75), CeresAnnot_8462230 (SEQ ID NO: 77), GI_198400323 (SEQ ID NO: 78), GI_254034330 (SEQ ID NO: 79), CeresClone_100066176 (SEQ ID NO: 81), GI_206584339 (SEQ ID NO: 82), GI_224063050 (SEQ ID NO: 83), GI_312282805 (SEQ ID NO: 84), GI_255558632 (SEQ ID NO: 85), GI_21105734 (SEQ ID NO: 86), GI_116784797 (SEQ ID NO: 87), GI_187940307 (SEQ ID NO: 88), GI_184097796 (SEQ ID NO: 89), GI_222631638 (SEQ ID NO: 90), GI_116782512 (SEQ ID NO: 91), CeresClone_1220729 (SEQ ID NO: 93), GI_14485513 (SEQ ID NO: 94), CeresClone_514804 (SEQ ID NO: 96), GI_155008462 (SEQ ID NO: 97), GI_292659252 (SEQ ID NO: 98), GI_296044564 (SEQ ID NO: 99), GI_187940295 (SEQ ID NO: 100), CeresAnnot_8732688 (SEQ ID NO: 102), GI_302789271 (SEQ ID NO: 103), GI_206584337 (SEQ ID NO: 104), GI_326490045 (SEQ ID NO: 105), GI_31322570 (SEQ ID NO: 106), GI_168000027 (SEQ ID NO: 107), GI_297839605 (SEQ ID NO: 108), GI_62546185 (SEQ ID NO: 109), GI_147802535 (SEQ ID NO: 110), GI_302820063 (SEQ ID NO: 111), CeresClone_1769201 (SEQ ID NO: 113), CeresClone_477097 (SEQ ID NO: 115), CeresClone_1910025 (SEQ ID NO: 117), CeresAnnot_8669922 (SEQ ID NO: 119), GI_31322574 (SEQ ID NO: 120), GI_187940273 (SEQ ID NO: 121), GI_15223963 (SEQ ID NO: 122), CeresClone_100038358 (SEQ ID NO: 124), GI_148615629 (SEQ ID NO: 125), GI_225461361 (SEQ ID NO: 126), GI_255563837 (SEQ ID NO: 127), CeresClone_1727754 (SEQ ID NO: 129), CeresClone_1808216 (SEQ ID NO: 131), GI_195549534 (SEQ ID NO: 132), CeresAnnot_1466775 (SEQ ID NO: 134), CeresClone_23342 (SEQ ID NO: 136), GI_209171097 (SEQ ID NO: 137), GI_138753442 (SEQ ID NO: 138), CeresClone_1431867 (SEQ ID NO: 140), CeresClone_36478 (SEQ ID NO: 142), CeresClone_1864096 (SEQ ID NO: 144), CeresAnnot_1452119 (SEQ ID NO: 146), GI_302774106 (SEQ ID NO: 147), GI_171452372 (SEQ ID NO: 148), GI_297810999 (SEQ ID NO: 149), GI_21593134 (SEQ ID NO: 150), GI_125572883 (SEQ ID NO: 151), GI_242877145 (SEQ ID NO: 152), GI_125528621 (SEQ ID NO: 153), GI_115441473 (SEQ ID NO: 154), GI_31322566 (SEQ ID NO: 155), GI_224128213 (SEQ ID NO: 156), CeresClone_481915 (SEQ ID NO: 158), GI_31322580 (SEQ ID NO: 159), GI_311701727 (SEQ ID NO: 160), CeresClone_1434586 (SEQ ID NO: 162), GI_58013003 (SEQ ID NO: 163), GI_255586554 (SEQ ID NO: 164), CeresClone_1370400 (SEQ ID NO: 166), GI_312283489 (SEQ ID NO: 167), CeresAnnot_8453910 (SEQ ID NO: 169), CeresClone_1824711 (SEQ ID NO: 171), GI_57233056 (SEQ ID NO: 172), GI_167614348 (SEQ ID NO: 173), GI_296082607 (SEQ ID NO: 174), GI_62546187 (SEQ ID NO: 175), GI_62546189 (SEQ ID NO: 176), GI_31322568 (SEQ ID NO: 177), GI_66275774 (SEQ ID NO: 178), GI_225438363 (SEQ ID NO: 179), GI_124021383 (SEQ ID NO: 180), GI_224081060 (SEQ ID NO: 181), GI_255583865 (SEQ ID NO: 182), GI_217073174 (SEQ ID NO: 183), GI_168038326 (SEQ ID NO: 184), GI_295913643 (SEQ ID NO: 185), GI_31322578 (SEQ ID NO: 186), GI_118486672 (SEQ ID NO: 187), GI_15232604 (SEQ ID NO: 188), CeresAnnot_8683724 (SEQ ID NO: 190), GI_187940303 (SEQ ID NO: 191), GI_311780299 (SEQ ID NO: 192), GI_297830130 (SEQ ID NO: 193), GI_117586720 (SEQ ID NO: 194), GI_193237579 (SEQ ID NO: 195), CeresClone_1827014 (SEQ ID NO: 197), GI_31322576 (SEQ ID NO: 198), GI_255555947 (SEQ ID NO: 199), GI_125533643 (SEQ ID NO: 200), GI_118490007 (SEQ ID NO: 201), GI_21536744 (SEQ ID NO: 202), GI_302399025 (SEQ ID NO: 203), CeresClone_100046091 (SEQ ID NO: 205), CeresClone_20909 (SEQ ID NO: 207), CeresClone_1803889 (SEQ ID NO: 209), CeresAnnot_1456291 (SEQ ID NO: 211), GI_311976585 (SEQ ID NO: 212), GI_302399005 (SEQ ID NO: 213), GI_297744870 (SEQ ID NO: 214), GI_15223456 (SEQ ID NO: 215), GI_63252923 (SEQ ID NO: 216), GI_255636538 (SEQ ID NO: 217), GI_113205414 (SEQ ID NO: 218), GI_113205453 (SEQ ID NO: 219), GI_255635167 (SEQ ID NO: 220), GI_206584345 (SEQ ID NO: 221), CeresAnnot_867355 (SEQ ID NO: 223), GI_242877103 (SEQ ID NO: 224), GI_302793560 (SEQ ID NO: 225), CeresClone_38344 (SEQ ID NO: 227), GI_31322582 (SEQ ID NO: 228), GI_115336269 (SEQ ID NO: 229), GI_311115260 (SEQ ID NO: 230), GI_168054147 (SEQ ID NO: 231), GI_311115262 (SEQ ID NO: 232), GI_168034283 (SEQ ID NO: 233), GI_15148914 (SEQ ID NO: 234), and GI_302767458 (SEQ ID NO: 235). In some cases, a functional homolog of SEQ ID NO: 2 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2. In some cases, a functional homolog of SEQ ID NO: 2 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 2 described above or set forth in the Sequence Listing.

The identification of conserved regions in an aluminum tolerance-modulating polypeptide facilitates production of variants of aluminum tolerance-modulating polypeptides. Variants of aluminum tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIG. 1, FIG. 2, FIG. 3, or FIG. 4, and/or homologs identified in the Sequence Listing. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at a position marked by dashes, such a polypeptide has a length that is the sum of the amino acid residues in all conserved regions and all dashes.

C. Functional Homologs Identified by HMMER

In some embodiments, useful aluminum tolerance-modulating polypeptides include those that fit a Hidden Markov Model based on the polypeptides set forth in any one of FIGS. 1-4. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, --consistency REPS of 2; -ir, --iterative-refinement REPS of 100; -pre, --pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as hmmer.janelia.org; hmmer.wustl.edu; and fr.com/hmmer232/. Hmmbuild outputs the model as a text file.

The HMM for a group of functional homologs can be used to determine the likelihood that a candidate aluminum tolerance-modulating polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the ProbCons program. Nevertheless, such HMM bit score variation is minor.

The aluminum tolerance-modulating polypeptides discussed below fit the indicated HMM with an HMM bit score greater than to 65 (e.g., greater than 70, 80, 90, 100, 120, 140, 200, 300, 400, 500, 600, 700, 800, 900, 1000, 1500, or 2000). In some embodiments, the HMM bit score of an aluminum tolerance-modulating polypeptide discussed below is about 50%, 60%, 70%, 80%, 90%, or 95% of the HMM bit score of a functional homolog provided in the Sequence Listing of this application. In some embodiments, an aluminum tolerance-modulating polypeptide discussed below fits the indicated HMM with an HMM bit score greater than 210, and has a domain indicative of an aluminum tolerance-modulating polypeptide. In some embodiments, an aluminum tolerance-modulating polypeptide discussed below fits the indicated HMM with an HMM bit score greater than 210, and has 65% or greater sequence identity (e.g., 75%, 80%, 85%, 90%, 95%, or 100% sequence identity) to an amino acid sequence shown in any one of FIGS. 1-4.

Examples of polypeptides are shown in the sequence listing that have HMM bit scores greater than 159 (e.g., greater than 160, 170, 180, 190, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, or 1260) when fitted to an HMM generated from the amino acid sequences set forth in FIG. 1 are identified in the Sequence Listing of this application. Such polypeptides include, for example, SEQ ID NOs: 353, 355, 357, 358, 360, 362, 364, 366, 368, 369, 371, 373, 375, 376, 377, 378, 379, 380, 382, 384, 386, 388, 390, 392, 393, 395, 396, 397, 398, 399, 400, 401, 402, 404, 405, 407, 409, 411, 413, 414, 416, 418, 420, 421, 423, 424, 425, 426, 428, 429, 431, 432, 433, 434, 435, 436, 437, 438, 439, 440, 441, 442, 443, 444, 445, 446, 447, and 449.

Examples of polypeptides are shown in the sequence listing that have HMM bit scores greater than 83 (e.g., greater than 85, 90, 95, 100, 110, 120, 130, 140, 150, 175, 200, 225, 250, 275, or 300) when fitted to an HMM generated from the amino acid sequences set forth in FIG. 2 are identified in the Sequence Listing of this application. Such polypeptides include, for example, SEQ ID NOs: 237, 239, 241, 243, 245, 246, 248, 250, 251, 253, 255, 257, 258, 259, 261, 263, 265, 267, 269, 271, 273, 274, 276, 278, 280, 281, 283, 284, 285, 287, 288, 290, 292, 293, 294, 296, 298, 300, 302, 304, 306, 308, 310, 312, 314, 316, 318, 320, 322, 324, 326, 328, 329, 331, 333, 335, 337, 338, 339, 341, 342, 343, 344, 345, 346, 347, 348, 349, 350, and 351.

Examples of polypeptides are shown in the sequence listing that have HMM bit scores greater than 100 (e.g., greater than 110, 120, 130, 140, 150, 160, 170, 180, 190, 200, 225, 250, 275, 300, 325, 350, 375, 400, 410, 420, or 430) when fitted to an HMM generated from the amino acid sequences set forth in FIG. 3 are identified in the Sequence Listing of this application. Such polypeptides include, for example, SEQ ID NOs: 451, 453, 454, 456, 457, 458, 459, 460, 461, 462, 463, 465, 467, 468, 469, 470, 471, 472, 473, 474, 475, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 535, 537, 539, 540, 542, 544, 545, 547, 549, 551, 553, 555, 557, 558, 560, 562, 564, 568, 570, 572, 574, 576, 578, 579, 580, 581, 583, 585, 587, 589, 591, 593, 595, 597, 599, 601, 603, 605, 607, 608, 610, 612, 614, 616, 618, 620, 622, 624, 625, 627, 629, 631, 633, 635, 637, 639, 641, 643, 645, 647, 649, 650, 651, 652, 653, 654, 655, 656, 657, 658, 660, 662, 664, 666, 668, 669, 670, 671, 672, 673, 674, 675, 676, 677, 679, 681, 683, 685, 686, 687, 689, 691, 693, 695, 696, 698, 699, 701, 702, 703, 704, 705, 706, 707, 709, 710, 711, 712, 713, 714, 715, 716, 717, 718, 719, 721, 722, 723, 724, 725, 726, 727, 728, 729, 730, 731, 732, 733, 734, 735, 736, 737, 738, 739, 740, 742, 744, 745, 746, 747, 749, 750, 752, 753, 754, 755, 757, 759, 760, 761, 762, 764, 765, 766, 767, 768, 769, 770, 771, and 772.

Examples of polypeptides are shown in the sequence listing that have HMM bit scores greater than 204 (e.g., greater than 210, 220, 230, 240, 250, 260, 270, 280, 290, 300, 325, 350, 375, 400, 425, 450, 475, 500, 525, 550, 575, 600, 625, 650, 675, or 700) when fitted to an HMM generated from the amino acid sequences set forth in FIG. 4 are identified in the Sequence Listing of this application. Such polypeptides include, for example, SEQ ID NOs: 2, 3, 4, 5, 7, 8, 9, 10, 11, 12, 13, 14, 15, 17, 19, 20, 22, 24, 26, 28, 29, 31, 32, 33, 35, 36, 38, 40, 41, 42, 43, 44, 45, 47, 48, 49, 50, 52, 54, 55, 56, 57, 58, 59, 61, 63, 64, 65, 66, 67, 69, 70, 72, 73, 75, 77, 78, 79, 81, 82, 83, 84, 85, 86, 87, 88, 89, 90, 91, 93, 94, 96, 97, 98, 99, 100, 102, 103, 104, 105, 106, 107, 108, 109, 110, 111, 113, 115, 117, 119, 120, 121, 122, 124, 125, 126, 127, 129, 131, 132, 134, 136, 137, 138, 140, 142, 144, 146, 147, 148, 149, 150, 151, 152, 153, 154, 155, 156, 158, 159, 160, 162, 163, 164, 166, 167, 169, 171, 172, 173, 174, 175, 176, 177, 178, 179, 180, 181, 182, 183, 184, 185, 186, 187, 188, 190, 191, 192, 193, 194, 195, 197, 198, 199, 200, 201, 202, 203, 205, 207, 209, 211, 212, 213, 214, 215, 216, 217, 218, 219, 220, 221, 223, 224, 225, 227, 228, 229, 230, 231, 232, 233, 234, and 235.

D. Percent Identity

In some embodiments, an aluminum tolerance-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one of the amino acid sequences set forth in SEQ ID NOs: 2, 3, 4, 5, 7, 8, 9, 10, 11, 12, 13, 14, 15, 17, 19, 20, 22, 24, 26, 28, 29, 31, 32, 33, 35, 36, 38, 40, 41, 42, 43, 44, 45, 47, 48, 49, 50, 52, 54, 55, 56, 57, 58, 59, 61, 63, 64, 65, 66, 67, 69, 70, 72, 73, 75, 77, 78, 79, 81, 82, 83, 84, 85, 86, 87, 88, 89, 90, 91, 93, 94, 96, 97, 98, 99, 100, 102, 103, 104, 105, 106, 107, 108, 109, 110, 111, 113, 115, 117, 119, 120, 121, 122, 124, 125, 126, 127, 129, 131, 132, 134, 136, 137, 138, 140, 142, 144, 146, 147, 148, 149, 150, 151, 152, 153, 154, 155, 156, 158, 159, 160, 162, 163, 164, 166, 167, 169, 171, 172, 173, 174, 175, 176, 177, 178, 179, 180, 181, 182, 183, 184, 185, 186, 187, 188, 190, 191, 192, 193, 194, 195, 197, 198, 199, 200, 201, 202, 203, 205, 207, 209, 211, 212, 213, 214, 215, 216, 217, 218, 219, 220, 221, 223, 224, 225, 227, 228, 229, 230, 231, 232, 233, 234, 235, 237, 239, 241, 243, 245, 246, 248, 250, 251, 253, 255, 257, 258, 259, 261, 263, 265, 267, 269, 271, 273, 274, 276, 278, 280, 281, 283, 284, 285, 287, 288, 290, 292, 293, 294, 296, 298, 300, 302, 304, 306, 308, 310, 312, 314, 316, 318, 320, 322, 324, 326, 328, 329, 331, 333, 335, 337, 338, 339, 341, 342, 343, 344, 345, 346, 347, 348, 349, 350, 351, 353, 355, 357, 358, 360, 362, 364, 366, 368, 369, 371, 373, 375, 376, 377, 378, 379, 380, 382, 384, 386, 388, 390, 392, 393, 395, 396, 397, 398, 399, 400, 401, 402, 404, 405, 407, 409, 411, 413, 414, 416, 418, 420, 421, 423, 424, 425, 426, 428, 429, 431, 432, 433, 434, 435, 436, 437, 438, 439, 440, 441, 442, 443, 444, 445, 446, 447, 449, 451, 453, 454, 456, 457, 458, 459, 460, 461, 462, 463, 465, 467, 468, 469, 470, 471, 472, 473, 474, 475, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 535, 537, 539, 540, 542, 544, 545, 547, 549, 551, 553, 555, 557, 558, 560, 562, 564, 568, 570, 572, 574, 576, 578, 579, 580, 581, 583, 585, 587, 589, 591, 593, 595, 597, 599, 601, 603, 605, 607, 608, 610, 612, 614, 616, 618, 620, 622, 624, 625, 627, 629, 631, 633, 635, 637, 639, 641, 643, 645, 647, 649, 650, 651, 652, 653, 654, 655, 656, 657, 658, 660, 662, 664, 666, 668, 669, 670, 671, 672, 673, 674, 675, 676, 677, 679, 681, 683, 685, 686, 687, 689, 691, 693, 695, 696, 698, 699, 701, 702, 703, 704, 705, 706, 707, 709, 710, 711, 712, 713, 714, 715, 716, 717, 718, 719, 721, 722, 723, 724, 725, 726, 727, 728, 729, 730, 731, 732, 733, 734, 735, 736, 737, 738, 739, 740, 742, 744, 745, 746, 747, 749, 750, 752, 753, 754, 755, 757, 759, 760, 761, 762, 764, 765, 766, 767, 768, 769, 770, 771, and 772. Polypeptides having such a percent sequence identity often have a domain indicative of an aluminum tolerance-modulating polypeptide and/or have an HMM bit score that is greater than 65, as discussed above. Amino acid sequences of aluminum tolerance-modulating polypeptides having at least 80% sequence identity to one of the amino acid sequences set forth in SEQ ID NOs: 2, 3, 4, 5, 7, 8, 9, 10, 11, 12, 13, 14, 15, 17, 19, 20, 22, 24, 26, 28, 29, 31, 32, 33, 35, 36, 38, 40, 41, 42, 43, 44, 45, 47, 48, 49, 50, 52, 54, 55, 56, 57, 58, 59, 61, 63, 64, 65, 66, 67, 69, 70, 72, 73, 75, 77, 78, 79, 81, 82, 83, 84, 85, 86, 87, 88, 89, 90, 91, 93, 94, 96, 97, 98, 99, 100, 102, 103, 104, 105, 106, 107, 108, 109, 110, 111, 113, 115, 117, 119, 120, 121, 122, 124, 125, 126, 127, 129, 131, 132, 134, 136, 137, 138, 140, 142, 144, 146, 147, 148, 149, 150, 151, 152, 153, 154, 155, 156, 158, 159, 160, 162, 163, 164, 166, 167, 169, 171, 172, 173, 174, 175, 176, 177, 178, 179, 180, 181, 182, 183, 184, 185, 186, 187, 188, 190, 191, 192, 193, 194, 195, 197, 198, 199, 200, 201, 202, 203, 205, 207, 209, 211, 212, 213, 214, 215, 216, 217, 218, 219, 220, 221, 223, 224, 225, 227, 228, 229, 230, 231, 232, 233, 234, 235, 237, 239, 241, 243, 245, 246, 248, 250, 251, 253, 255, 257, 258, 259, 261, 263, 265, 267, 269, 271, 273, 274, 276, 278, 280, 281, 283, 284, 285, 287, 288, 290, 292, 293, 294, 296, 298, 300, 302, 304, 306, 308, 310, 312, 314, 316, 318, 320, 322, 324, 326, 328, 329, 331, 333, 335, 337, 338, 339, 341, 342, 343, 344, 345, 346, 347, 348, 349, 350, 351, 353, 355, 357, 358, 360, 362, 364, 366, 368, 369, 371, 373, 375, 376, 377, 378, 379, 380, 382, 384, 386, 388, 390, 392, 393, 395, 396, 397, 398, 399, 400, 401, 402, 404, 405, 407, 409, 411, 413, 414, 416, 418, 420, 421, 423, 424, 425, 426, 428, 429, 431, 432, 433, 434, 435, 436, 437, 438, 439, 440, 441, 442, 443, 444, 445, 446, 447, 449, 451, 453, 454, 456, 457, 458, 459, 460, 461, 462, 463, 465, 467, 468, 469, 470, 471, 472, 473, 474, 475, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 535, 537, 539, 540, 542, 544, 545, 547, 549, 551, 553, 555, 557, 558, 560, 562, 564, 568, 570, 572, 574, 576, 578, 579, 580, 581, 583, 585, 587, 589, 591, 593, 595, 597, 599, 601, 603, 605, 607, 608, 610, 612, 614, 616, 618, 620, 622, 624, 625, 627, 629, 631, 633, 635, 637, 639, 641, 643, 645, 647, 649, 650, 651, 652, 653, 654, 655, 656, 657, 658, 660, 662, 664, 666, 668, 669, 670, 671, 672, 673, 674, 675, 676, 677, 679, 681, 683, 685, 686, 687, 689, 691, 693, 695, 696, 698, 699, 701, 702, 703, 704, 705, 706, 707, 709, 710, 711, 712, 713, 714, 715, 716, 717, 718, 719, 721, 722, 723, 724, 725, 726, 727, 728, 729, 730, 731, 732, 733, 734, 735, 736, 737, 738, 739, 740, 742, 744, 745, 746, 747, 749, 750, 752, 753, 754, 755, 757, 759, 760, 761, 762, 764, 765, 766, 767, 768, 769, 770, 771, and 772 are provided in FIGS. 1-4 and in the Sequence Listing.

"Percent sequence identity" refers to the degree of sequence identity between any given reference sequence, e.g., SEQ ID NO: 1, and a candidate aluminum tolerance-modulating sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., *Nucleic Acids Res.,* 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, an aluminum tolerance-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 353. Amino acid sequences of polypeptides having greater than 45% sequence identity to the polypeptide set forth in SEQ ID NO: 353 are provided in FIG. 1 and in the Sequence Listing.

In some cases, an aluminum tolerance-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 237. Amino acid sequences of polypeptides having greater than 45% sequence identity to the polypeptide set forth in SEQ ID NO: 237 are provided in FIG. 2 and in the Sequence Listing.

In some cases, an aluminum tolerance-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 451. Amino acid sequences of polypeptides having greater than 45% sequence identity to the polypeptide set forth in SEQ ID NO: 451 are provided in FIG. 3 and in the Sequence Listing.

In some cases, an aluminum tolerance-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2. Amino acid sequences of polypeptides having greater than 45% sequence identity to the polypeptide set forth in SEQ ID NO: 2 are provided in FIG. 4 and in the Sequence Listing.

E. Other Sequences

It should be appreciated that an aluminum tolerance-modulating polypeptide can include additional amino acids that are not involved in aluminum tolerance modulation, and thus such a polypeptide can be longer than would otherwise be the case. For example, an aluminum tolerance-modulating polypeptide can include a purification tag, a chloroplast transit peptide, a mitochondrial transit peptide, an amyloplast peptide, or a leader sequence added to the amino or carboxy terminus. In some embodiments, an aluminum tolerance-modulating polypeptide includes an amino acid sequence that functions as a reporter, e.g., a green fluorescent protein or yellow fluorescent protein.

III. Nucleic Acids

Nucleic acids described herein include nucleic acids that are effective to modulate aluminum tolerance levels when transcribed in a plant or plant cell. Such nucleic acids include, without limitation, those that encode an aluminum tolerance-modulating polypeptide and those that can be used to inhibit expression of an aluminum tolerance-modulating polypeptide via a nucleic acid based method.

A. Nucleic Acids Encoding Aluminum Tolerance-Modulating Polypeptides

Nucleic acids encoding aluminum tolerance-modulating polypeptides are described herein. Examples of such nucleic acids include SEQ ID NOs: 1, 6, 16, 18, 21, 23, 25, 27, 30, 34, 37, 39, 46, 51, 53, 60, 62, 68, 71, 74, 76, 80, 92, 95, 101, 112, 114, 116, 118, 123, 128, 130, 133, 135, 139, 141, 143, 145, 157, 161, 165, 168, 170, 189, 196, 204, 206, 208, 210, 222, 226, 236, 238, 240, 242, 244, 247, 249, 252, 254, 256, 260, 262, 264, 266, 268, 270, 272, 275, 277, 279, 282, 286, 289, 291, 295, 297, 299, 301, 303, 305, 307, 309, 311, 313, 315, 317, 319, 321, 323, 325, 327, 330, 332, 334, 336, 340, 352, 354, 356, 359, 361, 363, 365, 367, 370, 372, 374, 381, 383, 385, 387, 389, 391, 394, 403, 406, 408, 410, 412, 415, 417, 419, 422, 427, 430, 448, 450, 452, 455, 464, 466, 477, 479, 481, 483, 485, 487, 489, 491, 493, 495, 497, 499, 501, 503, 505, 507, 509, 511, 513, 515, 517, 519, 521, 523, 525, 527, 529, 531, 533, 536, 538, 541, 543, 546, 548, 550, 552, 554, 556, 559, 561, 563, 567, 569, 571, 573, 575, 577, 582, 584, 586, 588, 590, 592, 594, 596, 598, 600, 602, 604, 606, 609, 611, 613, 615, 617, 619, 621, 623, 626, 628, 630, 632, 634, 636, 638, 640, 642, 644, 646, 648, 659, 661, 663, 665, 667, 678, 680, 682, 684, 688, 690, 692, 694, 697, 700, 708, 720, 741, 743, 748, 751, 756, 758, and 763 as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NOs: 1, 6, 16, 18, 21, 23, 25, 27, 30, 34, 37, 39, 46, 51, 53, 60, 62, 68, 71, 74, 76, 80, 92, 95, 101, 112, 114, 116, 118, 123, 128, 130, 133, 135, 139, 141, 143, 145, 157, 161, 165, 168, 170, 189, 196, 204, 206, 208, 210, 222, 226, 236, 238, 240, 242, 244, 247, 249, 252, 254, 256, 260, 262, 264, 266, 268, 270, 272, 275, 277, 279, 282, 286, 289, 291, 295, 297, 299, 301, 303, 305, 307, 309, 311, 313, 315, 317, 319, 321, 323, 325, 327, 330, 332, 334, 336, 340, 352, 354, 356, 359, 361, 363, 365, 367, 370, 372, 374, 381, 383, 385, 387, 389, 391, 394, 403, 406, 408, 410, 412, 415, 417, 419, 422, 427, 430, 448, 450, 452, 455, 464, 466, 477, 479, 481, 483, 485, 487, 489, 491, 493, 495, 497, 499, 501, 503, 505, 507, 509, 511, 513, 515, 517, 519, 521, 523, 525, 527, 529, 531, 533, 536, 538, 541, 543, 546, 548, 550, 552, 554, 556, 559, 561, 563, 567, 569, 571, 573, 575, 577, 582, 584, 586, 588, 590, 592, 594, 596, 598, 600, 602, 604, 606, 609, 611, 613, 615, 617, 619, 621, 623, 626, 628, 630, 632, 634, 636, 638, 640, 642, 644, 646, 648, 659, 661, 663, 665, 667, 678, 680, 682, 684, 688, 690, 692, 694, 697, 700, 708, 720, 741, 743, 748, 751, 756, 758, and 763.

An aluminum tolerance-modulating nucleic acid can comprise the nucleotide sequence set forth in SEQ ID NO:352. Alternatively, an aluminum tolerance-modulating nucleic acid can be a variant of the nucleic acid having the nucleotide sequence set forth in SEQ ID NO: 352. For example, an aluminum tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 352.

An aluminum tolerance-modulating nucleic acid can comprise the nucleotide sequence set forth in SEQ ID NO: 236. Alternatively, an aluminum tolerance-modulating nucleic acid can be a variant of the nucleic acid having the nucleotide sequence set forth in SEQ ID NO: 236. For example, an aluminum tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 236.

An aluminum tolerance-modulating nucleic acid can comprise the nucleotide sequence set forth in SEQ ID NO: 450. Alternatively, an aluminum tolerance-modulating nucleic acid can be a variant of the nucleic acid having the nucleotide sequence set forth in SEQ ID NO: 450. For example, an aluminum tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 450.

An aluminum tolerance-modulating nucleic acid can comprise the nucleotide sequence set forth in SEQ ID NO: 1. Alternatively, an aluminum tolerance-modulating nucleic acid can be a variant of the nucleic acid having the nucleotide sequence set forth in SEQ ID NO: 1. For example, an aluminum tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of an Aluminum Tolerance-Modulating Polypeptide A nucleic acid encoding one of the aluminum tolerance-modulating polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular aluminum tolerance-modulating polypeptide; i.e., for many amino acids, there is more than one nucleotide triplet that serves as the codon for the amino acid. Thus, codons in the coding sequence for a given aluminum tolerance-modulating polypeptide can be modified such that optimal expression in a particular plant species is obtained, using appropriate codon bias tables for that species.

In some cases, expression of an aluminum tolerance-modulating polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii Inhibition of Expression of an Aluminum Tolerance-Modulating Polypeptide

Polynucleotides and recombinant constructs described herein can be used to inhibit expression of an aluminum tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); and *Nature Reviews RNA interference collection*, October 2005 on the World Wide Web at nature-.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding aluminum tolerance-modulating polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid need not be the entire sequence of the gene to be repressed, but typically will be substantially complementary to at least a portion of the sense strand of the gene to be repressed.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of an aluminum tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the aluminum tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding an aluminum tolerance-modulating polypeptide, and the other strand of the stem portion of the double stranded RNA comprises a sequence that is similar or identical to the sequence that is complementary to the 3' or 5' untranslated region, respectively, or a fragment thereof, of the mRNA encoding the aluminum tolerance-modulating polypeptide. In other embodiments, one strand of the stem portion of a double stranded RNA comprises a sequence that is similar or identical to the sequence of an intron, or a fragment thereof, in the pre-mRNA encoding an aluminum tolerance-modulating polypeptide, and the other strand of the stem portion comprises a sequence that is similar or identical to the sequence that is complementary to the sequence of the intron, or a fragment thereof, in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence, or a fragment thereof, of an aluminum tolerance-modulating polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding an aluminum tolerance-modulating polypeptide, or a fragment of such sequences. In some embodiments, the sense or antisense sequence is identical or complementary to a sequence of the regulatory region that drives transcription of the gene encoding an aluminum tolerance-modulating polypeptide. In each case, the sense sequence is the sequence that is complementary to the antisense sequence.

The sense and antisense sequences can be a length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding an aluminum tolerance-modulating polypeptide described herein. The sense sequence complementary to the antisense sequence can be a sequence present within the mRNA of the aluminum tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have a suitable arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences or the left and right border-like sequences of the P-DNA flank, or are on either side of, the nucleic acid. See, U.S. Patent Publication No. 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, Antisense *Nucleic Acid Drug Dev.*, 7:187-195 (1997); Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

C. Constructs/Vectors

Recombinant constructs provided herein can be used to transform plants or plant cells in order to modulate aluminum tolerance levels. A recombinant nucleic acid construct can comprise a nucleic acid encoding an aluminum tolerance-modulating polypeptide as described herein, operably linked to a regulatory region suitable for expressing the aluminum tolerance-modulating polypeptide in the plant or cell. Thus, a nucleic acid can comprise a coding sequence that encodes an aluminum tolerance-modulating polypeptide as set forth in SEQ ID NOs: 2, 3, 4, 5, 7, 8, 9, 10, 11, 12, 13, 14, 15, 17, 19, 20, 22, 24, 26, 28, 29, 31, 32, 33, 35, 36, 38, 40, 41, 42, 43, 44, 45, 47, 48, 49, 50, 52, 54, 55, 56, 57, 58, 59, 61, 63, 64, 65, 66, 67, 69, 70, 72, 73, 75, 77, 78, 79, 81, 82, 83, 84, 85, 86, 87, 88, 89, 90, 91, 93, 94, 96, 97, 98, 99, 100, 102, 103, 104, 105, 106, 107, 108, 109, 110, 111, 113, 115, 117, 119, 120, 121, 122, 124, 125, 126, 127, 129, 131, 132, 134, 136, 137, 138, 140, 142, 144, 146, 147, 148, 149, 150, 151, 152, 153, 154, 155, 156, 158, 159, 160, 162, 163, 164, 166, 167, 169, 171, 172, 173, 174, 175, 176, 177, 178, 179, 180, 181, 182, 183, 184, 185, 186, 187, 188, 190, 191, 192, 193, 194, 195, 197, 198, 199, 200, 201, 202, 203, 205, 207, 209, 211, 212, 213, 214, 215, 216, 217, 218, 219, 220, 221, 223, 224, 225, 227, 228, 229, 230, 231, 232, 233, 234, 235, 237, 239, 241, 243, 245, 246, 248, 250, 251, 253, 255, 257, 258, 259, 261, 263, 265, 267, 269, 271, 273, 274, 276, 278, 280, 281, 283, 284, 285, 287, 288, 290, 292, 293, 294, 296, 298, 300, 302, 304, 306, 308, 310, 312, 314, 316, 318, 320, 322, 324, 326, 328, 329, 331, 333, 335, 337, 338, 339, 341, 342, 343, 344, 345, 346, 347, 348, 349, 350, 351, 353, 355, 357, 358, 360, 362, 364, 366, 368, 369, 371, 373, 375, 376, 377, 378, 379, 380, 382, 384, 386, 388, 390, 392, 393, 395, 396, 397, 398, 399, 400, 401, 402, 404, 405, 407, 409, 411, 413, 414, 416, 418, 420, 421, 423, 424, 425, 426, 428, 429, 431, 432, 433, 434, 435, 436, 437, 438, 439, 440, 441, 442, 443, 444, 445, 446, 447, 449, 451, 453, 454, 456, 457, 458, 459, 460, 461, 462, 463, 465, 467, 468, 469, 470, 471, 472, 473, 474, 475, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 535, 537, 539, 540, 542, 544, 545, 547, 549, 551, 553, 555, 557, 558, 560, 562, 564, 568, 570, 572, 574, 576, 578, 579, 580, 581, 583, 585, 587, 589, 591, 593, 595, 597, 599, 601, 603, 605, 607, 608, 610, 612, 614, 616, 618, 620, 622, 624, 625, 627, 629, 631, 633, 635, 637, 639, 641, 643, 645, 647, 649, 650, 651, 652, 653, 654, 655, 656, 657, 658, 660, 662, 664, 666, 668, 669, 670, 671, 672, 673, 674, 675, 676, 677, 679, 681, 683, 685, 686, 687, 689, 691, 693, 695, 696, 698, 699, 701, 702, 703, 704, 705, 706, 707, 709, 710, 711, 712, 713, 714, 715, 716, 717, 718, 719, 721, 722, 723, 724, 725, 726, 727, 728, 729, 730, 731, 732, 733, 734, 735, 736, 737, 738, 739, 740, 742, 744, 745, 746, 747, 749, 750, 752, 753, 754, 755, 757, 759, 760, 761, 762, 764, 765, 766, 767, 768, 769, 770, 771, and 772. Examples of nucleic acids encoding aluminum tolerance-modulating polypeptides are set forth in SEQ ID NOs: 1, 6, 16, 18, 21, 23, 25, 27, 30, 34, 37, 39, 46, 51, 53, 60, 62, 68, 71, 74, 76, 80, 92, 95, 101, 112, 114, 116, 118, 123, 128, 130, 133, 135, 139, 141, 143, 145, 157, 161, 165, 168, 170, 189, 196, 204, 206, 208, 210, 222, 226, 236, 238, 240, 242, 244, 247, 249, 252, 254, 256, 260, 262, 264, 266, 268, 270, 272, 275, 277, 279, 282, 286, 289, 291, 295, 297, 299, 301, 303, 305, 307, 309, 311, 313, 315, 317, 319, 321, 323, 325, 327, 330, 332, 334, 336, 340, 352, 354, 356, 359, 361, 363, 365, 367, 370, 372, 374, 381, 383, 385, 387, 389, 391, 394, 403, 406, 408, 410, 412, 415, 417, 419, 422, 427, 430, 448, 450, 452, 455, 464, 466, 477, 479, 481, 483, 485, 487, 489, 491, 493, 495, 497, 499, 501, 503, 505, 507, 509, 511, 513, 515, 517, 519, 521, 523, 525, 527, 529, 531, 533, 536, 538, 541, 543, 546, 548, 550, 552, 554, 556, 559, 561, 563, 567, 569, 571, 573, 575, 577, 582, 584, 586, 588, 590, 592, 594, 596, 598, 600, 602, 604, 606, 609, 611, 613, 615, 617, 619, 621, 623, 626, 628, 630, 632, 634, 636, 638, 640, 642, 644, 646, 648, 659, 661, 663, 665, 667, 678, 680, 682, 684, 688, 690, 692, 694, 697, 700, 708, 720, 741, 743, 748, 751, 756, 758, and 763, or in the Sequence Listing. The aluminum tolerance-modulating polypeptide encoded by a recombinant nucleic acid can be a native aluminum tolerance-modulating polypeptide, or can be heterologous to the cell. In some cases, the recombinant construct contains a nucleic acid that inhibits expression of an aluminum tolerance-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen® (Madison, Wis.), Clontech® (Palo Alto, Calif.), Stratagene® (La Jolla, Calif.), and Invitrogen/Life Technologies® (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al., *Plant Cell*, 1:855-866 (1989); Bustos et al., *Plant Cell*, 1:839-854 (1989); Green et al., *EMBO J.*, 7:4035-4044 (1988); Meier et al., *Plant Cell*, 3:309-316 (1991); and Zhang et al., *Plant Physiology*, 110:1069-1079 (1996).

Examples of various classes of regulatory regions are described below. Some of the regulatory regions indicated below as well as additional regulatory regions are described in more detail in U.S. patent application Ser. Nos. 60/505,689; 60/518,075; 60/544,771; 60/558,869; 60/583,691; 60/619,181; 60/637,140; 60/757,544; 60/776,307; 10/957,569; 11/058,689; 11/172,703; 11/208,308; 11/274,890; 60/583,609; 60/612,891; 11/097,589; 11/233,726; 11/408, 791; 11/414,142; 10/950,321; 11/360,017; PCT/US05/011105; PCT/US05/23639; PCT/US05/034308; PCT/US05/034343; and PCT/US06/038236; PCT/US06/040572; PCT/US07/62762; PCT/US2009/032485; and PCT/US2009/038792.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

Another example of a broad promoter is the sequence of regulatory region PD3141 set forth in the sequence listing of PCT/US2009/032485. Therein, the expression pattern of the PD3141 regulatory region is described for TO rice plants overexpressing a construct comprising PD3141 driving expression of EGFP. In seedlings, expression was observed in: Tiller: not-specific; Main culm: not-specific; Root: not-specific; Leaf: not-specific; and Meristem: not-specific. In mature plants, expression was observed in: Main culm: bundle sheath, endodermis, epidermis, internode, ligule, node, pericycle, phloem, sclerenchyma layer, vasculature, xylem; Root: cortex, vascular; Panicle: flag leaf, ovary, peduncle, primary branch, rachilla, rachis, spiklet; Spiklet: flag leaf, floret(palea), lemma, ovule, pedicle, pollen, seed, stigma; Leaf: epidermis, leaf blade, leaf sheath, mesophyll; and Meristem: floral meristem, shoot apical meristem, vegetative meristem.

Another example of a broad promoter is the sequence of regulatory region p326 set forth in the sequence listing of U.S. application Ser. No. 10/981,334. Therein, the expression pattern of the p326 regulatory region is described for *Arabidopsis* plants. p326 expressed throughout most mature tissues screened. Expression was somewhat higher in epidermal, vascular and photosynthetic tissue of seedling. Lines characterized went through several generations.

Another example of a broad promoter is the sequence of regulatory region PD2995 (a 600 bp version of p326) set forth in the sequence listing of PCT/US2009/32485. In TO rice plants, PD2995 expresses very weakly throughout all tissues of the plant in both seedling and mature stages. Strongest expression detected in root tissue and embryo.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA,* 86:7890-7894 (1989)), root cell specific promoters reported by Conkling et al., *Plant Physiol.,* 93:1203-1211 (1990), and the tobacco RD2 promoter.

Another example of a root promoter is the sequence of regulatory region PD3561 set forth in the sequence listing of PCT/US2009/038792. Therein, the expression pattern of the PD3561 regulatory region is described for TO rice plants overexpressing a construct comprising PD3561 driving expression of EGFP. Expression was observed in roots of seedlings in the cortex, epidermis, and vascular tissues. In mature plants, expression was observed strongly throughout the root with the exception of the root cap and in the cortex, epidermis, and vascular tissues.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., *Plant Cell,* 1(9):839-853 (1989)), the soybean trypsin inhibitor promoter (Riggs et al., *Plant Cell,* 1(6):609-621 (1989)), the ACP promoter (Baerson et al., *Plant Mol. Biol.,* 22(2):255-267 (1993)), the stearoyl-ACP desaturase promoter (Slocombe et al., *Plant Physiol.,* 104(4):167-176 (1994)), the soybean α' subunit of β-conglycinin promoter (Chen et al., *Proc. Natl. Acad. Sci.*

USA, 83:8560-8564 (1986)), the oleosin promoter (Hong et al., *Plant Mol. Biol.*, 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.*, 13:5829-5842 (1993)), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmycl (see, Urao, *Plant Mol. Biol.*, 32:571-57 (1996); Conceicao, *Plant*, 5:493-505 (1994)); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan, *Genetics*, 142:1009-1020 (1996)); maize Cat3 (see, GenBank No. L05934; Abler, *Plant Mol. Biol.*, 22:10131-1038 (1993)). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* 20:647-654 (2001)), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104:997-1006 (1994)), the cab1R promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcb1*2 promoter (Cerdan et al., *Plant Mol. Biol.*, 33:245-255 (1997)), the *Arabidopsis thaliana* SUC2 sucrose-H+ symporter promoter (Truernit et al., *Planta*, 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, Plant Cell, 3(10):1051-1061 (1991)), the *Commelina* yellow mottle virus (CoYMV) promoter (Medberry et al., *Plant Cell*, 4(2):185-192 (1992)), and the rice tungro bacilliform virus (RTBV) promoter (Dai et al., *Proc. Natl. Acad. Sci. USA*, 101(2):687-692 (2004)).

ix. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) Nature Biotech 17: 287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Stem Promoters

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and CryIA(b) and CryIA(c) (Braga et al. 2003, Journal of New Seeds 5:209-221).

xii. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xiii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding an aluminum tolerance-modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

IV. Transgenic Plants and Plant Cells

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous aluminum tolerance-modulating polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of an aluminum tolerance-modulating polypeptide or nucleic acid. In some embodiments, a population of plants can be selected that has increased tolerance to elevated levels of $Al^{3+}$ in soil without increased tolerance to drought or elevated saline levels. Plant species vary in their capacity to tolerate salinity. "Salinity" refers to a set of environmental conditions under which a plant will begin to suffer the effects of elevated salt concentration, such as ion imbalance, decreased stomatal conductance, decreased photosynthesis, decreased growth rate, increased cell death, loss of turgor (wilting), or ovule abortion. For these reasons, plants experiencing salinity stress typically exhibit a significant reduction in biomass and/or yield.

Physical and biochemical methods can be used to identify expression levels. These include Southern analysis or PCR amplification for detection of a polynucleotide; Northern blots, 51 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as increased tolerance to elevated levels of aluminum. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in an aluminum tolerance level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

Suitable species include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cordgrass), *Medicago sativa* (alfalfa), *Arundo donax* (giant reed), *Secale cereale* (rye), *Salix* spp. (willow), *Eucalyptus* spp. (*eucalyptus*), *Triticosecale* (*triticum*—wheat X rye) and bamboo.

Suitable species also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), and *Brassica juncea.*

Suitable species also include *Beta vulgaris* (sugarbeet), and *Manihot esculenta* (cassava)

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii,* and *Tanacetum parthenium.*

Suitable species also include *Parthenium argentatum* (guayule), *Hevea* spp. (rubber), *Mentha spicata* (mint), *Mentha piperita* (mint), *Bixa orellana,* and *Alstroemeria* spp.

Suitable species also include Rosa spp. (rose), *Dianthus caryophyllus* (carnation), *Petunia* spp. (*petunia*) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), Acer spp. (maple), *Hordeum vulgare* (barley), *Poa pratensis* (bluegrass), *Lolium* spp. (ryegrass) and *Phleum pratense* (timothy).

In some embodiments, a suitable species can be a wild, weedy, or cultivated *Pennisetum* species such as, but not limited to, *Pennisetum alopecuroides, Pennisetum arnhemicum, Pennisetum caffrum, Pennisetum clandestinum, Pennisetum divisum, Pennisetum glaucum, Pennisetum latifolium, Pennisetum macrostachyum, Pennisetum macrourum, Pennisetum orientale, Pennisetum pedicellatum, Pennisetum polystachion, Pennisetum polystachion* ssp. *Setosum, Pennisetum purpureum, Pennisetum setaceum, Pennisetum subangustum, Pennisetum typhoides, Pennisetum villosum,* or hybrids thereof (e.g., *Pennisetum purpureum* x *Pennisetum typhoidum*).

In some embodiments, a suitable species can be a wild, weedy, or cultivated *Miscanthus* species and/or variety such as, but not limited to, *Miscanthus* x *giganteus, Miscanthus sinensis, Miscanthus* x *ogiformis, Miscanthus floridulus, Miscanthus transmorrisonensis, Miscanthus oligostachyus, Miscanthus nepalensis, Miscanthus sacchariflorus, Miscanthus* x *giganteus* 'Amuri', *Miscanthus* x *giganteus* 'Nagara', *Miscanthus* x *giganteus* 'Illinois', *Miscanthus sinensis* var. 'Goliath', *Miscanthus sinensis* var. 'Roland', *Miscanthus sinensis* var. 'Africa', *Miscanthus sinensis* var. 'Fern Osten', *Miscanthus sinensis* var. *gracillimus, Miscanthus sinensis* var. *variegates, Miscanthus sinensis* var. *purpurascens, Miscanthus sinensis* var. 'Malepartus', *Miscanthus sacchariflorus* var. 'Robusta', *Miscanthus sinensis* var. 'Silberfedher' (aka. Silver Feather), *Miscanthus transmorrisonensis, Miscanthus condensatus, Miscanthus yakushimanum, Miscanthus* var. 'Alexander', *Miscanthus* var. 'Adagio', *Miscanthus* var. 'Autumn Light', *Miscanthus* var.

'Cabaret', *Miscanthus* var. 'Condensates', *Miscanthus* var. 'Cosmopolitan', *Miscanthus* var. 'Dixieland', *Miscanthus* var. 'Gilded Tower' (U.S. Patent No. PP14,743), *Miscanthus* var. 'Gold Bar' (U.S. Patent No. PP15,193), *Miscanthus* var. '*Gracillimus*', *Miscanthus* var. 'Graziella', *Miscanthus* var. 'Grosse Fontaine', *Miscanthus* var. 'Hinjo aka Little Nicky'™, *Miscanthus* var. 'Juli', *Miscanthus* var. 'Kaskade', *Miscanthus* var. 'Kirk Alexander', *Miscanthus* var. 'Kleine Fontaine', *Miscanthus* var. 'Kleine Silberspinne' (aka. 'Little Silver Spider'), *Miscanthus* var. 'Little Kitten', *Miscanthus* var. 'Little Zebra' (U.S. Patent No. PP13,008), *Miscanthus* var. 'Lottum', *Miscanthus* var. 'Malepartus', *Miscanthus* var. 'Morning Light', *Miscanthus* var. 'Mysterious Maiden' (U.S. Patent No. PP16,176), *Miscanthus* var. 'Nippon', *Miscanthus* var. 'November Sunset', *Miscanthus* var. 'Parachute', *Miscanthus* var. 'Positano', *Miscanthus* var. 'Puenktchen' (aka 'Little Dot'), *Miscanthus* var. 'Rigoletto', *Miscanthus* var. 'Sarabande', *Miscanthus* var. 'Silberpfeil' (aka. Silver Arrow), *Miscanthus* var. 'Silverstripe', *Miscanthus* var. 'Super Stripe' (U.S. Patent No. PP18,161), *Miscanthus* var. 'Strictus', or *Miscanthus* var. 'Zebrinus'.

In some embodiments, a suitable species can be a wild, weedy, or cultivated sorghum species and/or variety such as, but not limited to, *Sorghum almum, Sorghum amplum, Sorghum angustum, Sorghum arundinaceum, Sorghum bicolor* (such as *bicolor, guinea, caudatum, kafir,* and *durra*), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sorghum vulgare,* or hybrids such as *Sorghum* x *almum, Sorghum* x *sudangrass* or *Sorghum* x *drummondii.*

Thus, the methods and compositions can be used over a broad range of plant species, including species from the dicot genera *Brassica, Carthamus, Glycine, Gossypium, Helianthus, Jatropha, Parthenium, Populus,* and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum,* and *Zea*. In some embodiments, a plant is a member of the species *Panicum virgatum* (switchgrass), *Sorghum bicolor* (sorghum, sudangrass), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledonous plants and plant cell systems, wherein such plants are hybrids of different species or varieties of a specific species (e.g., *Saccharum* sp. X *Miscanthus* sp., Sorghum sp. X *Miscanthus* sp., e.g., *Panicum virgatum* x *Panicum amarum, Panicum virgatum* x *Panicum amarulum,* and *Pennisetum purpureum* x *Pennisetum typhoidum*).

D. Transgenic Plant Phenotypes

In some embodiments, a plant expressing an aluminum tolerance-modulating polypeptide can have increased levels of aluminum tolerance in plants. The aluminum tolerance level can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the aluminum tolerance level in a corresponding control plant that does not express the transgene. As described above, aluminum tolerance can be assessed by monitoring root growth or plant height in acidic soils containing elevated levels of $Al^{3+}$.

A plant in which expression of an aluminum tolerance-modulating polypeptide is modulated can have increased or decreased levels of seed production. The level can be increased or decreased by at least 2 percent, e.g., 2, 3, 4, 5, 10, 15, 20, 25, 30, 35, or more than 35 percent, as compared to the seed production level in a corresponding control plant that does not express the transgene. Increases in seed production can provide improved nutritional availability in geographic locales where intake of plant foods is often insufficient, or for biofuel production.

Typically, a difference in the amount of aluminum tolerance (e.g., as measured by root growth or plant height) in a transgenic plant relative to a control plant is considered statistically significant at $p<0.05$ with an appropriate parametric or non-parametric statistic, e.g., Chi-square test, Student's t-test, Mann-Whitney test, or F-test. In some embodiments, a difference in the amount of aluminum tolerance is statistically significant at $p<0.01$, $p<0.005$, or $p<0.001$. A statistically significant difference in, for example, the amount of aluminum tolerance in a transgenic plant compared to the amount of a control plant indicates that the recombinant nucleic acid present in the transgenic plant results in altered aluminum tolerance levels.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, 51 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

V. Modifying Endogenous Nucleic Acids Encoding Aluminum Tolerance-Modulating Polypeptides This document also features plant cells and plants in which an endogenous aluminum tolerance-modulating nucleic acid described herein has been modified (e.g., a regulatory region, intron, or coding region of the aluminum tolerance-modulating nucleic acid has been modified). The aluminum tolerance of such plants is altered relative to the corresponding level of a control plant in which the endogenous nucleic acid is not modified. Such plants are referred to herein as modified plants and may be used to produce, for example, increased amounts of aluminum tolerance.

Endogenous nucleic acid can be modified by homologous recombination techniques. For example, sequence specific endonucleases (e.g., zinc finger nucleases (ZFNs)) and meganucleases can be used to stimulate homologous recombination at endogenous plant genes. See, e.g., Townsend et al., *Nature* 459:442-445 (2009); Tovkach et al., *Plant J.,* 57:747-757 (2009); and Lloyd et al., *Proc. Natl. Acad. Sci. USA,* 102:2232-2237 (2005). In particular, ZFNs engineered to create DNA double strand breaks at specific loci can be used to make targeted sequence changes in endogenous plant genes. For example, an endogenous plant gene can be replaced with a variant containing one or more mutations (e.g., produced using site-directed mutagenesis or directed evolution). In some embodiments, site directed mutagenesis is achieved via non-homologous end joining such that after breaking DNA, endogenous DNA repair mechanisms ligate the break, often introducing slight deletions or additions that can be screened at the cell or plant level for desired phenotypes. Moore and Haber, *Mol Cell Biol.,* 16(5):2164-73 (1996).

In some embodiments, endogenous nucleic acids can be modified by methylation or demethylation such that the expression of the modified endogenous nucleic acid is altered. For example, a double stranded RNA can be used to activate gene expression by targeting noncoding regulatory regions in gene promoters. See Shibuya et al., *Proc Natl Acad Sci USA,* 106(5): 1660-1665 (2009); and Li et al., *Proc Natl Acad Sci USA,* 103(46):17337-42 (2006). In some embodiments, ZFNs engineered to create DNA double strand breaks at specific loci can be used to insert a DNA fragment having at least one region that overlaps with the endogenous DNA to facilitate homologous recombination, such that the non-overlapping portion of the DNA fragment is integrated at the break site. For example, a fragment can be inserted into an endogenous promoter and/or regulatory region at a specific site where a ZFN creates a double stranded break to alter the expression of an endogenous gene. For example, a fragment that is inserted into an endogenous gene coding region at a specific site where a ZFN creates a double stranded break can result in expression of a chimeric gene. For example, a fragment that functions as a regulator region or promoter that is inserted into an endogenous DNA region immediately upstream of a gene coding sequence at a specific site where a ZFN creates a double stranded break can result in altered expression of the endogenous gene.

In some embodiments, endogenous nucleic acids can be modified using activation tagging. For example, a vector containing multiple copies of an enhancer element from the constitutively active promoter of the cauliflower mosaic virus (CaMV) 35S gene can be used to activate an endogenous gene. See, Weigel et al., *Plant Physiology,* 122:1003-1013 (2000).

In some embodiments, endogenous nucleic acids can be modified by introducing an engineered transcription activation/repression factor (e.g., zinc finger protein transcription factor, or ZFP TF. See, for example, the world wide web at sangamo.com/tech/tech_plat_over.html#whatarezfp). For example, a synthetic transcription facto sequence of a zinc finger DNA binding domain and a VP16 activation domain can be designed to bind to a specific endogenous DNA site and alter expression of an endogenous gene. An engineered transcription activation/repression factor (such as ZFP TF) can activate, repress, or switch the target endogenous aluminum tolerance gene expression by binding specifically to the promoter region or coding region of the endogenous gene. Engineered nucleases that cleave specific DNA sequences in vivo can also be valuable reagents for targeted mutagenesis. One such class of sequence-specific nucleases can be created by fusing transcription activator-like effectors (TALEs) to the catalytic domain of the FokI endonuclease. Both native and custom TALE-nuclease fusions direct DNA double-strand breaks to specific, targeted sites. Christian et al., *Genetics* 186: 757-761 (2010).

In some embodiments, endogenous nucleic acids can be modified by mutagenesis. Genetic mutations can be introduced within regenerable plant tissue using one or more mutagenic agents. Suitable mutagenic agents include, for example, ethyl methane sulfonate (EMS), N-nitroso-N-ethylurea (ENU), methyl N-nitrosoguanidine (MNNG), ethidium bromide, diepoxybutane, ionizing radiation, x-rays, UV rays and other mutagens known in the art. Suitable types of mutations include, for example, insertions or deletions of nucleotides, and transitions or transversions in the endogenous nucleic acid sequence. In one embodiment, TILLING (Targeted Induced Local Lesions In Genomes) can be used to produce plants having a modified endogenous nucleic acid. TILLING combines high-density mutagenesis with high-throughput screening methods. See, for example, McCallum et al., *Nat Biotechnol* 18: 455-457 (2000); reviewed by Stemple, *Nat Rev Genet* 5(2):145-50 (2004).

In some embodiments, an endogenous nucleic acid can be modified via a gene silencing technique. See, for example, the section herein regarding "Inhibition of Expression of an aluminum tolerance-Modulating Polypeptide."

A population of plants can be screened and/or selected for those members of the population that have a modified nucleic acid. A population of plants also can be screened and/or selected for those members of the population that have a trait or phenotype conferred by expression of the modified nucleic acid. As an alternative, a population of plants can be screened for those plants having a desired trait, such as a modulated level of aluminum tolerance. For example, a population of progeny can be screened for those plants having a desired level of expression of an aluminum tolerance-modulating polypeptide or nucleic acid. Physical and biochemical methods can be used to identify modified nucleic acids and/or expression levels as described with transgenic plants. Selection and/or screening can be carried out over one or more generations, and/or in more than one geographic location. In some cases, plants can be grown and selected under conditions which induce a desired phenotype or are otherwise necessary to produce a desired phenotype in a modified plant. In addition, selection and/or screening can be applied during a particular developmental stage in which the phenotype is expected to be exhibited by the plant. Selection and/or screening can be carried out to choose those modified plants having a statistically significant difference in an aluminum tolerance level relative to a control plant in which the nucleic acid has not been modified. Selected or screened modified plants have an altered phenotype as compared to a corresponding control plant, as described in the "Transgenic Plant Phenotypes" section herein.

Although a plant or plant cell in which an endogenous aluminum tolerance-modulating nucleic acid has been modified is not transgenic for that particular nucleic acid, it will be appreciated that such a plant or cell may contain transgenes. For example, a modified plant can contain a transgene for other traits, such as herbicide tolerance or insect resistance. As another example, a modified plant can contain one or more transgenes that, in conjunction with modifications of one or more endogenous nucleic acids, exhibits an increase in aluminum tolerance.

As with transgenic plant cells, modified plant cells can constitute part or all of a whole plant. Such plants can be grown in the same manner as described for transgenic plants and can be bred or propagated in the same manner as described for transgenic plants.

VI. Plant Breeding

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. For example, PCR techniques can be used to enzymatically amplify a genetic marker associated with a nucleotide sequence conferring a specific trait (e.g., nucleotide sequences described herein). PCR can be used to amplify specific sequences from DNA as well as RNA, including sequences from total genomic DNA or total cellular RNA. When using RNA as a source of template, reverse transcriptase can be used to synthesize complementary DNA (cDNA) strands. Various PCR methods are described, for example, in *PCR Primer: A Laboratory Manual*, Dieffenbach and Dveksler, eds., Cold Spring Harbor Laboratory Press, 1995.

Generally, sequence information from polynucleotides flanking the region of interest or beyond is employed to design oligonucleotide primers that are identical or similar in sequence to opposite strands of the template to be amplified. Primers are typically 14 to 40 nucleotides in length, but can range from 10 nucleotides to hundreds of nucleotides in length. Template and amplified DNA is repeatedly denatured at a high temperature to separate the double strand, then cooled to allow annealing of primers and the extension of nucleotide sequences through the microsatellite, resulting in sufficient DNA for detection of PCR products. If the probes flank an SSR in the population, PCR products of different sizes will be produced. See, e.g., U.S. Pat. No. 5,766,847.

PCR products can be qualitative or quantitatively analyzed using several techniques. For example, PCR products can be stained with a fluorescent molecule (e.g., PicoGreen® or OliGreen®) and detected in solution using spectrophotometry or capillary electrophoresis. In some cases, PCR products can be separated in a gel matrix (e.g., agarose or polyacrylamide) by electrophoresis, and size-fractionated bands comprising PCR products can be visualized using nucleic acid stains. Suitable stains can fluoresce under UV light (e.g., Ethidium bromide, GR Safe, SYBR® Green, or SYBR® Gold). The results can be visualized via transillumination or epi-illumination, and an image of the fluorescent pattern can be acquired using a camera or scanner, for example. The image can be processed and analyzed using specialized software (e.g., ImageJ) to measure and compare the intensity of a band of interest against a standard loaded on the same gel.

Alternatively, SSR polymorphisms can be identified by using PCR product(s) as a probe against Southern blots from different individuals in the population. See, U. H. Refseth et al., (1997) *Electrophoresis* 18: 1519. Briefly, PCR products are separated by length through gel electrophoresis and transferred to a membrane. SSR-specific DNA probes, such as oligonucleotides labeled with radioactive, fluorescent, or chromogenic molecules, are applied to the membrane and hybridize to bound PCR products with a complementary nucleotide sequence. The pattern of hybridization can be visualized by autoradiography or by development of color on the membrane, for example.

In some cases, PCR products can be quantified using a real-time thermocycler detection system. For example, Quantitative real-time PCR can use a fluorescent dye that forms a DNA-dye-complex (e.g., SYBR® Green), or a fluorophore-containing DNA probe, such as single-stranded oligonucleotides covalently bound to a fluorescent reporter or fluorophore (e.g. 6-carboxyfluorescein or tetrachlorofluorescin) and quencher (e.g., tetramethylrhodamine or dihydrocyclopyrroloindole tripeptide minor groove binder). The fluorescent signal allows detection of the amplified product in real time, thereby indicating the presence of a sequence of interest, and allowing quantification of the copy number of a sequence of interest in cellular DNA or expression level of a sequence of interest from cellular mRNA.

The identification of RFLPs is discussed, for example, in Alonso-Blanco et al. (*Methods in Molecular Biology*, vol. 82, "*Arabidopsis* Protocols", pp. 137-146, J. M. Martinez-Zapater and J. Salinas, eds., c. 1998 by Humana Press, Totowa, N.J.); Burr ("Mapping Genes with Recombinant Inbreds", pp. 249-254, in Freeling, M. and V. Walbot (Ed.), *The Maize Handbook*, c. 1994 by Springer-Verlag New York, Inc.: New York, N.Y., USA; Berlin Germany; Burr et al. *Genetics* (1998) 118: 519; and Gardiner, J. et al., (1993) *Genetics* 134: 917). For example, to produce a RFLP library enriched with single- or low-copy expressed sequences, total DNA can be digested with a methylation-sensitive enzyme (e.g., PstI). The digested DNA can be separated by size on a preparative gel. Polynucleotide fragments (500 to 2000 bp) can be excised, eluted and cloned into a plasmid vector (e.g., pUC18). Southern blots of plasmid digests can be probed with total sheared DNA to select clones that hybridize to single- and low-copy sequences. Additional restriction endonucleases can be tested to increase the number of polymorphisms detected.

The identification of AFLPs is discussed, for example, in EP 0 534 858 and U.S. Pat. No. 5,878,215. In general, total cellular DNA is digested with one or more restriction enzymes. Restriction halfsite-specific adapters are ligated to all restriction fragments and the fragments are selectively amplified with two PCR primers that have corresponding adaptor and restriction site specific sequences. The PCR products can be visualized after size-fractionation, as described above.

In some embodiments, the methods are directed to breeding a plant line. Such methods use genetic polymorphisms identified as described above in a marker assisted breeding program to facilitate the development of lines that have a desired alteration in the aluminum tolerance trait. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VII. Articles of Manufacture

Transgenic plants provided herein have various uses in the agricultural and energy production industries. For example, transgenic plants described herein can be used to make animal feed and food products. Such plants, however, are often particularly useful as a feedstock for energy production.

Transgenic plants described herein produce higher yields of grain and/or biomass per hectare, relative to control plants that lack the exogenous nucleic acid or lack the modified endogenous nucleic acid when grown on soils with a pH less than 5 and elevated aluminum levels. For example, transgenic plants described herein can have a grain yield that is increased about 5% to about 20% (e.g., increased 5% to 10%, 5% to 15%, 10% to 15%, 10% to 20%, or 15% to 20%) relative to that of control plants lacking the exogenous nucleic acid or lacking the modified endogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as low pH and elevated aluminum levels.

In some embodiments, plants described herein have a composition that permits more efficient processing into free sugars, and subsequently ethanol, for energy production. In some embodiments, such plants provide higher yields of ethanol, butanol, dimethyl ether, other biofuel molecules, and/or sugar-derived co-products per kilogram of plant material, relative to control plants. Such processing efficiencies are believed to be derived from the composition of the plant material, including, but not limited to, content of glucan, cellulose, hemicellulose, and lignin By providing higher yields at an equivalent or even decreased cost of production, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

The invention will be further described in the following examples, which do not limit the scope of the invention described in the claims.

VIII. Examples

Example 1—Materials and Methods

Plant agar culture media lacking phosphate were prepared in 2 L Pyrex glass bottles and contained the following per 1 L: 0.78 g/L of ½×MS without $KH_2PO_4$ (Sigma Chemical Co., St. Louis, Mo.), 0.5 g/L MES (Sigma Chemical Co.) and 7 g/L of 0.7% Phytagar (EM Science, Gibbstown, N.J.). Media were stirred for 30 minutes after the addition of ½ MS. The pH after the MS was completely dissolved was close to pH 5.7, and adjusted using KOH. The final pH of each batch was measured due to pH variability between batches. Media preparations were autoclaved at about 121° C. for 25 minutes on a liquid setting. Approximately 40 mL of media were added to each square plate (100×100×15 mm) in a laminar flow hood using a liquid dispensing device or 50 mL sterile pipette. The plates were immediately covered with lids to avoid contamination. Plates were allowed to cool in a laminar flow hood for at least 1 hour, but not more than 3 hours, with a blower on. Plates were stored in 4° C. in bags.

Liquid media lacking phosphate for use in $Al^{+3}$ assays were prepared in 2 L Pyrex glass bottles and contained per 1 L: 0.78 g/L of MS salt without $KH_2PO_4$ (Sigma Chemical Co.), 0.5 g/L MES (Sigma Chemical Co.), and 6 mL of 0.1M $AlCl_3$ (Sigma Chemical Co.) (600 µM $AlCl_3$ and predicted $Al^{+3}$ activity of 160 µM). Media were stirred for 30 minutes while the pH was adjusted slowly to pH 4.0 using 1N HCL. $AlCl_3$ was added after autoclaving. The preparations were autoclaved at about 121° C. for 25 minutes on a liquid setting.

Agar buffer media lacking phosphate, for use in $Al^{+3}$ assays, were prepared in 2 L Pyrex glass bottles and contained per 1 L: 0.78 g/L of MS salt without $KH_2PO_4$ (Sigma Chemical Co.), 0.5 g/L MES (Sigma Chemical Co.), and 4 g/L Phytagar (EM Science), with 1N HCL used to adjust to a pH of 4.8. The media were stirred for 30 minutes after the addition Phytagar and 1 N HCL. The final pH of each batch was recorded due to pH variability between batches. The media preparations were autoclaved at about 121° C. for 25 minutes on liquid setting. Approximately 20 mL of warm agar containing $Al^{+3}$ media were aliquoted to each of 10 horizontal wells within each hydroponic box (10 horizontal wells per box/10 seeds per horizontal well) using a 50 mL sterile pipette and allowed to solidify for about 2 hours before layering 10 mL of cooled liquid $Al^{+3}$ media on top over the agar media described above. A thin layer of the liquid media floated on and was suspended over the agar solidified media lacking phosphate and containing $Al^{+3}$. The hydroponic boxes were immediately covered with lids to avoid contamination and evaporation of the liquid layer before $Al^{+3}$ infiltrations into the solid agar layer. The hydroponic boxes were allowed to rest in the laminar flow hood for at least 1 hour, but not more than 3 hours, with a blower on (to avoid evaporation of the liquid layer during infiltration). The hydroponic boxes were stored in 4° C.

To sterilize seeds, the appropriate number of seeds from each candidate plant or ME line event were transferred to individual 2 mL tubes and 1 mL 30% Clorox bleach was added to each tube and agitated manually for at least 5 minutes until all seeds become suspended. Bleach solution then was discarded and seeds were rinsed aseptically with sterile nanopure water at least 4 times or until the seeds were thoroughly rinsed.

Example 2 $Al^{+3}$ Assay for Transgenic Arabidopsis thaliana

Forty-eight $T_3$ generation seeds of each of transgenic ME02064 events −01, −04, −03, plus an empty vector control (SR00559), were sterilized and plated on agar media lacking phosphate hydroponically suspended over $Al^{+3}$ liquid media (see Example 1). In each mini-hydroponic box, 48 control seeds plus 48 ME02064 seeds were sown. Boxes were kept in a 4° C. refrigerator in the dark for 3 days to promote uniform germination. After 3 days of cold treatment, the boxes were placed horizontally in a Conviron growth chamber as described above. The plates were scanned using a fluorescence imager scanner (Technologica Ltd, Colchester, UK) at 7 days and 14 days after sowing seeds. Plants were scored for growth when $Al^{+3}$ toxicity (e.g., stunted root growth and reduced rosette area) became apparent, usually around 10 days.

The seedling area and fluorescence intensity (Fv/Fm) were quantified in a pooled manner. Fv/Fm measurements as well as rosette area growth for each individual plant were not taken. Rather, the −01, −04, & −03 seedling populations (48 seedlings) were compared to the pooled control (48 seedlings) within the same mini-hydroponic box. Total rosette growth was measured for 48 seedlings from transgenic lines and for 48 seedlings from control lines. Stress that resulted in decreases in the quantum efficiency of photochemistry (open PSII reaction centers), determined by Fv/Fm of dark adapted plants, was considered an indicator of inhibition of photosynthesis by $Al^{+3}$. Basta resistance was not tested as other assays had indicated that these lines were transgenic.

Rosette area was larger at 10 days in all transgenic events of −01, −04, & −03 when compared to empty vector controls (SR00559) as shown in Table 1. However, no visual difference in root growth was observed (data not shown). Roots for both transgenics and controls were all severely stunted, failing to penetrate from the agar media support into the high $Al^{+3}$ liquid media. The mean Fv/Fm appeared to be moderately higher in transgenic events −01, −04, & −03 relative to controls, but there was no statistically significant difference.

TABLE 1

| 60 µM $AlCl_3$ 10 days | | SR00559 |
|---|---|---|
| ME02064-01T3 | | |
| Sum of Rosette Areas ($mm^2$) | 587.74 | 478.23 |
| Mean Fv/Fm | 0.722 | 0.713 |
| ME02064-04T3 | | |
| Sum of Rosette Areas ($mm^2$) | 676.19 | 619.3 |
| Mean Fv/Fm | 0.775 | 0.763 |
| ME02064-03T3 | | |
| Sum of Rosette Areas ($mm^2$) | 578.23 | 436.96 |
| Mean Fv/Fm | 0.712 | 0.717 |

Example 3 $Al^{+3}$ Assay for Transgenic Switchgrass Plants

A T-DNA binary vector containing Ceres Clone 375578 (SEQ ID NO:352) was introduced into switchgrass by Agrobacterium-mediated transformation essentially as described in Richards et al., Plant Cell. Rep. 20:48-54 (2001) and Somleva, et al., Crop Sci. 42:2080-2087 (2002). The presence of the transgene was confirmed by PCR. Plants comprising the transgene were grown in acidified soil containing high levels of $Al^{+3}$. The soil was made by dissolving $AlCl_3$ in water and watering the soil with the aluminized water. The soil then was acidified using pH 4 buffered water, to release the toxic aluminum ion. Because the acidity of the soil determines how much of the $Al^{+3}$ is present as the toxic free ion, the $Al^{+3}$ value was variable. Switchgrass control non-transgenic plants (Wt) and transgenic (CeresClone 375578) plants were placed in soil in separate pots in a growth room and allowed to grow under standard growth room conditions. Non-transgenic plants were generated from calli without co-cultivation with agrobacteria. There was one plant per pot. The plantlets were watered with one of the following three treatments: Treatment 1: 2 L of water, pH 7.26; Treatment 2: 2 L of water, pH 4.0; and Treatment 3: 2 L of water, pH 4.0+~11 g/Kg soil $Al^{+3}$ (~621 µM). The size of the transgenics and controls appeared similar when the treatment was started but no measurements were taken. After 16 days, seedlings were harvested, washed, and then dried in a drying oven. The dry weight biomass was measured for each plant.

Figure 5:
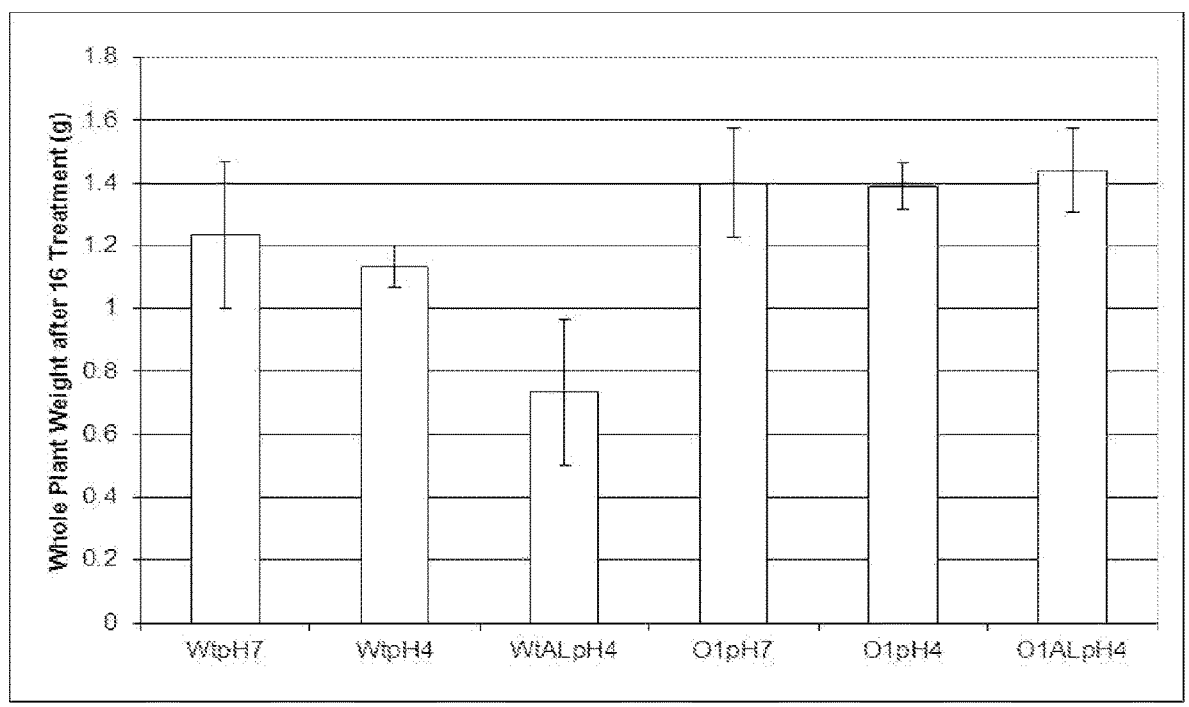
FIG. 5 is a bar graph of whole plant weight (shoots plus roots) of either wild-type (WT) controls or transgenic switchgrass (Ceres Clone 375578) treated with either pH 7.26 water (pH7); pH 4.0 water (pH4); or pH 4.0 water with aluminum (~11 g $AlCl_3$/Kg soil; ~0.00621 µM $Al^{3+}$) (AlpH4). Aluminum toxicity had little to no effect on plant weight of the transgenic plants in comparison to control.

Transgenic aerial plant growth was greater in the transgenic switchgrass events than in the controls as indicated by an increase in whole plant weight (shoots and roots). The increase was statistically significant at a P value of 0.05 when compared to wild-type plants (see FIG. 5, Tables 2 and 3). Root growth in the transgenic lines was visually more robust than wild-type controls. These results indicate that switchgrass containing Ceres Clone 375578 can survive in acidified soil having an aluminum chloride concentration of about 11 g/kg soil.

TABLE 2

Whole Plant Weight (Shoots + Roots)

| | Treatment 1 | | Treatment 2 | | Treatment 3 | |
|---|---|---|---|---|---|---|
| | Wt | 375578 | Wt | 375578 | Wt | 375578 |
| Mean Weight (g) | 1.23 | 1.4 | 1.33 | 1.39 | 0.73 | 1.44 |
| Standard Error | 0.23 | 0.17 | 0.07 | 0.07 | 0.23 | 0.13 |
| Median | 1 | 1.3 | 1.2 | 1.3 | 0.8 | 1.25 |
| Standard Deviation | 0.40 | 0.55 | 0.12 | 0.23 | 0.40 | 0.42 |
| Sample Variance | 0.16 | 0.3 | 0.01 | 0.05 | 0.16 | 0.18 |
| Skewness | 1.73 | 0.30 | −1.73 | 0.35 | 0.72 | 1.04 |
| Range | 0.7 | 1.4 | 0.2 | 0.6 | 0.8 | 1.3 |
| Minimum | 1 | 0.8 | 1 | 1.1 | 0.3 | 1 |
| Maximum | 1.7 | 2.2 | 1.2 | 1.7 | 1.1 | 2.3 |
| Sum | 3.7 | 14 | 3.4 | 13.9 | 2.2 | 14.4 |
| Count | 3 | 10 | 3 | 10 | 3 | 10 |

TABLE 3 t-Test: Two-Sample Assuming Unequal Variances of Plants under Treatment 3

| | Wild type Control, pH 4 | 375578 |
|---|---|---|
| Mean Whole Plant Weight (Shoots + Roots) (g) | 0.73 | 1.44 |
| Variance | 0.16 | 0.18 |
| Observations | 3 | 10 |
| Hypothesized Mean Difference | 0 | |
| Df | 3 | |
| t Stat | −2.63 | |
| P (T <= t) one-tail | 0.04 | |

TABLE 3-continued t-Test: Two-Sample Assuming Unequal Variances of Plants under Treatment 3

|  | Wild type Control, pH 4 | 375578 |
|---|---|---|
| t Critical one-tail |  | 2.35 |
| P (T <= t) two-tail |  | 0.08 |
| t Critical two-tail |  | 3.18 |

The results also indicate that wild type plants watered with Treatment 3 (pH 4 but without $AlCl_3$) had a whole plant weight that was less than the whole plant dry weight of wild type plants watered with Treatment 3. The results also indicate that the decrease in whole plant dry weight seen under Treatment 3 conditions was a result of $Al^{+3}$ toxicity, because wild-type plants grown under Treatment 2 conditions (pH 4 but without $AlCl_3$) showed no such decrease in whole plant dry weight (see Table 3).

Example 4—Germination of Rice Seedlings in Media Containing Aluminum

In this example, the role of CeresClone 24255 (Os713, 3 events), CeresClone 1752915 (Os825, 3 events), and CeresClone 11684 (Os879, 3 events) was assessed in rice seeds germinated in the presence of aluminum. Seeds of wild-type internal control (null segregant) and homozygous transgenic plants were placed on two separate plates for each event. Each plate had two rows of 12 seeds aligned in parallel. External wild-type seed were sown at the same time under control (no aluminum chloride) conditions using the same format for comparison of rate of germination and growth to that of $Al^{+3}$ conditions.

Unsterilized, de-husked seeds were germinated under normal or aluminum-stress conditions as follows. Normal conditions included a plate (150 mm×100 mm×15 mm) containing 30 mL of ½ MS medium without phosphate and nitrogen, no sugar, 4 g agar/L pH 5.7. Aluminum-stress conditions included a plate (150 mm×100 mm×15 mm) containing 20 mL of ½ MS medium without phosphate and nitrogen, no sugar, 4 g agar/L pH 5.7, infiltrated with 10 mL $AlCl_3$ liquid infiltration medium containing 600 μM $AlCl_3$ (which corresponds to a predicted ion activity of 160 μM on plates) in ½ MS pH 4. The $AlCl_3$ liquid infiltration medium was added on top of the aluminum medium and allowed to settle for 24 hours before seed placement on the surface. $AlCl_3$ liquid infiltration medium consisted of: ½ MS media without phosphate or nitrogen; no sugar or agar; and 600 μM $AlCl_3$, with the pH adjusted to 4.0 with 1N HCl. Predicted $Al^{+3}$ activities were confirmed with GEOCHEM-EZ, a multi-purpose chemical speciation program. See, Shaff et al., *Plant Soil* 330: 207-214 (2010).

Plates with lids were not sealed but were placed inside large ziplock bags to maintain humidity in growth chamber (25° C., 70% humidity for 8 hours light/16 hours dark). At 13 days, seedlings were measured for plant height and root length. See Tables 4 and 5. For Os713, plant height and root length were not significantly different between the transgenic plants and non-transgenic controls. For Os825 event 9, a significant increase in plant height was observed in comparison to the pooled non-transgenic control. For Os879 event 7, a significant increase in plant height was observed in comparison to the internal non-transgenic control. For Os879 event 4, a significant increase in plant height was observed in comparison to the internal non-transgenic control as well as a significant increase in root length in comparison to the pooled non-transgenic control. For Os870 event 8, a significant increase in root length was observed in comparison to the internal and pooled non-transgenic controls.

TABLE 4

Plant Height after 13 d Aluminum Treatment

| Genotype | Copy number of transgene | # of plants tested | Transgenics | | | Non-transgenics | | | P-value | |
|---|---|---|---|---|---|---|---|---|---|---|
|  |  |  | Average | Standard Deviation | #r of plants | Average | Standard Deviation | # of plants | Internal NT | Pooled NT |
| OS713-07 | 1 | 24 | 5.11 | 5.01 | 12 | 6.73 | 4.27 | 12 | 0.41 | 0.74 |
| OS713-05 | 1 | 24 | 2.92 | 4.47 | 12 | 1.91 | 2.62 | 12 | 0.50 | 0.22 |
| OS713-03 | 1 | 24 | 6.42 | 5.63 | 12 | 5.21 | 3.43 | 12 | 0.53 | 0.23 |
| All OS713 |  |  | 4.81 | 5.13 | 36 | 4.62 | 3.97 | 36 | 0.86 |  |
| OS825-13 | 1 | 24 | 3.89 | 5.15 | 12 | 2.09 | 2.55 | 12 | 0.28 | 0.61 |
| OS825-10 | 1 | 24 | 3.95 | 4.26 | 12 | 3.15 | 4.43 | 12 | 0.66 | 0.56 |
| OS825-09 | 1 | 24 | 5.95 | 4.95 | 12 | 4.28 | 4.36 | 12 | 0.39 | 0.05 |
| All OS825 |  |  | 4.60 | 4.76 | 36 | 3.17 | 3.88 | 36 | 0.23 |  |
| OS879-08 | 1 | 24 | 5.23 | 4.34 | 12 | 2.88 | 3.96 | 12 | 0.18 | 0.10 |
| OS879-07 | 1 | 24 | 4.88 | 4.50 | 12 | 1.28 | 2.81 | 12 | 0.03 | 0.18 |
| OS879-04 | 1 | 24 | 5.72 | 4.63 | 12 | 5.03 | 3.73 | 12 | 0.69 | 0.05 |
| All OS879 |  |  | 5.27 | 4.38 | 36 | 3.07 | 3.77 | 36 | 0.02 |  |

TABLE 5

Root Length after 13 d Aluminum Treatment

| Genotype | Number of plants tested | Transgenics | | | Non-transgenics | | | P-value | |
|---|---|---|---|---|---|---|---|---|---|
| | | Average | Standard Deviation | Number of plants | Average | Standard Deviation | Number of plants | Internal NT | Pooled NT |
| OS713-07 | 24 | 0.79 | 0.83 | 12 | 1.5 | 0.87 | 12 | 0.059 | 0.97 |
| OS713-05 | 24 | 0.75 | 1.08 | 12 | 0.2 | 0.36 | 12 | 0.11 | 0.87 |
| OS713-03 | 24 | 1.2 | 1.08 | 12 | 0.7 | 0.50 | 12 | 0.16 | 0.18 |
| | | 0.92 | 1.00 | 36 | 0.8 | 0.81 | 36 | 0.59 | |
| OS825-13 | 24 | 0.38 | 0.64 | 12 | 0.28 | 0.47 | 12 | 0.67 | 0.42 |
| OS825-10 | 24 | 0.38 | 0.87 | 12 | 0.73 | 1.12 | 12 | 0.41 | 0.46 |
| OS825-09 | 24 | 0.58 | 0.51 | 12 | 0.79 | 0.84 | 12 | 0.47 | 0.96 |
| | | 0.45 | 0.68 | 36 | 0.60 | 0.86 | 36 | 0.35 | |
| OS879-08 | 24 | 0.85 | 0.72 | 12 | 0.29 | 0.45 | 12 | 0.03 | 0.005 |
| OS879-07 | 24 | 0.53 | 0.59 | 12 | 0.16 | 0.37 | 12 | 0.08 | 0.23 |
| OS879-04 | 24 | 0.94 | 0.78 | 12 | 0.57 | 0.42 | 12 | 0.16 | 0.002 |
| | | 0.78 | 0.71 | 36 | 0.34 | 0.44 | 36 | 0.002 | |

Example 5—Seedling Growth of Transgenic Rice Containing CeresClone 375578, CeresClone 24255, and CeresClone 11684 in Rice The experiments described in Example 4 were repeated using transgenic rice events for CeresClone 375578 (Line 745282, one of 7 events), CeresClone 24255 (Os713, 3 events), and CeresClone 11684 (Os879, 3 events). After germination under normal or aluminum conditions as described in Example 4, and incubation for 10 or 11 days in the growth chamber, surviving seedlings were transplanted to soil (60% Sunshine Professional Mix (with vermiculite); 40% Turface; 1 tbs/3 L Osmocote; 1.5 tbs/3 L of Bone Meal; and 0.5 tbs/3 L Marathon).

Plants were genotyped as follows. Plants were allowed to recover until the two leaf stage then genotyped by cutting 5 to 6 mm leaf segments from the largest of the two leaves and placed onto Kanamycin medium plates containing 160 mg/L of Kanamycin (¼ MS basal salt medium; 4.5 g/L of Phytoagar; 100 µL/L of Tween 80; and adjusted to pH 5.7 with 1N KOH. Medium was sterilized under the wet cycle for 30 minutes at 120° C. and allowed to cool before adding Kanamcyin to a final concentration of 160 mg/L). Plates were sealed in Ziplock bags and placed in a growth chamber at about 26±2° C. under normal growing light regime (16 h light and 8 h dark).

Plates were removed from the chamber during a light period and scanned starting at 4 d of treatment. If unclear, the plates were re-scanned at 5 or 6 days post treatment. Plates were scanned for photosynthetic efficiency (PE) quantification to determine genotype. Generally, PE is a parameter (Fv/Fm, the ratio of variable florescence over the maximum florescence value) used to indicate the quantum efficiency of the photosystem type II (PSII) reactions within the plants chloroplasts. The Fv/Fm parameter is an indication of photosynthetic tissue health. Healthy tissue samples typically achieve an Fv/Fm value of approximately 0.7-0.85. Lower values are observed if a sample is exposed to a biotic or abiotic stress factor that reduce the capacity for photochemical quenching of energy within PSII.

Images of chlorophyll fluorescence and the florescence parameters were obtained with Chlorophyll Fluorescence imager (Technologica, UK) using the manufacturer's instructions for light-adapted materials. Representative regions of the image, e.g., distant from the any cut end to avoid damage effects, were chosen for reading the Fv/Fm values. PCR analysis was used to confirm the presence of transgenes.

After genotyping, plants were grown in soil and treated with either water (Normal) or with acidified water (~pH 4.0) containing 600 µM $AlCl_3$. After 19 days, root length and plant height were measured. Root and plant height data for transgenic plants were statistically compared to non-transgenic (NT) internal segregant lines, pooled NT internal segregant lines, external NT lines, and all NT lines. Comparisons were also made to plants not treated with AL containing water.

Tables 6 and 7 contain the results of line 745282 (7 events) for root expansion at 19 days and plant height at 19 days, respectively. For line 745282, a significant increase in root expansion was observed for events 745282, 745284, 745252, and 745307; a significant increase in plant height was observed for events 745284 and 745236.

Tables 8 and 9 contain the results for Os713 and Os879 for root expansion at 19 days and plant height at 19 days, respectively. For Os879, a significant increase in plant height was observed for event 7.

TABLE 6

Root expansion (cm) under Aluminum treatment 19 d

| Genotype | Transgenics | | | Non-transgenics | | | P-value | | | |
|---|---|---|---|---|---|---|---|---|---|---|
| | | | | | | | Line | Pooled | | |
| | Average | Standard Deviation | Number of plants | Average | Standard Deviation | Number of plants | Internals NT | Internals NT | External NT | Internal + External |
| 745282 | 4.55 | 2.9 | 11 | 4.2 | 2.68 | 5 | 0.78 | 0.41 | 0.006 | 0.10 |
| 745284 | 6.38 | 2.05 | 8 | 4.06 | 1.82 | 8 | 0.03 | 0.01 | 3.83E−05 | 0.001 |
| 745236 | 2.23 | 3.14 | 13 | 4.17 | 3.82 | 3 | 0.39 | 0.09 | 0.90 | 0.226 |

TABLE 6-continued

Root expansion (cm) under Aluminum treatment 19 d

| | Transgenics | | | Non-transgenics | | | P-value Line | Pooled | | |
|---|---|---|---|---|---|---|---|---|---|---|
| Genotype | Average | Standard Deviation | Number of plants | Average | Standard Deviation | Number of plants | Internals NT | Internals NT | External NT | Internal + External |
| 745252 | 5 | 2.96 | 7 | 3.06 | 3.26 | 9 | 0.24 | 0.30 | 0.011 | 0.083 |
| 745306 | 5.6 | 3.44 | 5 | 6.29 | 2.1 | 11 | 0.62 | 0.18 | 0.008 | 0.050 |
| 745312 | 7.02 | 2.16 | 16 | n/a | n/a | n/a | n/a | 9.93E−05 | 3.58E−08 | 4.25E−07 |
| 745307 | 5.19 | 2.9 | 8 | 4.13 | 2.4 | 8 | 0.44 | 0.20 | 0.005 | 0.043 |
| All transgenics | 5.1 | 3.03 | 68 | 5.1 | 9.06 | | | 0.042 | 0.0001 | 0.001 |
| Pooled NT | | | | 3.833 | 2.59 | 33 | | | | |
| External WT | | | | 2.347 | 2.01 | 23 | | | | |
| Internal + External | | | | 3.22 | 2.46 | 56 | | | | |

TABLE 7

Plant height (cm) under Aluminum treatment 19 d

| | | | Transgenics | | | Non-transgenics | | | P-value Line | | | |
|---|---|---|---|---|---|---|---|---|---|---|---|---|
| Genotype | Copy number of transgene | Number of plants tested | Average | Standard Deviation | Number of plants | Average | Standard Deviation | Number of plants | Internals NT | Pooled Internals NT | External NT | Internal + External NT |
| 745282 | 1 | 16 | 21.45 | 2.9 | 11 | 24.3 | 7.98 | 5 | 0.32 | 0.38 | 0.0002 | 0.293 |
| 745284 | 1 | 16 | 25.63 | 4.24 | 8 | 21.25 | 3.01 | 8 | 0.032 | 0.08 | 3.66E−06 | 0.005 |
| 745236 | 2 | 16 | 23.23 | 2.01 | 13 | 22.67 | 3.06 | 3 | 0.693 | 0.64 | 7.56E−07 | 0.026 |
| 745252 | 1 | 16 | 23.86 | 7.78 | 7 | 21.83 | 3.76 | 9 | 0.502 | 0.56 | 0.0009 | 0.076 |
| 745306 | 1 | 16 | 23.96 | 3.33 | 5 | 25 | 5.56 | 11 | 0.707 | 0.51 | 0.0004 | 0.0958 |
| 745312 | 2 | 16 | 23.98 | 1.92 | 16 | n/a | n/a | n/a | n/a | 0.23 | 1.14E−08 | 0.003 |
| 745307 | 1 | 16 | 21.44 | 2.29 | 8 | 23.94 | 2.88 | 8 | 0.075 | 0.43 | 8.77E−04 | 0.367 |
| All transgenics | 1 & 2 | 112 | 23.31 | 9.42 | 68 | | | | | 0.42 | 8.38E−11 | 0.0003 |
| Pooled NT | 0 | 33 | | | | 22.67 | 9.53 | 33 | | | | |
| External WT | 0 | 23 | | | | 15.2 | 9.54 | 23 | | | | |
| Internal + External | 0 | 56 | | | | 19.59 | 4.99 | 56 | | | | |

TABLE 8

Root Length after 19 d aluminum treatment

| | Transgenics | | | Non-transgenics | | | P-value | | | |
|---|---|---|---|---|---|---|---|---|---|---|
| Genotype | Average | Standard Deviation | Number of plants | Average | Standard Deviation | Number of plants | Internal NT | Pooled NT | External WT | Internal + External |
| W2 (939-006) | 6.1 | 1.55 | 7 | 4.4 | 1.35 | 3 | 0.14 | | 0.49 | 0.22 |
| 713-3 | 5.32 | 0.53 | 6 | 6.13 | 1.31 | 4 | 0.21 | 0.95 | 0.55 | 0.75 |
| 713-5 | 4.63 | 1.60 | 8 | 4 | 0 | 2 | 0.61 | 0.36 | 0.19 | 0.16 |
| 713-7 | 4.19 | 1.93 | 8 | 5 | | 1 | 0.70 | 0.21 | 0.11 | 0.06 |
| 879-4 | 4.33 | 1.22 | 9 | 7 | | 1 | 0.07 | 0.33 | 0.04 | 0.06 |
| 879-7 | 5.56 | 1.81 | 9 | 4 | | 1 | 0.44 | 0.63 | 0.95 | 0.80 |
| 879-8 | 4.29 | 0.70 | 7 | 4.8 | 1.31 | 3 | 0.43 | 0.23 | 0.02 | 0.04 |
| All T713 | 4.65 | 1.54 | 22 | | | | | | | |
| All T879 | 4.76 | 1.44 | 25 | | | | | | | |
| Pooled NT 713_879 | | | | 5.24 | 1.35 | 12 | | | | |
| Pooled NT_713 | | | | 5.36 | 1.38 | 7 | | | | |
| Pooled NT_879 | | | | 5.08 | 1.46 | 5 | | | | |
| External NT WT | | | | 5.6 | 1.02 | 7 | | | | |
| All NT SAP + Externals | | | | 5.37 | 1.22 | 19 | | | | |
| External + NT713 | | | | 5.48 | 1.19 | 14 | | | | |
| External + NT879 | | | | 5.38 | 1.19 | 12 | | | | |

TABLE 8-continued

Root Length after 19 d aluminum treatment

| Genotype | Transgenics | | | Non-transgenics | | | P-value | | | |
|---|---|---|---|---|---|---|---|---|---|---|
| | Average | Standard Deviation | Number of plants | Average | Standard Deviation | Number of plants | Internal NT | Pooled NT | External WT | Internal + External |
| All T713_Untreated | 7.93 | 2.09 | 7 | | | | | | | |
| All T879_Untreated | 7.7 | 1.86 | 8 | | | | | | | |
| All T W2_Untreated | 5.44 | 1.40 | 8 | | | | | | | |
| T713_879_Untreated | 7.09 | 1.46 | 11 | | | | | | | |
| NT713_879_Untreated | | | | 7 | 1.91 | 7 | | | | |

TABLE 9

Plant height after 19 d aluminum treatment

| Genotype | Copy number of transgene | Number of plants tested | Transgenics | | | Non-transgenics | | | P-value | | | |
|---|---|---|---|---|---|---|---|---|---|---|---|---|
| | | | Average | Standard Deviation | Number of plants | Average | Standard Deviation | Number of plants | Internal NT | Pooled NT | External WT | Internal + External |
| W2 (939-006) | 1 | 10 | 16.17 | 0.99 | 7 | 15.33 | 2.04 | 3 | 0.39 | | 0.20 | 0.24 |
| 713-3 | 1 | 10 | 18.3 | 1.01 | 6 | 17.4 | 1.37 | 4 | 0.26 | 0.00 | 0.06 | 0.13 |
| 713-5 | 1 | 10 | 16.76 | 1.60 | 8 | 17.15 | 0.92 | 2 | 0.76 | 0.55 | 0.11 | 0.35 |
| 713-7 | 1 | 10 | 15.06 | 6.78 | 8 | 16.5 | 0.135 | 2 | 0.85 | 0.43 | 0.54 | 0.99 |
| 879-4 | 1 | 10 | 14.78 | 2.89 | 9 | 17.9 | | 1 | 0.34 | 0.07 | 0.45 | 0.93 |
| 879-7 | 1 | 10 | 17.94 | 2.06 | 9 | 16 | | 1 | 0.40 | 0.85 | 0.04 | 0.13 |
| 879-8 | 1 | 10 | 18.09 | 1.71 | 7 | 18.23 | 2.87 | 3 | 0.92 | 0.75 | 0.06 | 0.15 |
| All T713 | 1 | | 16.56 | 4.26 | 22 | | | | | | | |
| All T879 | 1 | | 16.844 | 2.73 | 25 | | | | | | | |
| Pooled NT 713_879 | 0 | | | | | 17.42 | 1.60 | 12 | | | | |
| Pooled NT_ 713 | 0 | | | | | 17.2 | 1.09 | 7 | | | | |
| Pooled NT_879 | 0 | | | | | 17.72 | 2.25 | 5 | | | | |
| External NT WT | 0 | | | | | 12.96 | 6.19 | 7 | | | | |
| All NT SAP + Externals | | | | | | 15.77 | 4.38 | 19 | | | | |
| External + NT713 | | | | | | 15.08 | 4.80 | 14 | | | | |
| External + NT879 | | | | | | 14.94 | 5.36 | 12 | | | | |
| All T713_Untreated | | | 18.68 | 1.11 | 7 | | | | | | | |
| All T879_Untreated | | | 16.63 | 1.41 | 8 | | | | | | | |
| All T W2_Untreated | | | 17.89 | 1.61 | 8 | | | | | | | |
| T713_879_Untreated | | | 17.58 | 1.63 | 15 | | | | | | | |
| NT713_879_Untreated | | | 18.41 | 2.86 | 7 | | | | | | | |

Example 6—Determination of Functional Homologs by Reciprocal BLAST®

A candidate sequence was considered a functional homolog of a reference sequence if the candidate and reference sequences encoded proteins having a similar function and/or activity. A process known as Reciprocal BLAST® (Rivera et al., Proc. Natl. Acad. Sci. USA, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST® process, a specific reference polypeptide was searched against all peptides from its source species using BLAST® in order to identify polypeptides having BLAST® sequence identity of 80% or greater to the reference polypeptide and an alignment length of 85% or greater along the shorter sequence in the alignment. The reference polypeptide and any of the aforementioned identified polypeptides were designated as a cluster.

The BLASTP® version 2.0 program from Washington University at Saint Louis, Mo., USA was used to determine BLAST® sequence identity and E-value. The BLASTP® version 2.0 program includes the following parameters: 1) an E-value cutoff of 1.0e-5; 2) a word size of 5; and 3) the -postsw option. The BLAST® sequence identity was calculated based on the alignment of the first BLAST® HSP (High-scoring Segment Pairs) of the identified potential functional homolog sequence with a specific reference polypeptide. The number of identically matched residues in the BLAST® HSP alignment was divided by the HSP length, and then multiplied by 100 to get the BLAST® sequence identity. The HSP length typically included gaps in the alignment, but in some cases gaps were excluded.

The main Reciprocal BLAST® process consists of two rounds of BLAST® searches; forward search and reverse search. In the forward search step, a reference polypeptide sequence, "polypeptide A," from source species SA was BLASTed® against all protein sequences from a species of interest. Top hits were determined using an E-value cutoff of 10-5 and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed® against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NOs: 353, 237, 451, and 2 are shown in FIGS. 1-4, respectively. Additional exemplary homologs are correlated to certain Figures in the Sequence Listing.

Example 7—Determination of Functional Homologs by Hidden Markov Models

Hidden Markov Models (HMMs) were generated by the program HMMER 2.3.2. To generate each HMM, the default HMMER 2.3.2 program parameters, configured for global alignments, were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ ID NO: 353.

The procedure above was repeated and an HMM was generated for each group of sequences shown in FIGS. 2-4, using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11254948B2). An electronic copy of the "Sequence Listing" will also be available from the USPTO upon request and payment of the fee set forth in 37 CFR 1.19(b)(3).

What is claimed is:

1. A transgenic plant comprising an exogenous nucleic acid, said exogenous nucleic acid comprising a regulatory region operably linked to a nucleotide sequence,
   wherein the nucleotide sequence comprises a polynucleotide sequence having 95 percent or greater sequence identity to the nucleotide sequence set forth in SEQ ID NO:365 or wherein the nucleotide sequence encodes a polypeptide comprising an amino acid sequence having 95 percent or greater sequence identity to the amino acid sequence set forth in SEQ ID NO:366;
   wherein the regulatory region is heterologous with respect to the nucleotide sequence; and
   wherein the transgenic plant is selected for having increased yield as compared to a control plant that does not comprise said exogenous nucleic acid when grown in soil containing elevated levels of $Al^{3+}$.

2. The transgenic plant of claim 1, wherein said plant is selected from the group consisting of *Panicum virgatum, Sorghum bicolor, Miscanthus giganteus, Saccharum* sp., *Populus balsamifera, Zea mays, Glycine max, Brassica napus, Triticum aestivum, Gossypium hirsutum, Oryza sativa, Helianthus annuus, Medicago sativa, Beta vulgaris,* or *Pennisetum glaucum.*

3. Progeny of the plant of claim 1, wherein said progeny comprises said exogenous nucleotide and has increased tolerance to elevated $Al^{3+}$ conditions as compared to that of a control plant that does not comprise said exogenous nucleic acid.

4. Seed from the transgenic plant of claim 1, said seed comprising said exogenous nucleic acid.

5. Vegetative tissue from the transgenic plant of claim 1, said tissue comprising said exogenous nucleic acid.

6. A food product comprising vegetative tissue from the transgenic plant of claim 1, said tissue comprising said exogenous nucleic acid.

7. A feed product comprising vegetative tissue from the transgenic plant of claim 1, said tissue comprising said exogenous nucleic acid.

8. A plant cell from the transgenic plant of claim 1.

9. The plant cell of claim 8, wherein said nucleotide sequence has 95 percent or greater sequence identity to the nucleotide sequence set forth in SEQ ID NO:365.

10. The plant cell of claim 8, wherein said nucleotide sequence comprises the nucleotide sequence set forth in SEQ ID NO:365, or wherein said nucleotide sequence encodes the polypeptide set forth in SEQ ID NO:366.

11. The plant cell of claim 8, wherein said nucleotide sequence encodes a polypeptide having 95 percent or greater sequence identity to said amino acid sequence set forth in SEQ ID NO:366.

12. The plant cell of claim 8, wherein said nucleotide sequence comprises the nucleotide sequence set forth in SEQ ID NO:365.

13. The plant cell of claim 8, wherein said regulatory region is a promoter.

* * * * *